US006737261B2

(12) United States Patent
Wei et al.

(10) Patent No.: US 6,737,261 B2
(45) Date of Patent: May 18, 2004

(54) ISOLATED NUCLEIC ACID MOLECULES ENCODING HUMAN LANOSTEROL SYNTHASE PROTEINS, AND RELATED PRODUCTS AND PROCESSES

(75) Inventors: Ming-Hui Wei, Germantown, MD (US); Chunhua Yan, Boyds, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/815,048

(22) Filed: Mar. 23, 2001

(65) Prior Publication Data

US 2002/0137131 A1 Sep. 26, 2002

(51) Int. Cl.[7] .................................................. C12N 9/90

(52) U.S. Cl. ................. 435/233; 435/320.1; 435/252.3; 435/254.11; 435/419; 435/325; 536/23.1; 536/23.2; 536/23.5

(58) Field of Search ............................... 536/23.1, 23.2, 536/23.5; 435/320.1, 252.3, 254.11, 419, 325, 233

(56) References Cited

PUBLICATIONS

Sung et al. Molecular Cloning of cDNA Encoding Human Lanosterol Synthase. Biol. Pharm. Bull. (1995) 18(10):1459–1461.*

Roessler et al. Structure of the human Lanosterol Synthase gene and its analysis as a candidate for holoprosencephaly (HPE1). Human Genetics (1999) 105:489–495.*

Baker et al. "Molecular Cloning of the Human Gene Encoding Lanosterol Synthase from a Liver cDNA Library." Biochem. Biophys. Res. Commun. 1995. vol. 213, No. 1, pp. 154–160.

* cited by examiner

*Primary Examiner*—Ponnathapu Achutamurthy
*Assistant Examiner*—Kathleen Kerr
(74) *Attorney, Agent, or Firm*—Celera Genomics; Justin D. Karjala

(57) ABSTRACT

The present invention provides amino acid sequences of human lanosterol synthase proteins and nucleic acid sequences encoding these lanosterol synthase proteins. The present invention provides isolated lanosterol synthase proteins and encoding nucleic acid molecules, vectors and host cells containing these nucleic acid molecules, and processes for producing the lanosterol synthase proteins.

23 Claims, 33 Drawing Sheets

```
   1 TGGCAGTGGG CGGCGTAGAG CACTGCAGCA GCAATGACGG AGGGCACGTG
  51 TCTGCGGCGC CGAGGGGGCC CCTACAAGAC CGAGCCCGCC ACCGACCTCG
 101 GCCGCTGGCG ACTCAACTGC GAGAGGGGCC GGCAGACGTG GACCTACCTG
 151 CAGGACGAGC GCGCCGGCCG CGAGCAGACC GGCCTGGAAG CCTACGCCCT
 201 GGGGCTGGAC ACCAAGAATT ACTTTAAGGA CTTGCCCAAA GCCCACACCG
 251 CCTTTGAGGG GGCTCTGAAC GGGATGACAT TTTACGTGGG GCTGCAGGCT
 301 GAGGATGGGC ACTGGACGGG TGATTATGGT GGCCCACTTT TCCTCCTGCC
 351 AGGCCTCCTG ATCACTTGCC ACGTGGCACG CATCCCTCTG CCAGCCGGAT
 401 ACAGAGAAGA GATTGTGCGG TACCTGCGGC ACATTGAGGA TAAGTCCACC
 451 GTGTTTGGGA CTGCGCTCAA CTATGTGTCT CTCAGAATTC TGGGTGTTGG
 501 GCCTGACGAT CCTGACCTGG TACGAGCCCG GAACATTCTT CACAAGAAAG
 551 GTGGTGCTGT GGCCATCCCC TCCTGGGGGA AGTTCTGGCT GGCTGTCCTG
 601 AATGTTTACA GCTGGGAAGG CCTCAATACC CTGTTCCCAG AGATGTGGCT
 651 GTTTCCTGAC TGGGCACCGG CACACCCCTC CACACTCTGG TGCCACTGCC
 701 GGCAGGTGTA CCTGCCCATG AGCTACTGCT ACGCCGTTCG GCTGAGTGCC
 751 GCGGAAGACC CGCTGGTCCA GAGCCTCCGC CAGGAGCTCT ATGTGGAGGA
 801 CTTCGCCAGC ATTGACTGGC TGGCGCAGAG GAACAACGTG GCCCCCGACG
 851 AGCTGTACAC GCCGCACAGC TGGCTGCTCC GCGTGGTATA TGCGCTCCTC
 901 AACCTGTATG AGCACCACCA CAGTGCCCAC CTGCGGCAGC GGGCCGTGCA
 951 GAAGCTGTAT GAACACATTG TGGCCGACGA CCGATTCACC AAGAGCATCA
1001 GCATCGGCCC GATCTCGAAA ACCATCAACA TGCTTGTGCG CTGGTATGTG
1051 GACGGGCCCG CCTCCACTGC CTTCCAGGAG CATGTCTCCA GAATCCCGGA
1101 CTATCTCTGG ATGGGCCTTG ACGGCATGAA AATGCAGGGC ACCAACGGCT
1151 CACAGATCTG GGACACCGCA TTCGCCATCC AGGCTCTGCT TGAGGCGGGC
1201 GGGCACCACA GGCCCGAGTT TTCGTCCTGC CTGCAGAAGG CTCATGAGTT
1251 CCTGAGGCTC TCACAGGTCC CAGATAACCC TCCCGACTAC CAGAAGTACT
1301 ACCGCCAGAT GCGCAAGGGT GGCTTCTCCT TCAGTACGCT GGACTGCGGC
1351 TGGATCGTTT CTGACTGCAC GGCTGAGGCC TTGAAGGCTG TGCTGCTCCT
1401 GCAGGAGAAG TGTCCCCATG TCACCGAGCA CATCCCCAGA GAACGGCTCT
1451 GCGATGCTGT GGCTGTGCTG CTGAACATGA GAAATCCAGA TGGAGGGTTC
1501 GCCACCTATG AGACCAAGCG TGGGGGGCAC TTGCTGGAGC TGCTGAACCC
1551 CTCGGAGGTC TTCGGGGACA TCATGATTGA CTACACCTAT GTGGAGTGCA
1601 CCTCAGCCGT GATGCAGGCG CTTAAGTATT TCCACAAGCG TTTCCCGGAG
1651 CACAGGGCAG CGGAGATCCG GGAGACCCTC ACGCAGGGCT TAGAGTTCTG
1701 TCGGCGGCAG CAGAGGGCCG ATGGCTCCTG GGAAGGCTCC TGGGGAGTTT
1751 GCTTCACCTA CGGCACCTGG TTTGGCCTGG AGGCCTTCGC CTGTATGGGG
1801 CAGACCTACC GAGATGGGAC TGCCTGTGCA GAGGTCTCCC GGGCCTGTGA
1851 CTTCCTGCTG TCCCGGCAGA TGGCAGACGG AGGCTGGGGG GAGGACTTTG
1901 AGTCCTGCGA GGAGCGGCGT TATGTGCAGA GTGCCCAGTC CCAGATCCAC
1951 AACACATGCT GGGCCATGAT GGGGCTGATG GCCGTTCGGC ATCCTGACAT
2001 CGAGGCCCAG GAGAGAGGAG TCCGGTGTCT ACTTGAGAAA CAGCTCCCCA
2051 ATGGCGACTG GCCGCAGGAA AACATTGCTG GGGTCTTCAA CAAGTCCTGT
2101 GCCATCTCCT ACACGAGCTA CAGGAACATC TTCCCCATCT GGGCCCTCGG
2151 CCGCTTCTCC CAGCTGTACC CTGAGAGAGC CCTTGCTGGC CACCCCTGAG
2201 AACATGCCTA CCTGCTGGGT GCCGTCTGTG CGTTCCAGTG AGGCCAAGGG
2251 GTCCTGGCCG GGTTGGGGAG CCCTCCCATA ACCCTGTCTT GGGCTCCAAC
2301 CCCTCAACCT CTATCTCATA GATGTGAATC TGGGGGCCAG GCTGGAGGCA
2351 GGGATGGGGA CAGGGTGGGT GGCTTAGACT CTTGATTTTT ACTGTAGGTT
2401 CATTTCTGAA AGTAGCTTGT CGGGCTTGGG TGAGGAAGGG GGCACAGGAG
2451 CCGTGACCCC TGAGGAGGCA CAGCGCCTTC TGCCACCTCT GGGCACGGCC
2501 TCAAGGTAGT GAGGCTAGGA GGTTTTTTCT GACCAATAGC TGAGTTCTTG
2551 GGAGAGGAGC AGCTGTGCCT GTGTGATTCC TTAGTGTCGA GTGGGCTCTG
2601 GGCTGGGGTC GGCCCTGGGC AGGCTTCTCC TGCACCTTTT GTCTGCTGGG
2651 CTGAGGGACA CGAGGGCAAC CCTGTGACAA TGGCAGGTAG TGTGCATCCG
2701 TGAATAGCCC AGTGCGGGGG TTGCTCATGG AGCATCCTGA GGCCGTGCAG
2751 CAGGGAGCCC CATGCCCCTG GGTCGTGAGC TTGCCTGCGT ATGGGGTGGT
2801 GTCATGGAGC CTCATGCCCC TGGGTCGTGA GCTCGCCTGA GTATGGGGTG
2851 GTGTCATGGA GCCGCATACC CCTGGGTTGT GAGCTCGCCT GCATATGCAG
2901 GGTCTGTCAT GGAACATCCC AAGTCTGTGC AGCAGGGAGC CCCATGCCCC
2951 TGGGACATGA ACCCACCTGC GTGGAATGCT GTTTGTGAGG TGTCTACAGG
3001 GTTTATAGTA GTCTTGTGGA CACAGAAATG CACAGGGGAC ACTTACGGAC
3051 ACAGAAATGC ACAGGGGAGG CCGAGCATAA CCAGGGGTGA GGGGCAGGCA
3101 GCAGTTGTAG TTACTGCCGC GGGGCACTGC TATGTGCAGG GACAGCCAGC
```

FIGURE 1, page 1 of 3

```
3151 GCCCAGCCCA TCACCACTCC CTGGGCTGGC TGGCAGGTAT GGCACCCTGG
3201 GAGCCCGGCA TATACCCAGG GCACCCCTAC GGCTGCCGCC AGTCTCATGC
3251 CCAGGTGGGT GCTCTGGGCT GGAGCGAGGG CCAGGTTTTG GGCCGAGGCT
3301 TCCCCAGGCA ATCCTGTGAG CTCCCTTCTA GCCTCTGACC CAGTCTGGTC
3351 TGGCTTGCAT GGATGTAGGG CTTGGGGTGG GAAGTTCAGG TCCTGGCTTT
3401 GCCTTTGCCT GATGTGGATG AGCAGCTCAC ATGCTCAGGG CCACCTGAGA
3451 CTGTCACTGC TCTCCCCTGG CTACTGGGAG GAGTCACTGA GAGCTTCGTT
3501 ACCCCTGCTG CCTTGCCCAG GGCACACCCT ATACCTCCTC ATCTGCTCTT
3551 CCCCTCCCTG CCGCCTTCTG GGCAGGTAGC AGTCCCTGGC CTCTCCCCCT
3601 GGCTGATCAC TCTCCCTCAG GCAGTGGAGA TCTGCGTCTG GACACCCTCA
3651 GATCCTGTCA TTGCCTGCCC AGAGTCCTTC AGGGGCACCC CTCTGCCTTG
3701 GTGTGCGGTC CAGGGCTCTC ACCCAGGTGC CGCACCCTCT GGGGTCTTCT
3751 GTCCAGCTCC CTTGCCCCAT GTGCTGTCAC TGACTCTCCT TGGGACTCGC
3801 CTGCCTGCTC AGAGCCCTGC AGGGCTTGGT CAGCTGCCTG TTCAGTGTCA
3851 ACACTTCCCT GCACATCTTA AAACTGGGCT TTATTTTCGC TGAAGGAACT
3901 GTGTTGGGAC CCTTGACATC TGTCAGGTTT GCACATGCTG TTTTTTTTTC
3951 TCAGCCCACG TGTTCTCCCC CACGTGGGGT AGCAGCAGGA CAGACAGTGA
4001 ATCACAGAGT CTGCCCTGAG CAGAGGCTGC TGTCCCTGGG ACTCCTAGCC
4051 ATGGTCAGAC TGTACAAAAC GGTTTTCCAG AAATGAAATG TAAATCCATT
4101 TTTATACTGA AAATGTTACT GAAAGTCACT TTTATGAGCA TCTGCCTTAA
4151 TAAACAGACA TTGATTCCCT TAAAAAAAAA AAAAAAAAAA AAAAAAAAAA
4201 AAAAAAAAAA AAAAAAAAAA AAAAAAAAAA AAAAAAAAA  (SEQ ID NO:1)
```

FEATURES:
5'UTR: 1-33
Start Codon: 34
Stop Codon: 2197
3'UTR: 2200

Homologous proteins:

Top 10 BLAST Hits

| | Score | E |
|---|---|---|
| CRA\|18000005000949 /altid=gi\|4505027 /def=ref\|NP_002331.1\| lano... | 1530 | 0.0 |
| CRA\|18000005227733 /altid=gi\|4808278 /def=emb\|CAB42828.1\| (AJ23... | 1524 | 0.0 |
| CRA\|18000005013642 /altid=gi\|1098635 /def=gb\|AAA91023.1\| (U3135... | 1315 | 0.0 |
| CRA\|18000004977416 /altid=gi\|1352388 /def=sp\|P48450\|ERG7_RAT LA... | 1305 | 0.0 |
| CRA\|18000005002424 /altid=gi\|984145 /def=emb\|CAA61078.1\| (X8780... | 1224 | 0.0 |
| CRA\|100000004433519 /altid=gi\|8886139 /def=gb\|AAF80384.1\|AF1599... | 689 | 0.0 |
| CRA\|335001098658178 /altid=gi\|11279144 /def=pir\|\|T48782 lanoste... | 611 | e-173 |
| CRA\|18000005223063 /altid=gi\|4589852 /def=dbj\|BAA76902.1\| (AB02... | 609 | e-173 |
| CRA\|18000005171896 /altid=gi\|3688598 /def=dbj\|BAA33460.1\| (AB00... | 607 | e-172 |
| CRA\|1000682333668 /altid=gi\|6045133 /def=dbj\|BAA85266.1\| (AB033... | 605 | e-172 |

BLAST dbEST hits:

| | Score | E |
|---|---|---|
| gi\|10993792 /dataset=dbest /taxon=96... | 1538 | 0.0 |
| gi\|10159427 /dataset=dbest /taxon=96... | 1358 | 0.0 |
| gi\|9340844 /dataset=dbest /taxon=960... | 1108 | 0.0 |
| gi\|11251687 /dataset=dbest /taxon=96... | 1065 | 0.0 |
| gi\|11258382 /dataset=dbest /taxon=96... | 995 | 0.0 |
| gi\|10322370 /dataset=dbest /taxon=96... | 910 | 0.0 |

FIGURE 1, page 2 of 3

EXPRESSION INFORMATION FOR MODULATORY USE:

library source:

From BLAST dbEST hits:

gi|10993792 teratocarcinoma
gi|10159427 ovary
gi|9340844 uterus
gi|11251687 muscle
gi|11258382 brain
gi|10322370 colon From tissue screening panels:

hippocampus

FIGURE 1, page 3 of 3

```
  1 MTEGTCLRRR GGPYKTEPAT DLGRWRLNCE RGRQTWTYLQ DERAGREQTG
 51 LEAYALGLDT KNYFKDLPKA HTAFEGALNG MTFYVGLQAE DGHWTGDYGG
101 PLFLLPGLLI TCHVARIPLP AGYREEIVRY LRHIEDKSTV FGTALNYVSL
151 RILGVGPDDP DLVRARNILH KKGGAVAIPS WGKFWLAVLN VYSWEGLNTL
201 FPEMWLFPDW APAHPSTLWC HCRQVYLPMS YCYAVRLSAA EDPLVQSLRQ
251 ELYVEDFASI DWLAQRNNVA PDELYTPHSW LLRVVYALLN LYEHHHSAHL
301 RQRAVQKLYE HIVADDRFTK SISIGPISKT INMLVRWYVD GPASTAFQEH
351 VSRIPDYLWM GLDGMKMQGT NGSQIWDTAF AIQALLEAGG HHRPEFSSCL
401 QKAHEFLRLS QVPDNPPDYQ KYYRQMRKGG FSFSTLDCGW IVSDCTAEAL
451 KAVLLLQEKC PHVTEHIPRE RLCDAVAVLL NMRNPDGGFA TYETKRGGHL
501 LELLNPSEVF GDIMIDYTYV ECTSAVMQAL KYFHKRFPEH RAAEIRETLT
551 QGLEFCRRQQ RADGSWEGSW GVCFTYGTWF GLEAFACMGQ TYRDGTACAE
601 VSRACDFLLS RQMADGGWGE DFESCEERRY VQSAQSQIHN TCWAMMGLMA
651 VRHPDIEAQE RGVRCLLEKQ LPNGDWPQEN IAGVFNKSCA ISYTSYRNIF
701 PIWALGRFSQ LYPERALAGH P   (SEQ ID NO:2)
```

FEATURES:
Functional domains and key regions:
[1] PDOC00001 PS00001 ASN_GLYCOSYLATION
N-glycosylation site Number of matches: 2

```
1    371-374 NGSQ
2    686-689 NKSC
```

[2] PDOC00005 PS00005 PKC_PHOSPHO_SITE
Protein kinase C phosphorylation site

Number of matches: 5

```
1    149-151 SLR
2    247-249 SLR
3    149-151 SLR
4    247-249 SLR
5    494-496 TKR
```

[3] PDOC00006 PS00006 CK2_PHOSPHO_SITE
Casein kinase II phosphorylation site

Number of matches: 7

```
1      49-52 TGLE
2      72-75 TAFE
3    238-241 SAAE
4    434-437 STLD
5    518-521 TYVE
6    591-594 TYRD
7    624-627 SCEE
```

FIGURE 2, page 1 of 4

[4] PDOC00008 PS00008 MYRISTYL
N-myristoylation site

Number of matches: 11

| | | |
|---|---|---|
| 1 | 76-81 | GALNGM |
| 2 | 107-112 | GLLITC |
| 3 | 142-147 | GTALNY |
| 4 | 173-178 | GGAVAI |
| 5 | 369-374 | GTNGSQ |
| 6 | 487-492 | GGFATY |
| 7 | 552-557 | GLEFCR |
| 8 | 564-569 | GSWEGS |
| 9 | 571-576 | GVCFTY |
| 10 | 577-582 | GTWFGL |
| 11 | 595-600 | GTACAE |

[5] PDOC00825 PS01074 TERPENE_SYNTHASES
Terpene synthases signature 563-577 DGSWEGSWGVCFTYG

Membrane spanning structure and domains:

| Helix | Begin | End | Score | Certainty |
|---|---|---|---|---|
| 1 | 95 | 115 | 1.321 | Certain |
| 2 | 173 | 193 | 0.944 | Putative |
| 3 | 569 | 589 | 1.311 | Certain |

FIGURE 2, page 2 of 4

BLAST Alignment to Top Hit:

```
>CRA|18000005000949 /altid=gi|4505027 /def=ref|NP_002331.1|
          lanosterol synthase (2,3-oxidosqualene-lanosterol
          cyclase); Lanosterol synthase; human lanosterol synthase
          [Homo sapiens] /org=Homo sapiens /taxon=9606
          /dataset=nraa /length=732
         Length = 732

 Score = 1530 bits (3917), Expect = 0.0
 Identities = 720/732 (98%), Positives = 721/732 (98%), Gaps = 11/732 (1%)

Query: 1   MTEGTCLRRRGGPYKTEPATDLGRWRLNCERGRQTWTYLQDERAGREQTGLEAYALGLDT 60
            MTEGTCLRRRGGPYKTEPATDLGRWRLNCERGRQTWTYLQDERAGREQTGLEAYALGLDT
Sbjct: 1   MTEGTCLRRRGGPYKTEPATDLGRWRLNCERGRQTWTYLQDERAGREQTGLEAYALGLDT 60

Query: 61  KNYFKDLPKAHTAFEGALNGMTFYVGLQAEDGHWTGDYGGPLFLLPGLLITCHVARIPLP 120
            KNYFKDLPKAHTAFEGALNGMTFYVGLQAEDGHWTGDYGGPLFLLPGLLITCHVARIPLP
Sbjct: 61  KNYFKDLPKAHTAFEGALNGMTFYVGLQAEDGHWTGDYGGPLFLLPGLLITCHVARIPLP 120

Query: 121 AGYREEIVRYLR-----------HIEDKSTVFGTALNYVSLRILGVGPDDPDLVRARNIL 169
            AGYREEIVRYLR           HIEDKSTVFGTALNYVSLRILGVGPDDPDLVRARNIL
Sbjct: 121 AGYREEIVRYLRSVQLPDGGWGLHIEDKSTVFGTALNYVSLRILGVGPDDPDLVRARNIL 180

Query: 170 HKKGGAVAIPSWGKFWLAVLNVYSWEGLNTLFPEMWLFPDWAPAHPSTLWCHCRQVYLPM 229
            HKKGGAVAIPSWGKFWLAVLNVYSWEGLNTLFPEMWLFPDWAPAHPSTLWCHCRQVYLPM
Sbjct: 181 HKKGGAVAIPSWGKFWLAVLNVYSWEGLNTLFPEMWLFPDWAPAHPSTLWCHCRQVYLPM 240

Query: 230 SYCYAVRLSAAEDPLVQSLRQELYVEDFASIDWLAQRNNVAPDELYTPHSWLLRVVYALL 289
            SYCYAVRLSAAEDPLVQSLRQELYVEDFASIDWLAQRNNVAPDELYTPHSWLLRVVYALL
Sbjct: 241 SYCYAVRLSAAEDPLVQSLRQELYVEDFASIDWLAQRNNVAPDELYTPHSWLLRVVYALL 300

Query: 290 NLYEHHHSAHLRQRAVQKLYEHIVADDRFTKSISIGPISKTINMLVRWYVDGPASTAFQE 349
            NLYEHHHSAHLRQRAVQKLYEHIVADDRFTKSISIGPISKTINMLVRWYVDGPASTAFQE
Sbjct: 301 NLYEHHHSAHLRQRAVQKLYEHIVADDRFTKSISIGPISKTINMLVRWYVDGPASTAFQE 360

Query: 350 HVSRIPDYLWMGLDGMKMQGTNGSQIWDTAFAIQALLEAGGHHRPEFSSCLQKAHEFLRL 409
            HVSRIPDYLWMGLDGMKMQGTNGSQIWDTAFAIQALLEAGGHHRPEFSSCLQKAHEFLRL
Sbjct: 361 HVSRIPDYLWMGLDGMKMQGTNGSQIWDTAFAIQALLEAGGHHRPEFSSCLQKAHEFLRL 420

Query: 410 SQVPDNPPDYQKYYRQMRKGGFSFSTLDCGWIVSDCTAEALKAVLLLQEKCPHVTEHIPR 469
            SQVPDNPPDYQKYYRQMRKGGFSFSTLDCGWIVSDCTAEALKAVLLLQEKCPHVTEHIPR
Sbjct: 421 SQVPDNPPDYQKYYRQMRKGGFSFSTLDCGWIVSDCTAEALKAVLLLQEKCPHVTEHIPR 480

Query: 470 ERLCDAVAVLLNMRNPDGGFATYETKRGGHLLELLNPSEVFGDIMIDYTYVECTSAVMQA 529
            ERLCDAVAVLLNMRNPDGGFATYETKRGGHLLELLNPSEVFGDIMIDYTYVECTSAVMQA
Sbjct: 481 ERLCDAVAVLLNMRNPDGGFATYETKRGGHLLELLNPSEVFGDIMIDYTYVECTSAVMQA 540

Query: 530 LKYFHKRFPEHRAAEIRETLTQGLEFCRRQQRADGSWEGSWGVCFTYGTWFGLEAFACMG 589
            LKYFHKRFPEHRAAEIRETLTQGLEFCRRQQRADGSWEGSWGVCFTYGTWFGLEAFACMG
Sbjct: 541 LKYFHKRFPEHRAAEIRETLTQGLEFCRRQQRADGSWEGSWGVCFTYGTWFGLEAFACMG 600

Query: 590 QTYRDGTACAEVSRACDFLLSRQMADGGWGEDFESCEERRYVQSAQSQIHNTCWAMMGLM 649
            QTYRDGTACAEVSRACDFLLSRQMADGGWGEDFESCEERRY+QSAQSQIHNTCWAMMGLM
Sbjct: 601 QTYRDGTACAEVSRACDFLLSRQMADGGWGEDFESCEERRYLQSAQSQIHNTCWAMMGLM 660

Query: 650 AVRHPDIEAQERGVRCLLEKQLPNGDWPQENIAGVFNKSCAISYTSYRNIFPIWALGRFS 709
            AVRHPDIEAQERGVRCLLEKQLPNGDWPQENIAGVFNKSCAISYTSYRNIFPIWALGRFS
Sbjct: 661 AVRHPDIEAQERGVRCLLEKQLPNGDWPQENIAGVFNKSCAISYTSYRNIFPIWALGRFS 720

Query: 710 QLYPERALAGHP 721
            QLYPERALAGHP
Sbjct: 721 QLYPERALAGHP 732  (SEQ ID NO:4)
```

FIGURE 2, page 3 of 4

Hmmer search results (Pfam):

| Model | Description | Score | E-value | N |
|---|---|---|---|---|
| PF00432 | Prenyltransferase and squalene oxidase repea | 83.9 | 1.7e-22 | 3 |

Parsed for domains:

| Model | Domain | seq-f | seq-t | | hmm-f | hmm-t | | score | E-value |
|---|---|---|---|---|---|---|---|---|---|
| PF00432 | 1/3 | 133 | 154 | .. | 23 | 45 | .] | 6.6 | 3.8 |
| PF00432 | 2/3 | 547 | 589 | .. | 1 | 45 | [] | 40.1 | 8e-10 |
| PF00432 | 3/3 | 599 | 647 | .. | 1 | 45 | [] | 39.4 | 1.3e-09 |

FIGURE 2, page 4 of 4

```
   1 TCATGACTGC CCCTAGAAGC TTAACTGTGT CAATTCTCAG ACGTAGTTTA
  51 CAGCTTTTTC TTTTCTTTCA GACATTAAAA AGAGCGGATT ATTTTACTCA
 101 TAAAAAGTCC AGTCCATTAA GATATCAAAA CTCAAACTCT TATCCAGTTG
 151 AAACCTCTTC CCTCACCTAG CTTTGCCAGG TTCAGTGTGA GATTCCATCC
 201 AGGCTGAAGC CCCTTATCCC TATTCTTCAT GTTTCTACAT GGAGGAACTT
 251 ACCTGGAGAA AAACTTCCAG CCTCTTTCTG CTTCCAGAGA AGTAGAGTGA
 301 CTCATTTGAT TGAATTTCAG AGAACAGATA GGGTGGAGTG TGCTCAGGCT
 351 CCTCTGGGTA CTCTTTCTGG GGTCTGTGGG TTGACTGGAG GGGTGTCTTC
 401 TGGTGGGCAC TCAATTGCAT AGTGCTTGGT GAGGCAGTTT CATGGCCTAG
 451 AGGCTGGGGG ATATGTTTGT CTGACTTACG GGTGATTTAG TAGCTTGCCC
 501 TCTTGCTTGC AGATTTAAGC CTTGTCCTTC AAGCTAGGTT TTTAATTTGT
 551 GGCAAAGCTG ATATTTTGAT ACCCACCCAT CTTATTGCTG TGTCTTTTTC
 601 ATCCGTTTCT GAACTGGGAT AGGAAGAGGT GATTATCCTT GATTGTCTAA
 651 AACCCCGCTA TTCCACTGTG GGGAAGGTGC CTGTGGGTAT TCTTTTGTCC
 701 ACTCTCTCTT CCAACTTTCT CCTCCGGCTT GCTGTGGCTC ACCGCCCCTT
 751 CGAAGTTAGG CTGGGGGTAG GAATTGAGGA GTGGGTGCCG AAATGCTCAC
 801 TAGGCTGGGG CAGTTGTAAC TGGATGTCAG GGCTTCTGTG GGCCAGGTGA
 851 AGACATGCTG GGGTCTTCTG TGGGTCCTTG ACCTGACTTA GGGACCACTG
 901 GCTGCAGCCT CCAGACGTCA GCCATGTTTC CAACAGTCAG ACGCCCCCTG
 951 CCCTGTTGCG CCCGGCTGTC CCTTCCAAGT TCGGTCACTC GCTCTGCCTC
1001 CATCTTCCTC TTCCCTCTGC TGCTAAGGCT TTTCACCTTT AATTTCTCCT
1051 GGGGCCACCC CCAACTCCAG CGACCCCGTG AGCAGCTGAG GCTCTACCGC
1101 GCTCGGTCCT GGCCAGCGAC GCAGCCCTTC CCTGGCGGGG CTCCAGGGCT
1151 TCTGGCCCCT GTGGTCCGCC AGGTGTGGGG GCCCACGGCC TCACCGCGCC
1201 TACCCCACTC CCCCCGGCGA AGCTACGCGG CGCTCAGCTT CCCAGGGACG
1251 CCGGCGGCGC CCTCGGCTCC TCCGCTCCGC CCCGCCCTCC CCCTGGTCTC
1301 GCACTGGAGC CGACGGCCCG CGCCCACCTC ACCTCAGGGC GGCCTCCCGC
1351 CCCCACCCCC GGCCCCGGCG TCCGGGCAAA TCCTGCAGCG CGAGAGCAAT
1401 TCCCTGCCAC CCGACCTTCG CACTCGCTGT CGCTCGCTCG AGCCTCGCTC
1451 CCCACGTCCT TCCTTCCGAC CCGCGGCTGG ACCCTCCTCA CAAATTTCTC
1501 AGAGAGGCTC ACCTCAAAGC GCGGCGCACG AGGCCGGGCT CCCGGGACGC
1551 AAGCCTCTAG AGGGCGCGCG AGAGGCCCCG CCCCCGCCCT TCGGCCCCAC
1601 CCACCAGCCC CGCCCCCACC CGCACCCACC AGGCCCCGCC CCCACCTCCC
1651 CACCCACCAG CCCCGCCCCC ACCTCCCCAC CCACCAGCCC CGCCCCTCAT
1701 GCCCCGCCAA TAAGGCCCCA CCCGCCTCCC CCGTCCCGTC GCCTTCACCC
1751 ACCATCCCCG CTCCCTCAGG CCCCGCCCCA CGCCGCATGG GGCACCAAGC
1801 GCTCCACCAC TGTGGTCGCC TGGCACACCC CGGGGTCACG CTCGCGGCGC
1851 TCTGATTGGT TGCGTGGGCG TCGGCCCACC TAAGCCTGAG CGCCTGCCGA
1901 GGCCTGCGCC TGCGTAGTGC GCGCGGGAGG GGCGGGAGGG GCGGGAGGGG
1951 CGGGAGGGGC GGGGCTGGGC GGCAGGTCCC GGGTGCGGAC ATCTGGCAGC
2001 TGGCAGTGGG CGGCGTAGAG CACTGCAGCA GCAATGACGG AGGGCACGTG
2051 AGTCCCCTCG CCCCGGGCTC CTGACGAATG CGGGGTGGTC CTAGGTGCTG
2101 AGGAGAGCGC GACTGGGGCA GTGGGCCGGC GGCCGGCGTT GGGGCGGGGC
2151 CTGGGTCGCT GATGGCCGGT GGTCCTCAGG TGTCTGCGGC GCCGAGGGGG
2201 CCCCTACAAG ACCGAGCCCG CCACCGACCT CGGCCGCTGG CGACTCAACT
2251 GCGAGAGGGG CCGGCAGACG TGGACCTACC TGCAGGACGA GCGCGCCGGC
2301 CGCGAGCAGA CCGGCCTGGA AGCCTACGCC CTGGGGCTGG ACACCGTAAG
2351 TTGCTTCCGC GGAGCGTCAG CGAGCTCGGG ACCCTGAGGG GTGAGCCGTG
2401 AGGAGCACGT TTTCTCTCAG AAAGGCGGGT GGGAGGACCC GGCCAGCGAC
2451 GCCCATCCCC AAGGCGAGCG CCCACGGGAA CTGCGTTCGC GGGCCCCTCC
2501 GCTTCAGCCC CTTCATCTCT AAACCACGCA TAGGAGACTC CTAATGTTTT
2551 ATTTTTTAGC ACCTTATTTT GAGATAATTT TTGACTTATA GGAGAGTTGC
2601 AAAGATAGTT GTAACTTTGT TTTTATTCAC AAAAAGTGTT TGGATCCACT
2651 GTCTTAGTTG TGTGCATTGT AAGAGATTTT GGTCGTCAGA GTCTGCAGTG
2701 TAAACAGGGT CTCCTGCCGA GCCCCGGCCA CCGAGGGAAA GGCTGTGCCG
2751 CCCCTTGGGC CCTCTTTGAG AGGCCCGAGT CCCAGGCCCA GGTCGGCACC
2801 CGTGCCCCAC CCTACAGTCT GGGTGCCTGG TTTATTCCAG ACATCTTGGA
2851 GAAGTTGTGA AGAATACATG ACTGGCAAAT AAAGCAACGA AAATGTGCAG
2901 CTGTTCTTTT ACTTTGCTGA GGTGTGATGC TCTCATCAAA GAGTTTCAGA
2951 CTTTTGATGG AAACAGCTGA AACTTTTAAA GTAATTTACA TTCACTGTTT
3001 TGACTTGGGC TGTATGTGAA GAGGGTTCCT CTGGCCGGGC AACAGTCCCG
3051 TCAGCTATCT CTTTTTTTTT TTTTCGATCT CTTTGCAGAA GAATTACTTT
3101 AAGGACTTGC CCAAAGCCCA CACCGCCTTT GAGGGGGCTC TGAACGGGAT
```

FIGURE 3, page 1 of 26

```
3151 GACATTTTAC GTGGGGCTGC AGGCTGAGGA TGGGCACTGG ACGGGTGATT
3201 ATGGTGGCCC ACTTTTCCTC CTGCCAGGTA GGAGTATGCT GCCCCAGCCT
3251 GATGGTATGG CCACCCTGGA TCACCCTTGG GATCCTGGCC CAGCCTGGTC
3301 TAGGGTTTTG ATGAAGCAGG TGAAAATCCA GGGGCTCACA AGAAAAGGGC
3351 TGGCAAACTC TGCCCTATGT CAGAGTCGTC CTGCTATTGG TCTAGGGGAT
3401 CAGCTAGCCT TGCCAGTGTA GGGTGACAGG CTCTCTGATA AGAGAAGCAA
3451 GTGGTTCTCT AGGGCTCTGT GTTGCCTTGA GGGAGGAGGA AGGTGGGCTT
3501 TGAAGTCTCA GTACAGGATG GGATGGACAT TCCAGGTGGA AGGCCCAGCC
3551 TATGCCAAGG GGCTGTAGGT GGGCAGAGTG GTGGGTGGGG AGCTGATATC
3601 TGCTGTGAAC TTCCTCGGGG CTATTGCAGG AGAGCTTCAG GTTCAGGCTG
3651 GTGAGTAGGA GGAGCATAGC AGTTGGACTG CCTGGGTATT GAACTGATTT
3701 GGCTACACAA GACTATTTTG CATCCTGGGA GTGTTTCTCT ACAGAAATCC
3751 TCAGCCTTGT AAAATGGGAA ATTCCCTCCT ATGAATTTAT GCAATAGGAC
3801 TTTTTTCCCT AGTGACTTGT AATCACATTG TTTCAATGAC GTGAATTCCT
3851 ACATAAATAG GTTTTGTTTC TGTGATAACT CTTACTGATA CATCATTTTC
3901 TTTTACTACG CTGACTTTGT AATAGATAGA AAGTCCTTAT ATACCTTTGT
3951 TGCCTTTCTT TTTAAAACAT CTCTTACCTG TGTCTATTCA TTTACTCATC
4001 CAAATTGCCT TTATCCTGAT TTTGTCCCAG ACTTGAAATG AAGTTGCAAT
4051 AGGCTTATAT GTTAGTTTGG GAAGAGTTGG CCTTTAACGT TAAAAACAGT
4101 TCCATGGTGT TTACTGTAGG CCAAGCCCTG CTCAAGGCCT GTTCTTCTTT
4151 TAGTCCTTAG AATAAGCCTA ATGAGATACA TTAGAAAGCT GAGGCACATT
4201 TATTCCAGGT AACCAGACTA GCAGGAGGAG CACTGGGATC CCCATCTCTG
4251 CTTTGACTTC TAGCCCTGCT GCCACCTGGA CTGTACAGCA TTGAGTTTTT
4301 CTGTCCTGGG ATTTGAGGGC CTGTCCTTAG GGGAAGTCAA GGTGCTCTTC
4351 TTCCCTTGGC CCCATCAGGG CCTGTTTAGA CTGTTCTCAG GGCTCGTGGT
4401 AAGGCAATGA CATAGAGTTG GTCAGGAGAT GGGTCAGCCC CACTTTGCCT
4451 CTGTAGCCTG ACCTGTGACA GGATTGGAAT CAGGTTTGGT CATGTGCACA
4501 GTGTCAGGCA TGCAGTGGTG CTTGGTCAGT GGGGATTACT GTGTTGTTTG
4551 TTCTTGCTGC TTTGGCTCTG GGCTTAGCTG GCTGGGACCC TTCCTGTGGG
4601 CTGGCTGTGA GTTGGAGTTT TTTTGTATTT TTTTTTTTTT TTTGAGACAG
4651 CGTTCGCTCT TGTTCCCCAG GCTGGAGTGC AATGGCACAA TTTTGGCTCG
4701 TTGCAGCCTC TGCCTCCTGG GTGCAAGTGA TTCTCCTGCC TCAGCCTCCT
4751 GTAGGGTCCA GCCCCACAGG GTCGGTAGGT TTTTCTCCCT GTGTGCGGAG
4801 ATGAGAGATT GTAGAAATAA AGACACAAGA CAGAGAGATG AAAGAAAAGA
4851 CAGCTGGGCC CCGGGGGACC ACTACCACCA AGACGTGGAA ACCGGTAGTG
4901 GCCCTGAATG CCAGGCTGCG CTGATATTTA TTGGATACAA GACAAAGGGG
4951 CAGGGTAAGG AGTGTGAGCC ATCTCCAATG ATAGGTAAGG TCACATGGGT
5001 CACGTGTCCA CTGGACAGTG GGCCCTTCCC TGCCTGGCAG CCGAGGCAGA
5051 GAGTGGGAGA GAGAGAGAGA GAGACAGCTT ATGCCATTAT TTCTGCATAT
5101 CAGAGACTTT TAGTACTTTC ACTAATTTTG CTACTGTTAT CTAAAAGGCA
5151 GAGCCAGGTG TACAGGGTGG AACATGAAAG TGGACTAGGA GCGTGACCAC
5201 TGAAGCACAG CATCACAGGG AGATGGTTAG GCCTCCGGAT AACTGCGGGT
5251 GGGCCTGACT GATGTCAGGC CGTCCCACAA GAGGTGGAGG AGTAGAGTCT
5301 TCTCTAAACT CCCCCGGGGA AAGGGAGATT CCCTTTCCCG GTATGCTAAG
5351 TAGCGGGTGT TTTTCCTTGA CACTGACGCT ACCGCTAGAC CACGGTTGGG
5401 TCCGCTTGGC AACGGGCCTC TTCCCAGATG CTGGCGTTAC CGCTAGACCA
5451 AGGAGCCCTC TAGTGGCCTT GTCCGGGCTT AACAGAAGGC TCTCACTCTT
5501 GTCTTCTGGT CACTTCTCAC TATGTCTCTT CAGCTCCTAT CTCTGTATGG
5551 CCTGGTTTTT CCTAGGTTAT GATTGTAGAG CGAGGATTAT TATAATATTG
5601 GAATAAAGAG TAATTGCTAC AAACTAATGA TTAATGATAT TCATATATAA
5651 TCATATGTAT GATCTAGATC TAGTATAACT CTTGTTGTTT TATATATTTT
5701 ATTATACTGG AACAGCTCGT GCCCTCGGTC TCTTGCCTTG GCACCAAGGT
5751 GGCTTGCCAC CCACAGCCTC TCGAGTAGCT GGGATTACAG CCATGTGCCA
5801 CCATGCCTGG CTAATTTTTG TATTTTTGGT AGAGACAGGT TTTCACCTTG
5851 TTGGTCAGGC TGGTCTCGAA CTCCTGACCT CGTGATCCCC CACCCCCCAC
5901 CCCCAGCCTC CCAAAGTGCT GGGATTACAG GCGTGAGCCA CTGCACCTGG
5951 CTGAGTTGGA GCTTTTCTTC CCTCTTTTTG GACTTTGGAA AATGCTCTTG
6001 GTCCATGATG CTATGTAGAC AGCTCCCGTT GACTGTGGCC TGTGCGGCAT
6051 TGGGCAGCAC TCTGGTGAAC ACTGAATCGG GTCTGACCTC CTAGCCCCAC
6101 CATTTACTGG CTGAGCCTCA GTTTCCTTGC CTGTAAAATC AGGAAGATGC
6151 TGGCTCTGCT CCTCTCTGCA CATTTCCCCG TCCTAACAAC ATTATAACTG
6201 TTAGGAAAGA GACGGGCTTG TTTTGGGATG GCTCATTTTA TGTGACCCTG
6251 TGCGCTGTCT CTGAGTCCAT CTGCCCTTCT TCCAGGGTGT AGGGACCAGC
```

FIGURE 3, page 2 of 26

```
6301 CCCACAGGGT CGGTGGGTCT CTCCCTGTGT GCGGCGATGA GAGAGTGTAG
6351 AAATAAAGAC ACAAGACAAA GAGATAAAAG ACAGCTGGGC CCGGGGGACC
6401 ACTGCCACCA ATGCATGGAG ACCAGTAGTG GCCCCGAATG TCTGGCTGTG
6451 CTGTTATTTA TTGGATACAA AGCAAAAGGG GCAGGGTAAA GAGTGTGAGT
6501 CATCTCCAGT GATAGGTAAG GTCACATGGG TCACGTGTCC ACTGGGACAG
6551 GGGGCCCTTC CCTGCCTGGC AGCCGAGGCA GAGAGAGGAG ACACAGAGAA
6601 AGAAAACTTA TGCCATTATT TCTGCATATC AGAGACTTTT AGTACTTTCA
6651 CTAATTGACT ACTGCTATCT AGAAGGCAGA GCCAGGTGTA CAGGATGGAA
6701 CATGAAGGCG GACTAGGAGC GTGACCACTG AAGCACAGCA TCACAGGGAG
6751 ACAGGCCTCC GGATAACTGC GGGCAGGTCT GACTAATGTG AGGCCCTCCA
6801 CAAGAGGTGG AGGAGCAGAG TCTTCTCTAA ATTCCCCCGG GGAAAGGGAG
6851 CCTCCCTTTC CCGGTCTGCT AAGTAGCGGG TGTTGTTCCT TGACACTTTT
6901 CGCTACCGCT AGACCACCGT CCGCTCGGCA ACGGGCGTCT TCCCAGACGC
6951 TGGCGTTACC ACTAGACCAA GGAGCCCTTT TGCTGGCCCC GTCCGGGCAT
7001 AACAGAAGGC TCGCACTCCT GTCTTCTGGT CACACCTCAC TATGTCCCCT
7051 CAGCTCCTAT CTCTGTATGG CCTGGTTTTT CCTAGGTTAT GATTGTAGAG
7101 CGAGGATTAT TATAATATTG GGATAAAGAG TAATTACTAC AAACTAATGA
7151 TTAATGATAT TCATATATCT CTAAGATCTA TATCTGGTAT AACTATTCTT
7201 GTTTTATATT TTATTATACT GGAACAGCTC GTGTCCTCGG TCTCTTGCCT
7251 TGGCGCCTGG GTGGCTTGCC GCCCACACAG GGCATGTCTG GATGGTTTGA
7301 ACACTAGGGC TTCTGATGCT CTAAGCCAGA GTCAGGTATT CATTCCATGG
7351 CACATGTGGC TGGGGTCTGC CCTGAGACCT GTCCCGTGCC AGGCTCTGGG
7401 GGCACATGGC TGATGGAACC AAGCATGGGG AGTGAAGGTG GAGGGTGGCC
7451 TGTGAGCACC ATGCCTGAGA GGACCAGGCT GGGGACGGAA GGTTCTTAGT
7501 GGATAATATT TATTGTCTCT GCCTCCCCCC TGACATTTGC AAAGCGGCAT
7551 ATGCTTGTAA AAAAATTTTG AAACAGAAAA ATATAAATAA ATAAGTAGGT
7601 ATTACCACAT GCAAGGGTGA CCAATTTTGT ATTTTTCTTC CCAGCAGATG
7651 TTAAAGCAAG ACCAACAGTC TCCCCTCATG GAAGGCCCAC TGATCTAAAA
7701 TGCTGGTTCC TTTTGGACCT TCAGGGCACT TGGGGGAGAC CTTCCTGAGG
7751 TGCTGTGCAG TGTCTGGTGT TTCTCAGACC CAGGTGGTCA TGGGAGCCAG
7801 GCGTGGCTGA GTGGGCTCTA CAGGCCCTAG GCAGGGAGCA TCGCCTGTGC
7851 TGTGGCTGAC GTTCCTTCTG GCCCTGTTCC CAAAGTTCCC CATGGGGGCC
7901 TGGGAGGAAT GGCCTTTCCA GGGGGTGTTT TTATGAGAAG GAGGTAGCTC
7951 CCTGTTGGAG TGAGGTGCTC AGGAGGAAAG GGGCCTGGTC TTAGCAGTCA
8001 TGACCACCTG TCCCCAGTGA GGAACATCTC TCCTGCCACA CAGGCCTCCT
8051 GATCACTTGC CACGTGGCAC GCATCCCTCT GCCAGCCGGA TACAGAGAAG
8101 AGATTGTGCG GTACCTGCGG TCAGTGCAGC TCCCTGACGG TGGCTGGGGC
8151 CTGTGAGTGT GCCTGCCCCT GTGTCACTGC ACATGTGCAT GTGTGTGTTC
8201 TCATGATGTA GGAGATGCTT GGGTTTCCAG GCAGCTGCCA GGGGTTAGGA
8251 GTGATTGCAG CTGTGGGTGT GGGGTGGGTG AGGGAGAGAC TAGCAGGCGG
8301 GGAGTGGGCT GAAGGCCATG CAGGTGGGGC CTCGGCTTCA CATCTTTTGT
8351 TAAATGGATT TTGTGGCTGT TACGACACTC TTGAGACCCA CATGTGAAAA
8401 CTGTCAGTCT GTTATCACTT AAGACAGAAG AAAATTGCCC TTGACTCTGG
8451 GCTGGCAGCA GGTGGAGACA AGGCCTGACA GCTTTCCTGC CATGTGGCAC
8501 ACACTTTGGG AGCAGAGCCA TAGCCCAAAG TGGACCGCCC TTGAGCTAGA
8551 AGTGTTGACT CAGGCGTGGG AAGGTGTAGA GCAGGCGGGT CACGGTGAGG
8601 AAGGAGTGGG GGGCTCAGTT GTCATGGGAG GTGCATGAAT TCGTACTGCA
8651 GAGTGGCTGC TCAGGGGTCT CCTGTGTTGA CATGTTATGT CAGGTTAAGC
8701 CATTTTAGCA TTCTTAGTTT TCTGAGGAAA CTCCACAGAA AGTTTTGCTT
8751 TATTTCTTAG AAGTAAGGAC AGATACCGGT TTCTCACCTG TCCTCTGCTC
8801 CTGTAGGCAC ATTGAGGATA AGTCCACCGT GTTTGGGACT GCGCTCAACT
8851 ATGTGTCTCT CAGAATTCTG GGTGTTGGGC CTGACGATCC TGACCTGGTA
8901 CGAGCCCGGA ACATTCTTCA CAAGAAAGGT ACGGCATGTG CAGCATGTGC
8951 TGGGCCAGGG GTTCGTGTCA ACTCGATAAT GAGCTCTCAC AAACGAGATA
9001 CAGAAAGATG CACTTGCAGC TGAAACAGTG GGCAAAAGCA CATGAGCAGG
9051 GAATTTGTCA AAGCAGAAGT AGGCAGACAC TGTTTAACCT AGGCATCATT
9101 TTTTAAAAAA GCAAATTAAG AGCCAGGCAC AGTGAGTGGC TCACGCCTGC
9151 AATTCCAGCA CTTTGGGAGA CTGAGGTAGA AGGACCACTT CAACCTAAGA
9201 GTTCGAGGCC AGCCTGGGCA ACATAGTGAG ACCTGGTCTC TACAAAAACA
9251 ATAAAATATT AGCCAGGTGT GATGATATGC ACCTGTAGTC TCAGCTACTT
9301 GGAGGCTAGT AAGGCAGGAG GATCACTTGA GCCCAGGAGT TCTGGGTTGC
9351 AATGAGCTGG TTGTACTACT GCACTCTAGC CTGGGTGACA GAGTGCGACC
9401 CTGTCTCTAA TAAAATAAAA AAGCCAAGCA AACTAAGACA ACCAGGTAAT
```

FIGURE 3, page 3 of 26

```
 9451 TCTGTTTGTT TCCTGAATTG GCAAAAACTT AAACGAACCG TGTTAATATG
 9501 TCCACCTTCT GGGGGGCAGC CTGGCTGCAG GCAAGAGCAG CCCTGGAGCT
 9551 TGCACCTTCC AAGCTGATCG TCTACCTCTC CAAGCCCGGG GCTGTCCACC
 9601 TCTCCAAGCC CGGGGCTGTC CACCTCTCCA AGCCCGGGGC TGTCCACCTC
 9651 TCCAAGCCCC GGGCTGTCCA CCTCTCCAAG CCCCGGGTTG TCTTACCTCT
 9701 CCAAGCCCCA ACTGTCTACT TCTCCAAGCC CTGGTCTGGC TACCTCTCCA
 9751 AGCCCTGGGC TGTCCACCTC TCCAAGCGCC AACTATCTTT CTCTCCAAGC
 9801 CCTGGCCTGG CTACCTCTCC AAGCCCCAGG CTGTCCACCT CTCCAAGCCC
 9851 CAACTGTCTA CCTCTCCAAG CCCCGGCCTG GCTACCTCTC CAAGCCCCTG
 9901 GCTACCTCTC CATGCCCGGC CTGGCTACCT CTCCTCTTGC CTATAGGCCC
 9951 TGAGGGGCAA TTCCAGCCCA AGGGAATCCA TGGCTCCTGC TGCTCCAAGA
10001 AAACCTAGTT TATGTTGTGG CTCTGCAGAG CCTGGCCTGG TCTTGTCCTC
10051 TGTGTTTCAC AGACCTTCCG TAGCCAGTCC CACCTGCCCT GCTCTCTGCT
10101 GCATGCGCAG GGGCCTCCTG TCAGCTCCTC AGAGACCCTT ATTATCCCAG
10151 GGCTCGCCAT GCACTGCCTC CTTCGCCTGG AGCCTCTTAC CTTCCACTCC
10201 TGCCCCGCTG GCTCACACTT TACGTGTTCC TTCTTTGAGG ACCTCTTCCT
10251 GACCTACCGT GCCAGGTGGA GTGTCCTGTT ACGCATTCTC ATGAGATCCT
10301 GCCTTCTTTC TTGGTGAGCT TGTCACTATT GTCCTCAGTT CACTGTCAGC
10351 CTTTGGTGTC GTTGATGCTG CGTCCCCAAG GCTGCTGTCC GGTTCCCACC
10401 ACACTCCTGG CGCCTGCCTG GTGAAGGAAC GTGTTTAGGC TGCACTTTGC
10451 CTAGTAGCTT TGTGGGTCTT TATTGACTTT TGCATACCTT TTGGGGTTTG
10501 GAGCAGGGAC TCCTCAGAAG CATGTTTAGA TGGTGTGGCT GTGCCAGGAC
10551 TGCTGCTGCT GAAGTGGCTC TGGCATGGGG CCAGCGTGCT GGAGCTACTC
10601 TGGAGTCTAG GGTCGTCTTT GTTCCCATAC AGGACCAGTC TGCCAAGTGG
10651 AGATGACACA GACTGGGGCA GCTCAGGCTT GGCTCAGAGG GCGAGGCTGA
10701 GTGTGCGCTG TCACTTCCCC ACCTTGCCTT CTCCAGGCGC ATGTGCACCT
10751 GGGCCCCTCG CTCACCTGAG CACTGAGGTG TCCCTGGACC TTCCCAGGTA
10801 GCTGTCTTCA TGTGCTCCTT CCTGGGGCCA GGGGTTGCAA ACACCTCTCC
10851 TGGGGCTGGA CACACACACT CCCAGGAAAG CCACTGGTTC CACCTAGGGG
10901 GCCGTGTATC CAGGCAAGTT CTCAGCACTC TGGAACCTGC TTCGCACATG
10951 GGGGTCGCAA GATCCACATG AGGCTGCCCT TGCCTCATGG AGAGGGGCAC
11001 ACGTGACTCC CAGAGGGTGA AGCTTCCCAG CTAGAGGCAG TGCAGACTTT
11051 GCTGACAGGA AGCAGATGAC GTGGGCCTAT TCTCTCCCCG CTCAGGTGGT
11101 GCTGTGGCCA TCCCCTCCTG GGGGAAGTTC TGGCTGGCTG TCCTGAATGT
11151 TTACAGCTGG GAAGGCCTCA ATACCCTGTT CCCAGAGATG TGGTATGTCT
11201 GCTGTTGATT GGGTTGTTGG GTCGCTGCTG CTGTCCCGGG GAGTAGAGTG
11251 ACAGGGACCG TGGGTCAGGT GCAGGCTGTG ACAGCAGAGA GGGGTGGGCA
11301 TTCTGTGGGT GGGTGGAGTT AGGCTCCTGG CAGAGGCCCT GATCAAGCTT
11351 GAGTCCTGTA GGGGTACAGA AAGGGGGAGG TTCCCAATTG AGCAGGAAGA
11401 AGGCTGTGCC ATGGATGGAG GTACCCCGAG TCAGGCTGCA GGCAGGGCTG
11451 GGTGGCTTCC CTCTTGCTGT GGAAGACTCA GCATCTGTAG AAGTGGGGGG
11501 GTGCCCCTCC CCCAGCCTGC ACAGGGGCGT CCTGTGTTGC TGCTGCTGCG
11551 TTTGTCTCCT TTGCTGGTGA ATGTGAAGTG TGTCCCGACG TGACACCTCA
11601 CCTGTGGACT CAGCGTGTGT GCCTTTAAAA GATCAGTGTC TGTGGCCAGG
11651 TGGGGTGGCT CATGCCTGTA ATCCCAGCAC TTCGGGAGGC CGAGGCGGGC
11701 AGATCACGAG GTCAAGGGAT CGAGACCATC CTGGCCAACA TAGTGAAATC
11751 CCGTCTCTAC TAAAAATACA AAAATTAGCT GGGCGTGGCG GCGCGTGCCT
11801 CTAGTTTCCA GCTACTCGGG AGGCTGAGGC AGGAGAATCA CTTGACCCTG
11851 GGAGGCAGAG GTTACCGTGA GCCGAGATCG TGCCACCATA TTCCAGCCTG
11901 GCGACGGAGT GAGACTCTGT CTCAAAAAAA AAAAAAAAAA GATCAGTGTT
11951 TGTTTTTTTA AACAGAACCA CATACTGTTT AAATACCCAG CAAAATCAAC
12001 ATTAATTTCT TATTATCTGG TGTGTGTTTT TTTTGTTTTG TTTTGAGACG
12051 GAGTCTAGCT TTGTCACTCA GGCTGGAGTG CAGTGGCGTG ATTTGGGGTC
12101 ACTGCAACCT CCGCCTCCCG GATTCAAGCA ATTCTCCTGC CTCTGCCTCC
12151 CGAGTAGCTG GGATTACAGT CTCAGGCCAT CACGCCCAGC TAATTGTTGT
12201 ATTTTTAGTA GAGACAGGGT TTCACTATGT TGGCCAGGAT GGTCTCAAAC
12251 TCCTGACCTC AGGTGATCCG CCTGCCTTGG CCTCCCAAAA GTGCTGGGAG
12301 CCATGAGCCA CTGCTCCCGG CCTTATGTGG TGTCTTTAAC CAGTGTCTTG
12351 TAACATTTTA TGGCTATCTA TTGAAAGCAG TGGACATCTC CCCAGAAAAC
12401 ACTCGTGCAT ATGAGTTTAC CCCGTTATGC ATTTTGGGAA GTGAGACCCT
12451 GGAACCACAC AGAGCCCCTG CTGGCTTCCT TGAGTGTTGT GGGAACCCTG
12501 GTGGGGGTGT CCCCTACAGA GCTATCATCA GGGCTGGGGG GGTCCCTTGT
12551 GTTAGATGAC TTTGGTGCGG GGGTGGGGGG TGGGGGGTCA AGTTAGGGGA
```

FIGURE 3, page 4 of 26

```
12601 GGCAGGAAGT GAAGGGGCCG CTCAAGAAAG GACAGCAGCA GTGTCCTGAT
12651 GCAAAGGCCG GGGGCTTAAC CCCGGAAGCC AGTTTGGGTG GTGACGGGGA
12701 GGCACAGGGA TGGTGAGATC ACCCCGGGAG GGTAGACAGA GATACCAGAG
12751 TAGGGGGCAG GGTTAGGGTG CCGCTACCTG AGGCGGGCCG TAGAGCACAT
12801 AGGTTGGGAG GTGTCCTGGG GCCATTCAAA TGCCCGCTGG ACTCTGCGCC
12851 TCGCCCGTGT GTAATGAGCG GCAGAGGAAG GACTGAGACG GCAGTCAGCA
12901 CAGCTGCCAG GGCAGGAGGG GTGTGGGTTC CACACGCTGG TGCTGGTGAG
12951 GGCGTCTCAT CTGCCCCACT TGGGGGGGCC GTCGGTCAGT GCTGCCGCAT
13001 GGGCACGCCA GGGTGCTGCT TGTCTTTGCT GGAGTTGCTT GGAGGGTGGG
13051 TTGGGAGGTG AAAGGAGGAC CACAGACCTG AACCACTCCA GCTGCGAAAT
13101 GCTGGAAGTG TAACCCAAAA TGTGAGAAAA AAAAACACCC TTTTAAGTAA
13151 GTGGGTGTGA AAGTGGGCCA AGGCCTGATG CCACAGTCAG GGAGCAGGGA
13201 AGGCTCAGCA TTGCTCACCC TCACTTAAGG ATGGGGCTAG CATCACATAA
13251 GGCATCACAT AAGGATGGGG GCTAGCAGGG AAAGGGAGAG AAAACACATG
13301 AGGCACACAC AGACCCTGGG AAGCTGGTGG AGCTGTGCTA ACGTCAGCAG
13351 ACCAGTGATC AAAGACCCAG GCCTTGGGGA GATTCCACAG ACCTACAGAC
13401 CTACAGTTTC TTTTTTCTTT CTTTTTCTTT TTTTTTTTTT TTTTGAGACA
13451 GAGTCTCTCG CTCTGTCACC AGGCTGTGTG CAGTGGCACA ATCTCGGCTC
13501 ACTGCAACCT CCTCCCAGGT TCAAGCGATT CTCCTGCCTC AGCCTCCCGA
13551 GTAGCTGGGA CTAGAGGCAC ACACCACCAT GCCTGGCTTA TTTTTGTATT
13601 TTTAGTAGAG ATGGGGTTTC GCCATGTTGG TCAGGCTGGT CTCAAACTCC
13651 TGACCTCAAG TGATCCACCA GCCTCGGCCT CCCAAAGTGC TAGGGTTACA
13701 GGCGTGAGCC ACCGTGCCCC TCCTAAAGTT TCTTAAATAC ACTTTTAAAA
13751 GTAAACTTTA AATTTTGGAG TAGTTTCCAA TTTCTGGAAA AGTTGCAAAG
13801 ATAGCCAAGA GTGTTCCCTG GGGCCCTCAC ACCATATCCC CATTGTTGAT
13851 GTTTTATGTT ACCAAGGTAC GTTTGTTGTA GCTAAGAAAC CCACGGACAA
13901 TCCTAAGCAT TTAGGAGCTC CATCACCTGG TTTTAGGATG CAAAATGCTG
13951 ACCGAACTAG GAGGTGCAGC TCCTCAGAGG GTGCACCTAT GGTTCAACTG
14001 TGCCCCTCAG GAGCACGGTT GGGAAATGCC CGCAGATGCA CTGACGTGGT
14051 GGGGAATAGC CATCCACCAG TGTTCGTGCT TGAAAGGGCC CAAGGTATGG
14101 ATGCTGGCGG AGGGGGCAGG CTTGAGTCTT GGGGTCTCCC ACTGACTCCT
14151 GCTGTTGCCC CAGGCTGTTT CCTGACTGGG CACCGGCACA CCCCTCCACA
14201 CTCTGGTGCC ACTGCCGGCA GGTGTACCTG CCCATGAGCT ACTGCTACGC
14251 CGTTCGGCTG AGTGCCGCGG AAGACCCGCT GGTCCAGAGC CTCCGCCAGG
14301 TAGGACCTCA TCAGGGAACA AAGTGAAGGC CTCTGGGGCT GGGACCCACA
14351 GGGCCTGGGG CTTCTGGAAT CTAACCACAC CTGTCCACTC ACCTGGTGGC
14401 CCTGTGGAGC GGAGAGCCCT GTGGAGCAGA GCCTCCACCT TCCTCCATCC
14451 TATAATAAAC AGTGAGCAAG CTCTGCCCAG AGGGGACTTG TGCTATGGGA
14501 CAGTCAGTAG CTGTAGCCCA GGGTTCCTGG GGGGGACTTC CAGGACTCAA
14551 GGGATGCAGG AGGCAGATGT GCACTGTGTC CTCTGGAAGC AGGCCTGAGG
14601 CGAGGTTTGA GGTGCAGGAT GTTTATCAGG CCTGCCATGG GGAAGAAGGA
14651 GGGGCAGAGG GAGGAAATGA GCTTCTGGGC AGACCTGGGA CTCATGGAGC
14701 TGGGGAGCTC CTCAGAGCGG TCCTCCCATA GGGGGCCTTC ATGTGCCCTC
14751 GGGGTCAGTT GCTGGAGGGA CCCCCACCCA GGAAGGGACT GGCCCAGGGC
14801 CCTGAGGGCG GATGGTGGGA GGCCACCCCT CCTGGTTTGA GCCAGGCCTA
14851 CCAGGTGCTC CCAGGCCCCA AGGCTCAGAC ACTGCCCCTA CCAGGAGCTC
14901 TATGTGGAGG ACTTCGCCAG CATTGACTGG CTGGCGCAGA GGAACAACGT
14951 GGCCCCCGAC GAGCTGTACA CGCCGCACAG CTGGCTGCTC CGCGTGGTAT
15001 ATGGTGAGCG CCTCCTGAGG GGCCGGCAGG GCAGCCCAGG GTCAGGGTCA
15051 GGGTGTCGCC CACTCATTCA CGCACTCATC CCCTGCCAGC GGCACTGGGC
15101 CACCTCCTCT GTGCCAGGCC CCAGGGGGCG GGATCTCATC GCCCTGCCCC
15151 TCCACCCTGA GAACCAGCTG GTCTTCTACT CTCAGGAGTC CACCCTGTGC
15201 AAGGGTGTGT GGTAGGAGGT GTGGGGCAGC CCCTCCTGGG CAGGGAAGGA
15251 GGAGCTCAGA GACCAGGCCT GGGGGTGGGT GGGAGGGGGA AACCCTGGGG
15301 AAGGGCAAGT CCAGGCGTTG CAGTGCATGG AGCTCCAGGC TGAGGCCAGT
15351 GTCATGGTGT CTGGCATCCA CTGACCCCTG TCCCCTGTAG CGCTCCTCAA
15401 CCTGTATGAG CACCACCACA GTGCCCACCT GCGGCAGCGG GCCGTGCAGA
15451 AGCTGTATGA ACACATTGTG GCCGACGACC GATTCACCAA GAGCATCAGC
15501 ATCGGCCCGG TCAGTGCCCC TGCCCGGCCT CTGACTGCAG CCCCTGGGGG
15551 TTGAGGTCCG AAAGTGAAGT CCTAGAGGCC GGGCTGTGAG CTGGGAGTGG
15601 GGTTTCCTGG AGCCTGGTGT ACCTCCATTT GGGAGGTGGC CCTCTGATCG
15651 CACAAGTGTC TGAGGGCTTC TGTCCTGGAC CCCTGCACGC CCAGCTCAGT
15701 GAAGTTGCCC CACCACACTC GACCCCCCGC TTCCGTCCCC CACCGGCTCT
```

```
15751 TGTCCTCAGT GTGCCTGGAC ACTCTCCTAG AGGCCCCTCC CTGAGATCTT
15801 GCTGGCTAGC TGGCTAGCTG GGAGGGGTGC TTTTTCCTCA CTTGGTTCCC
15851 TCTCCCCAAA CAGTTCATCA TTCGCCATTC TCCCGTGGGG TTTAGACATG
15901 CCCAGGGTGG GTGGGAGTAG CAGGTGCCAC TCCTGATTCC TCCTGCCTAG
15951 CTAGGGACTT GGAGCTCTCA CCTCTGTGGG GCCTGCAGGG GTCCAGGTGT
16001 GGCCAGTTCA GTGACCTTAG AGGGTGCAAT CCCCGGGCTG TGCTGGTGCG
16051 TGGCCGCCTC CTGACAGAGT CAGCAGGCCC TGGGCTGTGC TGCAGCTGCT
16101 GCCGTAGCTG TGCGCGTAGC TGCTGCGGTG TAGTGGGTTG GCTTAGGCAT
16151 TCTCTGGACA TACCCAGGTG GCACTGGGCC ACTGAGTCCC ACCCTGACAC
16201 TGCATCTCGG ATTTTCTGGG CCTCATGCCA CCTCAGTGGA TCACAAATCC
16251 TGACTGACCC TGCAGCGGGT CCCTTGTTTT TTGCTCAGCA GTGATGTGGT
16301 TCTTTGTGGG TTTTGGTTTA ATCCCATATA GAGCACATCT GTACTAAACG
16351 CATTAGAAAC ATGCTTGCAA TTGGATCTTG ACTTGTGAGA TGCATAAGTA
16401 AAAAGTTGGG GGCCTCTGGA ACATTCTGTT CTGAGGAAGA AGGGGGGCAA
16451 GTGGTCCCTA CTGCTACAGT CCTGTCTTCG CATCTCTTCC TGGGCCCCTC
16501 AGGCCCTGTC CTCTGTCCCC TGTGTTGTCT CTAAGGCACC TGGTAGCCCA
16551 TGCCCCTCTG GTTTCTCCTG GAACCCCTCG CTTCTCCCTG GTGGAGTGCT
16601 GCTCCTTCTC ACAGCCTAAG GCAGGCTGTG GCCTTGGCCG ACACTGCCTC
16651 TGTCTGAGTT GGGTCCTGGG GACACAGTTG TTGCCCATCC TCGCTCAGGA
16701 AATGCCTGTT AGAGCAGAAG GCCCCTGTCC TGGCCCTGAG TGATCTGCAC
16751 GGCACTTTAT GCCTGGGGGC TGCTGTGGAT CTGGACGAGA CCTTGTCCCT
16801 GGAGGCTGCT GTGGGTCTGG AGCGGAGCCT TGACAGGGCT GTCTCTCCTG
16851 CAGATCTCGA AAACCATCAA CATGCTTGTG CGCTGGTATG TGGACGGGCC
16901 CGCCTCCACT GCCTTCCAGG AGCATGTCTC CAGAATCCCG GACTATCTCT
16951 GGTGAGTGTG GCTGGGATAT GCTGGCGGGG CCTCTCACGA AGACTGGATC
17001 TGAGCCCCAG CTGCATCCCA GTGAGGGGGC CCCCACGGTG CCATCTGGGA
17051 ATACTGCCAG GGAATACCTC CAGGAACCAG CAGTGTCAGG GCTTGTGGAA
17101 GCCACTGAGG GTTGTCTTTG AATTGGAAGA TTTGCCACCC AGTGGAAGTG
17151 TGGGGTGTTC CCAGAAGGTA GAGTGAGGAA GGGGGTGGTA GGTAGCAGGG
17201 CAGGTTCAGG TTGGCATCAG GAGGCCTGTG GACAAGGGGA GCTTGTCAGC
17251 CATGGACTGT GCCCTGGAGG TGGGGCCCCT GTCATGGAGG GCAGAGAGCC
17301 GTCCCATGGT GGGAAGCTTC CGCTGTACAG GCCTCTTCCT CTGGTGCCTC
17351 AGCACTGCAC GAGGGCGGCA GGGCTGGCAC AGCCTGGGGT CGGGGAGCCT
17401 CCCGCTGCCC CTTGCCTTGG GTGTGGCCCT TCTGGGTGAG TGTGTCCTGT
17451 TTTCCATAGA GTGTGGCCCT CACCCCCAGG AGCCCAGCAG CCCAGCTGGG
17501 GTGGCATCCA GGCCAGTGCC AGGCCTCGGG AGGGGACAGA CGGCCTCTCT
17551 GGGACCCTCC TGAGTGCAGG GTCTGGGTAG CAGCTGGGCT TCCAGCTTTC
17601 TCCTTGCACC TGACTTGGGC TTTTTTCTCC TCACAGGATG GGCCTTGACG
17651 GCATGAAAAT GCAGGTAAGG GCTGCGGGAC TGCGGCTGCA TGCTTCCTTT
17701 GCAATCATGT CTCCCCTTTA TTATTTTTCC TTTGGGGTTC AGAAATAACT
17751 CCTCCTGGAC CAGGTCCCGG CAGCGTGCGA CTAGAGGCTG AGTCAGTTGA
17801 GGCCTCTGGC CGTGTCCCTG TGGGTGCTGT TGGTCTCTGT GTGGGTGCCC
17851 ACCGTTCTCG ATGTCTGTCT GCAGCTGTCC TGTTTGCTTT TTGCCCTGAT
17901 GATCTGAGTG GGCTCAGCTG TGTAACGACA GACCCAGAGC TGCAGAAGCT
17951 CTCATCTTGT TACTGTGGCA GGAGGTGGCT CTGGTTAGTG GGGGCTTCTC
18001 CTCCATGCAC TCTTAATTTA AGGGGCTTCT TCTTAAAGGT CCTGGGTGGA
18051 CAGGACAGGA GCCTGGAGGA CCGTGGTGGC GTGTGGCCGG GCCTGGGAGC
18101 TCCCCGTGGA CTTGGCCTGA GTGGGCTGGA ACCCAGTCAT GAGGGGCACC
18151 AAGCACAAGG AGAGGGGAGG CCGGGTGGAT CCTGGCTGAC CCTGGTCCTG
18201 TCCTGGCTCT GGGGGCCCTG TAGACCGCAG TCCTGTCCGA CTGGGCTGAG
18251 CCTGCGCCCC TCTGTGCGTG TCAGAAGCCC AGACAGTGTT GCCCTGTGTC
18301 TTGTGGTCTA AGGAGGGTTA CGCCCTGCGG TGCCTGTCTT CTGTCCCCCA
18351 CCTGATTCAG TGTGGAAATG TGGAGTCTCC AGAGGTGTCC TGGGTGTCAC
18401 ATTTGGGATG GATACACGTG GGCCCAGCAC TGCCCGCCCC AGGGCTACCC
18451 TTGGTGCCAG GTGCCCCCAG CCACGAGCTT TTACCCAGCT GGCCTTGAGC
18501 TCCCCAGAGG CTCCCCGGAC ACTGTCCGTG TTTTGTGAAA AGGTTTTCAA
18551 AACACATGTA AAGTGGAGGT GAGTAGCAAG CCCTAGAGCA GGCCCTGGCC
18601 TCCCTGCCCC TCCCTGTCCC CTCCCTGCCC CTCCCTGCCC AGCGCTCCCT
18651 CAGCACCGAC TCATCAGTGC ACCTCAAGCT GATGAGGGCG TCTGTGTTTT
18701 GACAAAATTG CTCTGAGGTT GTCACACCCA ACAAACTTAT GACGGTTCCT
18751 GAGTGTAGTC CTCACGTTGT GGCTGGTGTT TGTGAATCAG GATTCAGGCC
18801 AGGCCTGCAC AGGCCTTCAG TTGTTGGTCT TTGAGCTCCT GTTAGTCCAG
18851 CCGTCTCTCG TGGTCTCTTT TCTCCTCCTG GAAGGTTTGT TCCTGAAGGG
```

FIGURE 3, page 6 of 26

```
18901 CTTCACATTG CAGATCTGAC TGGTTGCTTC TTATGTTCCC TGAGTTTTTG
18951 TAAACTGGCC AGGCCCTGAG GCTCGATCCC ATTGTGTTTC TTTGGCGAGA
19001 ATGCTTTTCT GGTGGTCCCT GCCTTGTCCC TCCAGTGCAC GATGTCTGGA
19051 TGCCTCTGCC ACACACCACC CCCTGCCCAG TCCCCATGTC TGTCTGGTCA
19101 GTGCCCAGCT CTGTCTCACT AGGGTTTGGT CACCGGCCCT TTGAACTGAG
19151 ACCAGGCTGT GTACCTGTGA GCCCAGCTCG GGGTGAGATT TGAGGTGGAG
19201 CCTTCCCAGC CCTGTGCAGA ATTCCCATCA CCTCCAGGTG TACTCAGAAA
19251 TGGGGATCAT TGGCCAGGTG CGGTGGCTCA CGCCTGTAAT CCCTACACTT
19301 TGGGAGGCCA AGGTGGGCGG ATCACAAGGT CAGGAGATAG AGACCATCCT
19351 GGCTAACACG GTGAAACCCC GATGCTACTA AAAAATACAA AAAAAATTAG
19401 CTGGATGTGC TGGCAGGAGC CTGTAATCCC AGCTACTCCG GAGGCTGAGG
19451 CAGGAGAATG GCGTGAACCC AGGAGGCGGA GCTTGCAGCG AGCTGAGATC
19501 ACGCCACTGC ACTCCAGCCT GGGCAACAGA GCGAGACTTC ATCTCAAAAA
19551 AAAAAGAAAT GGGGTCATTT CCAGGCATCA CCATGACTGA GGTGCGCCAC
19601 TGTCATTGGG TGAGAGCAGC TGGATGCTCT ATGTGTAGGT GCTGGAGCCT
19651 CTGAGGGATC GTCCAGTCCT AGAAGTGTCC TCAGAGGGAC ACTGTCCTGC
19701 CTGGTGGCCC ATGAAGAAAG GGAGGGCTCC CTGAGTCTCC CTGACGTGTG
19751 TCTGCCTGCA GGGCTCAGCC TTCTCTGAGG CCCTTGTCAG CCATGAGGGG
19801 TGCCCAGGGC TCAGAGCCTG AGGCTGAGCG TTGGCTGGGT GGGAGCCCCC
19851 ACACCTGGCC CTCAGGCGCC CATTGGATCC TGGAGGCAGT GGCTGGGAGT
19901 GGGAGGGGCT GCATCTGCTG CTGTAACACC ATCCTTTGTG TGTAGGGCAC
19951 CAACGGCTCA CAGATCTGGG ACACCGCATT CGCCATCCAG GCTCTGCTTG
20001 AGGTTCGTGG CTCCTTCTCT TTTCTCAGCC TCAGCTGACC TTCCTGTGCA
20051 CGTAAGCCCA CGCATCCACC TGAGGGCAGC ACTGCTGGCC ACACACTTGC
20101 CACTCCTCGA TACTTCCAGT GACCTGGGCT CTGGCCTCTG GCTTCAGAGG
20151 GTCGTGCTGT GGAGGGGGCG GCCTTGGCCA GCAGCCTTGG GTGTTGGGCT
20201 GGGTCGGGGG CCTTGGGAGG GCAGGGGCTG GAGGCTGTGT GAGAAGGGGA
20251 GTCTGGTGAA GGCTGTTTCT GAGAGTGCAG GCAGGAGTGG GACTCCAGGC
20301 TCTTCTTAGA ACTGGAACTG CTTGGGCCAG GCACGGTGGC TCACACCTGT
20351 AATCCCAGCA CTTTGGGAGG CCGAGGAGGG TGGATCACGA GGTCAGGAGT
20401 TCAAGACCAG CCTGGCCAAG ATGGTGAAAC CCCGTCTCTA CTAAAAGTAC
20451 ACAAAAATTA GCCAAGCGTG GTGGCGGGCA CCTGTAATCC CAGCTACTTG
20501 GGAGGCTGAG GCAGAGAATT GCTTGAACCC GGGAAGTGGA GGGTGCAGCG
20551 AGCCGAGATT GTGCCACTGC ACTCCAGCCT GGGTGACAGA GAGAGGCTCC
20601 GTCTCAAAAA AAAAAAAAAA AAAAAAGAAC TGGAACTGTT TGTTATGGGC
20651 ATTCTCGAGC CAGTACTGGA GAAAAACGAG AGTGGATTTT TATGCCGGTG
20701 GGAATGAGGT AGGTGGGATT CTGAAGGTGT TTCTGGAGAG CCCTGAGGGC
20751 TGGGCCACGC AAAGGGCCTG CCTACACAGG GTGCTGGAGA CCCTCTGGGC
20801 ATGGATGCTG GCCAGGCAGG GGGGTGCTGG CATCCATAAA TGGTCTCCTG
20851 CGCCCTTCCA TCTTCAGTCA TATCTCATGG ACTTTTGCTG TTTTGTCTTT
20901 AAAGGTAAGT GCAGCAGGAG ACCCTGGCAC TCTCTGGAGA TGTCTGCTGG
20951 TTTGATTCTG GTCCCCGGTT GGGGCAGGAT GTGGCCAGGA CCATCGGGAA
21001 ACCAGCGCAG CCATGCTGGC CGTGCAAGGG CAGCTGAGCC TCTCTGTCCT
21051 GCTGTCTCTT CCAGGCGGGC GGGCACCACA GGCCCGAGTT TTCGTCCTGC
21101 CTGCAGAAGG CTCATGAGTT CCTGAGGCTC TCACAGGTGA GGCCGGTGCC
21151 TGGGGCTCTG AGGGGGCTGA AGAGGGGGAT CAGGGCTGGG AGCTCCTGCA
21201 GGCAGAAGTG CCCACCTCAC CTCCACCCTG CCCTATTTCC TGCACTGGTG
21251 TTTCAGGGTC ACCCCCACCC TCCCATCCCC TCCCTAGCCC CTGCTCCATC
21301 CACCGGTCCT CCTCGGGCTG GCCTCACCTG GGGCAGTTCT CTGAGGCCTG
21351 CAGGGTGCTG GGGGTGCTGG CAGTTTCTGC GTCCTGCTCA TGTTGGAGCC
21401 ACTGTGTGCA AGGGCCAGGC ACGGGCAGGG GCTGTGTACC CTGAGCTGCA
21451 CAGCCTACAC GGCACCTCCA TGTCTCTGAA GCACCTTCTG CCCATGGAGG
21501 TGACGCCAGC CTGTGGACTT GCCCTCCTGA GACTGTTTGC AGCAAAAGCC
21551 CCGGTCCCTC CTGCCAGATC AGCTGCCCAC AGACCCTGCC CGAGCCCATA
21601 GTTTGACCTC AGTGTCTCTC ACACGTGCCT GCACCCCAGT CTGCAGCCAC
21651 AGTCATCCCA TACATGCGCC CCAACCTCCC GTGTCTCCCA CACCCTGTCC
21701 CGGCCACGGC CTCAGCCAGT GTCCCTCTGC CTGGAACCGC TGCCCCCCAG
21751 CCCCGTCTCC CTCCCTTCAG CTCTCACTAG GACATTGTTC TGCAGGGCTT
21801 CTGGGTCTTC CTGGCCTCTG TGTGGCCAAG GCTGGCACCC ATCTTGGGCT
21851 CAAGCAGAGG AGGGGCATTG TCCTGCTGTG CCTGGCCCAA TGGCGGCCTG
21901 CTCCTGCTCC TGCCTCCTGC CCAGGACTTG CTCTGGGTGA TGGGGACTTG
21951 GGGAGGCTGA CTGAACCCTA CGGCACTCCA GGCCTCTTCC CTTCTCACTG
22001 AGGTGAGAGA GGCAGCCAGA AGCTGAGGTT GTTCAGGAGG CATTGGGGGC
```

FIGURE 3, page 7 of 26

```
22051 GCCTGGCACA GAGCACACCC GCAGAGACCT GGGCCCCCTC CCTGCCTTCT
22101 GGCCGGTGGG GAGATCACAG GGGAGTCAGG TGCTGACTCC CAGTCCCGTC
22151 TGGGCTGGTT TGAGCCCTCG CTGGCCAGTC ACGTTTCCCA GCAGCTGTGG
22201 GTGGTGAGCT AAACAGGTGC AGGCCCTCGC GCGCCTCGCA GCACCAGTGG
22251 TGGCTGTGGC CGGCAGAGTA AGCTCCCAGG CACGTTCTGC CTCTCCAGTC
22301 CTGCCCAGTC TGTCTCAGCG ATGTCCCAGA TGGGGACGTC CCGTGGTGAC
22351 GTGTTCTCTG CTTCCACATT TGCCCTCGAT GCTGCCCAGG TCCCAGATAA
22401 CCCTCCCGAC TACCAGAAGT ACTACCGCCA GATGCGCAAG GTATGCGGGA
22451 GCCAGCCCCA TCCCTGTCCC GTCCCCCAGG GGAGGCCGCC CTCAGCAGGG
22501 TGGGTCCTTC CCTCTGAAGG GGGGGCTCCT CCCTGGGGGA CTCCTCCCTT
22551 GGCGTTTTTG GGTGTCCTGC TGTGGTGGAT GCCTGGCCTA GGGGCTCATG
22601 CTTCATGTTG CTGAGCTGCC TGGCACATGG AGGCACAGTT GGCTTGCACA
22651 CACAGCCGTG CCTCAGAGCA GTTCCAGTGG TCACGGCACA CACAGGCTTC
22701 AGAAGGACAG CCGAAGTGTA GCCAGTGTGT CCGGGGAAGG CAGAGGAAAG
22751 AAGTAGACCT CAGAGCCGGT GTGGGCTGTG ACCACAGGTG CAGACTGTGA
22801 AATTAGGCAT GGACCCAGCT GCTGCTGCCT GTTTACAATG GGGGTGGGGG
22851 GCACCTGGGC CCCATCCTGT CCGTCGTGAG ATCTGCAGGT GTTGAGGGTG
22901 TGAGCTGCAC CCCTGAGGGT CCCTGTGCTG GAAGCTGGAG GTCTGTCTGG
22951 ATGTACCCAG CTTGGGGCCC TGGCTGCACC CACACCTTTG GTGGCTGGGC
23001 CCCTGCCCTG ACCGGGTGCT CTGTGGTGGG GAGGGATGCG TGCGGCTGTG
23051 GGGAGGTTCT GAGAACTGGG GTGTGGACAC CCCCAGCCTG GAGTCATGGC
23101 TTGTGCTCTG CAGGGTGGCT TCTCCTTCAG TACGCTGGAC TGCGGCTGGA
23151 TCGTTTCTGA CTGCACGGCT GAGGCCTTGA AGGCTGTGCT GCTCCTGCAG
23201 GAGAAGTGTC CCCATGTCAC CGAGCACATC CCCAGAGAAC GGCTCTGCGA
23251 TGCTGTGGCT GTGGTAAGGC TGTGGTCCCA GCAGCCCCGT CCATACCTCG
23301 TGTCCTGCAG ATGAGCTGCG TGCTCACTTC CACTCCTGTG GGCTCCAGCC
23351 CAGCACACAG TCCGGCCAGG CCGTAGGAGC TTGTCCTTGG ATGGTGTCTA
23401 TATGTGGAGA ACTGTGAGCT CTGGCTGGAC CCCTAGGGGC CTTGCTGGGC
23451 TGTGTGCACA GGGCCCTGCA CTGCGGAGCT GGTGTCCAGC CCAGCCACCG
23501 ATACTTGGGG GAGCCGGCGT GGCCCCCAAG GTTTCTCTCT GGTGGTTTCC
23551 ACTGGGTGTC TGAAGAGGGA ATTTGTTGGT GTTGGTTTTG GTGCCACATC
23601 CTTTCAGCAC ATCTGGCTTT TGTGTGTGTT TCCCAGTGGA GACCCTGCCC
23651 TTTTCTGGCA GCACAGACTT GGTTTCTAAG TCATGGGCAC GTGTGGGGGC
23701 ATGTTCCCTG GTGGCTGTGC ATGGAGGCCC TGACAGATGA GGTTGCAGCT
23751 GCTGCTTGGG GCACCCGAGG GCTTGGTTAA CGTGGAAATC AGCTCTCCGC
23801 CCCCTGTTCC TGCCCCATCG GTTGTCAGCC CTAGTGTTGC CTCTAGAGAG
23851 TTCCGCTGTG CCCTGGGCGC CTGTGTGTGC TCAGCACATG GGCGAGTTCT
23901 AGGGTGCTCT CTGTGATTTC AGCTGCTGAA CATGAGAAAT CCAGATGGAG
23951 GGTTCGCCAC CTATGAGACC AAGCGTGGGG GGCACTTGCT GGAGCTGCTG
24001 AACCCCTCGG AGGTCTTCGG TGAGTGGTCG GCCAGCACTG CGGCGCGCAA
24051 ACCCGGGGCT GGCTAGCACT GTGGTACACA AACCTGGGGG CCAGCTTTTC
24101 CCCCTTGCCC GAGGCTGCAA GGGCCCAGGT TCACCGGCAG ATCTGTCTGG
24151 AGCCCTCCCT CAGCCCAGGC TGTTCTGCGC TCCTCCATCC CCCGGGGTGG
24201 CAGGATCCTT GTGTTGTGGA TAGGAGGGCA TCAGGTCAGA CCTAGGGGAC
24251 AGTGGAGGGT TCCAGTGAGA TCCACAGCCT GGGCTGGTTC CTGCTCAGTC
24301 CACAGGGCTT GTGTTCTGTG GAGGCTGCTG TGTATCCAGA GCGCCTGCAG
24351 GGAGGTGTCT TTGGGGACTG TGGGGACTGT GGGGACCCAT GCCATGGGCA
24401 GTAGGCTGCT GTGTGTGCAT GGTTGCCACC GTACTGGTCT TGGGGGAGGA
24451 TCTCAGCCCT GGTCCACCTC TGGGCACCTC ACATACCCGC CTTCCTGGTC
24501 CCCTCCACAT CACACATGGC TTTTTGGGGT GGGGTCGCAG CTTTCTGCTG
24551 TGTTCCCCTC ATCTTCGCTC TCAGGTAGCA CAGGTGTGTG TCCTGGACCA
24601 GCCGGCGTTT GCTCTGGAGG TTGGTCAGGG AGGCAGCGTC CGGGCCCGGG
24651 CTCACTGCAA CACTCTTGCT TGTTGTGGCT TTGCCTGAGC TGCAGAGCCT
24701 GGGCAGCCAG GGTGAAACCC AACACTTGGT TCTTCCCTCC CTTTCCCAGG
24751 GGACATCATG ATTGACTACA CCTATGTGGA GTGCACCTCA GCCGTGATGC
24801 AGGCGCTTAA GTATTTCCAC AAGCGTTTCC CGGAGCACAG GGCAGCGGAG
24851 ATCCGGTAAG GAGGGTCTCA GCCATTCAGT GTGGGCGCTG CCAAGTCGGG
24901 GGCCAAGACC CAGACGCATC ATTCTGTGAC ACGGCCCTGG TGGCCCATCT
24951 CAGAAGCGAA ACTCATGGAA ACATGCAAGA GGCTTCGGAT GTTGTGGAAT
25001 CCAGTCATAT GCCCTAAAGC ATACAAAATA TCTGTTAGGG GCTCAGAATA
25051 GCACAGTTAT GATACAAAAA TGGATTTTCT CTCTCTTTTA ATAATGTTAA
25101 GAAGACATCA CATACCTGAC TCCACCGGTG TCCCAGAAAC GGTTTTTAAG
25151 TAACCTTTCC TGTTGAAGGG TAGCAAGTAT TCAGAAAAGT GTACAGGTTG
```

FIGURE 3, page 8 of 26

```
25201 GTCTTCTTGA AGCAAACAGG AAGCGAACAG TGCCAGCATT AGACATGGTG
25251 ACACCACCAG AGCCCTCGGC CCGCCCCATG ACGGGGCCGC CCACATGCCT
25301 GCCAGGTCGT GGGTGTCTGT TGCTCGCTTT GGATCTTGTC TAGGTGGACT
25351 CCTGAGGTGT GGAATTCGTG TTGCCTTCTC CTGCTCTCCT GCTCTCCTGC
25401 TCGCGGTTAG TCAGGTGGCT CGGGTAACAG CAGCGTTCTC TCCCTCGGGC
25451 CTTCGGTTGA ACACAGAATG CCGCGCTATC CAGCTGCCTG TTCTCAGCAC
25501 CTGGGAGGAT TTCAGTCTGG GTTATTATGA AGCATCTACT GTGAACACTC
25551 TTGTACTTAT CTTTTGGGGG CACCTGGGTA CCCATTTCTC ATGGTCACGT
25601 ACCTAGGAGT GGCATTGCTG TGTTAGAGGG TACGTTATAG GGTATGTGAT
25651 TTTTGTAGGT TCTTCTTTAT CCTATCACGA TTACATTTTT TTACTTTTGT
25701 TCAACCTGGT GTAGACTCAC CTTGGTCACA ATGCACTGTC CTTTTTATAT
25751 ATTGCTAGAT TCAATTTGAA GAATATTTTG TTAGGATTTT AGCAACTCTG
25801 GTTACAAGAG ACGCTGGTCT ATAATTTTTT TTTCTTTATA ATGTTTTTGT
25851 CAGGTTTTCC TGTTAAGATG ATGCTGGACT TAGAAAAGCA GTTGGAAAAT
25901 GCTTTTAAAA TACTCTTTGG AAGAATTTAT GTAATATTCA TAATATTTCT
25951 GCCTTAAATG TTTGGGAAAA ATTACCGGAA ATGCCAGTTG GGCCTGGAGA
26001 TTTCTTTGAG GAAAGTTTTT AAATTAGAAG TTCAATTTCT TTCTTTCTTT
26051 CTTTCTTTCT TTTTTTTTTG AGATGGGTTC TAGCTCTCTC ACTCAGGCTG
26101 GAGTGCGGTG TAATTTCTTT AATAGTTTAT AGGACTGAGC AGATTTTCCA
26151 TTTTTGTATC AGTCTGGGGA GTCTTCCCAT TTCCACTCAG CTTTACACTG
26201 ATTCATGCAA AGTTGTTCAG TGTCCTCTTA GATGGCTCTG AGCCCAACGC
26251 TGACATCCTC CTCTTCCTTC TGAGAATCTT ATACTGATCT TTTGAAAAAA
26301 AAAAAATCTT AGTCTTTGAT TCTGTTTTTA AAGAGACTTT ATTTTTGGTT
26351 TCATCAATTT CTATTGTTTG TTATTTTCTT TCTTTCTTAA TTTTTTTGAG
26401 ATGGAGTCTT GCTCTGTTGC TGAGGTTGGG GAGCAGTGGC GTGATCTCAG
26451 TTCACTGCAA CCTCCGTTTC CGGGGTTCAA GCGATTCTCC TGCCTCAGCC
26501 TCCCGAGTAG CTGGGACTAC AGGTGCTGAC CACCATGACT GGCCAATTTT
26551 TTGGTATTTT TATTAGAGAC AGGGTTTTAC CATGTTGTCC AAGCTGGTCT
26601 TGAACTCCTG ACCTCAGGTG ATCCACCTTC CTTGGCCTCC CAGAGTGCTG
26651 GGATTACAGG TGTGAGCCAC CACACTGGCC TTTGCTATTT TCTTTCTCCT
26701 TTATTTTTCT AACTTGAATA CTTAGATATT TGATTTTCAG GCTTTTATTG
26751 AAATATGAAT TTGAGGCTAT AAATGAGTTT TGAGATATCA TTCAGTTAAA
26801 TGTGTGTTCT GGTGCTTGCT GTGGTAGCAC AGATACTAAA AGTGTTTTCT
26851 GTTTCTACTG TTCTTCTCTG GCCCATGAGT TATGTGGGAG TATGCTGCTT
26901 CATTTACAAT CTGAGAATGT TCTGGTGTGG TTTTTTTGGA AGCCGTGGAT
26951 GGAGCAGGGG TTTTCTTGTG CTTCACAGGT GCAGCTAGGA GGGCACTGTG
27001 TCCAGGGTCT TCTGTCGGCC TGGCGTGGCC CTTGGCCATG TGCTGCTCTG
27051 CGGCATGAGG TGGGCGTGAG TTGTCCTCAG CCACATTTAG AGAATTGGCC
27101 TTTTAAAAAA TAGATCATCT TTTAAAAATC ACTGTAATAA AAGTAAAGCA
27151 GGTTCTTTGC AAACAAGACT TGCAAAATAC AGAGAAGCGC AAAGAAGAAG
27201 CTAAGTCGCC CCTCCTCGCC CCTGAAGGAG AATCTGCTGT TGCTGTTTGG
27251 TCTCCACATT TCCATGGCGG CTTGCTGCCC CTTTCACGCC TGGCCCACTT
27301 TGTGCCTGGT GAGGTTTCTA AAAGCCCCAC CCTTGAGCGC GCTCCTCCAG
27351 CACGAGCAGT AATGGCACAG GTGTTGTGTC ATTTTACTCA GTAGCCTCTG
27401 GGTTATTTTT CAGTTTTCCT TGTTGTTTTT TAGCTTTTCC CCATTTTAAC
27451 CTTAACTGGT ATTTTCTTGT TAAATATTTA TTCATGACCA TTATTATTCC
27501 CTAGAGCCAC ATGGCTTGGG GTCCACCTGC CTGGGTCCGC CCCCATCCCT
27551 GCCCCTTCTG GCTGTCTGAC CTGGCCTGGT GACTTCTCTT CTCTGCTCAT
27601 CTCTCTCCCT GCCTGAGTGG GCAAGAGTAC AGCCTCACAG AGTGGTGGGA
27651 TTGTGTGAGA TGCCACAGGG AAGCACATGT CAGTTGTTGT CACTGTGTAG
27701 AACAATGAGT CCCGGATGTG GCCCGCAGGG GAGCAATGGT GACTTAATCG
27751 CGGGCTTCCT CTGCATTTCT TTGGTGACTT CCAAGCTAGA ACATTCTTTT
27801 TTTGTTTATT TGTTTGAAGC AGGGTCTCAC TCTGTTACCT AGGCTGGAGT
27851 GCAGTAGCAA AATCATGGCT CACCACAGTC TCAAACTTCC GGGCTCAAGC
27901 AATCCTCCCA CCTCAGCCTC CTGAGTAGCT GGGACTACAG GTGCATACCA
27951 TCACCTGTGG CTAATTTTTT AAATGTTTTG TATTTTTTAA ATGTTGCTCA
28001 GGCTGGTCTT GAACTGCTGG GCTCAAGCAA TCCTCCCACC TCGGCCTCCC
28051 CAAATGCTGG GATTACAGAG TGAGCCACCA CACCCAGCCA TTTTTAAAAT
28101 TTTCACCAGG AAGTTTTTTC TTTCATTTTT AAGCACAGTA AGTATTTGTG
28151 TATTATGTTA CAGATATTTT CCCCTCAATT TCTTTGTTCT TTTTATCTCT
28201 TTAGGGAGTA TGAACATAAG TTTTTAACTT TTAAATGGTT AAATATATTA
28251 GTGTGATTTT TATATTAAGA TTTTATTTTA TTTATTTTTT TTTTTTTTGA
28301 GACGGAGTCT CGCTCTGTCG CCCAGGCTGG AGTGCAGTGG CGGGATCTCG
```

FIGURE 3, page 9 of 26

```
28351 GCTCACTGCA AGCTCCGCCT CCCGGGTTCA CGCCATTCTC CTGCCTCAGC
28401 CTCCCAAGTA GCTGGGACTA CAGGCGCCCG CCACTACGCC CGGCTAATTT
28451 TTTGTATTTT TAGTAGAGAC GGGGTTTCAC CGTTTTAGCC AGGATGGTCT
28501 CGATCTCCTG ACCTCGTGAT CCGCCCGCCT CGGCCTCCCA AAGTGCTGGG
28551 ATTACAGGCG TGAGCCACCG CGCCCGGCCT ATATTAAGAT TTTAAACTTG
28601 CCGGGCGCAG TGGCTGACGC CTGTAATCCC AGCACTTTGG GAGGCCGAGG
28651 CGGGTGGATC ACAAGGTCAG GAGATCGAGA CCATCCTGGC TAACACGGTG
28701 AAACCTTGTC TACTAAAAAT ACAAAAATTA GCCGGGCGTG GTGGCGGGCG
28751 CTTGTAGTCC CAGCTACTCG GGAGGCTGAG GCAGGAGAAT GGCGTGAACC
28801 CGGGAGGTGG AGCTTGCAGT GAGCCGAGAT GGTGCCACTG CACTCCAGCC
28851 TAGGCGAGAG TGCAAGACAC CGTCTCAAAA AAAAAAAAAA GATTTTAAAC
28901 TTACCTGGAG AGTTTTTGAG ATACAGTTTG GAGTTGCAAG TTACTTTAAC
28951 ACTATTTATA TGGAATATTC TATTTTACTA GACAGACTTA AATTCTCCCT
29001 TAAATTCACA AATTTATAGA AAAGTTACAA AAATACTGAA AAGTGCTCCT
29051 GTTTACTCTG ACTAGAATTC TTTAGTGGGT GGCACCCTAC CCTGAGGGCT
29101 TCATGACCTG TCCTCCCACA TGATCCAGGC TCTACCCTCA GGGCTTCATG
29151 ACCTGTCCTC CCACATGATC CAGGCTCTAC CCTCAGGGCT TCATGACCTG
29201 TCCTCCCACG TGATCCAGGC TCTACCCTCA GGGCTTCATG ACCTGTCCTC
29251 CCACATGATC CAGGCTCTAC CCTCAGGGCT TCATGACCTG TCCTCCCACG
29301 TGATCCAGGC TCTACCCTCA GGGCTTCATG ACCTGTCCTC CCACGTGATC
29351 CAGGCTCTAC CCTCAGGGCT TCATGACCTG TCCTCCCACG TGATCCAGGC
29401 TCTACCCTCA GGGCTTCATG ACCCTTCCTC CCACATGATC CAGGCTCTAC
29451 CCTGAGGACT TCATGACCTG TCCTCCCACG TGATCCAGGC TCTACCCTCA
29501 GGGCTTCATG ACCTGTCCTC CCACATGATC CAGGCTCTAC CCTCAGGGCT
29551 TCATTACCTG TCTTCCCACA TGATCCAGGC CCATTCTTTC TTGAACCATT
29601 GGAAAGGAAT TTGCAGATAG GATGTGTACC CCTAACTGCC TGAGTATTTC
29651 TTAGCAGGTG TATTCTTTTG TGCAAGTGTA AGTCAGAATG TTAATGTTGA
29701 TGAAATACTA ATCTGCAGGC CTAATTGTTC CAATAATGTC CTTTATGGCA
29751 AAATCTTCCC CTCAAGCTTT AATCCAATAT CATGGGTTGC ATTTGTTTAT
29801 TTTTAATTAT TTTTCTTTTC TTTTTCTGTT TTCCTTACCC TTCTCACTGT
29851 GCACATGGGT TGCATTTAGT TATCACATTG ACACCCTTTT AACCTGGAAT
29901 AATTCCTTAA TCTTTCCTTG TGTTTGATGA CTTTGTCATT TTTGAATTGT
29951 TCCACAAGTT ATTTTGTAGA ATATCCTCAG TGTTTTTTTT TTTCTGGTGT
30001 CTCGTGATTA GATTCAGGTT ATGAAACTAC ATTTTTGTCA GGAAGATTGC
30051 AGAAGAAATG GGGCCTTCTC CTGCACCTTA CCAGGAAGCA CACACCAACT
30101 TTGATCCCTT GATTAAGGTG ATGACCGCTG TACTTAGTTT CTCCGCTATG
30151 AAGTTGCTTT TTTTTTCTTT GTGGGGAGAC AGTTTTAGAC TATGTAAACG
30201 TCCTATTTCT CATCATACTT ATACCTGTTA GTGTTAGCAT TTGATGATGA
30251 TTCTTGCCTG AATCAATTAT TTGCATAATG CTTACAAAAT TATCATTCCT
30301 TCCATATGTA TTAGTTGGTG TTCTTCCAAA AGCTTTTCCT TTGCCTCTGT
30351 TTATTTACTT ATTTATCACT GTGGACGCAT AGATTCTTAC GCAATTGATT
30401 TTGATACTGA TCTCATAGCT AGACAATTTT GCTAAACTTT TAAAAAAATT
30451 TATGTACTTT ATCTTTTATA GCAGCTTTAA ATTTACAGAA AATTTGAGTG
30501 GAAGATGCAG TGTTCCCATA AAGCCGCTAA CTCCTCGCAC CTTCCCTCAA
30551 GTTTCCCCAG TACTAACATC TTGCATTCAA GTGGTGCGTT TGCAACATTC
30601 ATAAATTATT ATCGTCCAGA GTCCATTGTT TACATTCAGC TTCCTCTTCA
30651 TGTTGTTCAT TCTGTGGTTT CACAGATGTG TGATGCATGT GCCCACCACT
30701 GCAGTGTCAC ACAGGATCTC ACTGCCCCGG AGTCCTCTGC GCTGTCCCCG
30751 CCTCCAGAAC CCCTTAGTAG CAAACACTGA TATTTTTACT GTCTCCATAG
30801 TTTTGCCTTT TCAGACTGAC CTATTTCACT TAGTAAGAAG CATTTAAGAT
30851 TCCTGAGTCT CTTTCTATGG CTCAATAGCA CATTTCTTTT TAGTGCTGAA
30901 TAATATTCCA TTGTCTGGAT GTACCACAGT TTATTCATTC ACCTACTAAG
30951 GTGAATGTCT TGCTTGCTTC CAAGTTTTGG CAACTATGAA TAAAGTTGCT
31001 ATCAATGTTA GCGTGCACAT AAGTTTTCAG CTCATTTGGG TAAATGCCAA
31051 GAAGCATGAT TGCGGGATCC TATGGTAAGA GTGTGTTTAG TTCTGTAAGA
31101 AGCTGCCAAA CTGTATCTTA AGTGGCTGCA CCATTTGCGT TTCCACCAGC
31151 AATGATGAGC GTTTTGTTGC TCCACATCCT CACCAGCATT TGCTGTTGTG
31201 TTTTGGGTTT TAGCCTTTCT AAGAGGTGTG TAGTGGTATC TCCTTGTTTC
31251 AATTTGCAAT TCCCTAATGA CATTATGTTA AAATCTTGTC ATATAGTTAT
31301 TTGCCATCTG TGTATCTTTT TCAGTGATGT GTCCTTTAAA GTCTTTGGCT
31351 CATTTTTAAA TTAAATTTTC TTATTGTTGA GTTTTAGTTC TTCATATATT
31401 TTGGCTGCCA GTCCTTTATC AGATATGTCT TTCGCAAATA TTTTCTGCCT
31451 GTGTCTTGTC TTTTCATTCT ATTAACAGTA TCTTTTGCAG AGCCAGTTTT
```

FIGURE 3, page 10 of 26

```
31501 CATTTCAAGG AAGTCCAGCT TATCAATGTT CTCTTTCATG TATCATGTTT
31551 TTGGTGTTGT ATCTAAAAAG TTACTGCCAA GCCCAAGGGT ACCTAGATTT
31601 TTTCCTGTGT TATATTCTAG GATTTTTAAA GTTTTGCATT TTACATCTAG
31651 GTCCATGATT CATTTTGAGT TAACTTTTGT GAAGGGTTTA TGGTTTGTGT
31701 CTAGATTTTT TTTTTTTTTT TTTTTTTGCA TGTGGATGTC CAGTTGTTTT
31751 GGTACCATCT GTCAAGAAGA CTCTTTTTGG GTCATTTTGT TGCCTTTGTT
31801 TCTTTGTAAA AAATCAGTTG ACTGCATTTG CATGGGTCTA TTTCTGAGCT
31851 CTCTGTTCCA TTGCATTGAT CTGTTTGTTC TTCTCAGCAA TCCCACACTG
31901 TCTTGGTTCC TGTAGCTCTG TAGTAGGCCT TGCAGTCAGT TACCGCCCCT
31951 GTTCTCACTT CAGTGTTCTC TTCAATAGTG TTTTGACTAT TCTAGGTTTT
32001 TTCCCTCTCC ATATACATTT TAGAGTCAGT TTGTCAATAG TTTACAAAAT
32051 AACTTGCTGA GACTTTGATT GGGATTACAT TGAATCTGTA GCTCAAGTTG
32101 GAAAGATCTT TTATTTCTTT CATCAGAATT TTGTAGTTTT CATCATATAT
32151 AGATCTTGTA CATATTTTGT TGTTTATACC TAAGGATTTC ATTTTTTTGG
32201 TGCTAATGTA AATGGCGTTG TGTTTTAAAT GTCAAAATCT AATTGTTCAT
32251 TGCTGGTAGG AAAACAACTG ACCCTTTTTT TTTTTTTTAA GGGACGCAGT
32301 CTTACTCTGT TGCCCAGGCA GAGTGCAGTG GTGCCATCAT AGCTCACTGC
32351 AGCCTCAAAC TCCTGGGCTT AAGGAATCCT CCTGTCTCAG CCTCCTGAGC
32401 AGCTAGGACC ACAGGCATGT GCCACTACGT TCAGCTAATT TTTCAATTTT
32451 TTTGTAGAGA TGGGATCTTG CTCTGTTGCC CAGGCTGGTC TCAAACTCCC
32501 GTCTGCTTTG AGATGATTAT ATATTTGTGT CCTTTGTTAA TTTAGAGGAT
32551 TATTATGGAT TTTTCTAATG TTAAGACACC TTTGTATTTC TGAGATCGAC
32601 CTTAGTATTG GTCTATATTT AAGACAGTAT TCAGTTTCTC AGTTGTTTTT
32651 TGTTTTTTGG TTTTTTTTTT TGAGACAGAG TCTCTGTCTC CCAGGCTGGA
32701 GTCCAGTGGC ACAATCTCAG CTCACCGCAA GCTCTGCCTC CCGGATTCAC
32751 GCCATTCTCC TGCCTCAGCC TCCCGAGTAG CTGGGACTAC AGGCGCCTGT
32801 CATCATGCCC AGCTAATTTT TTGTATTTTT AGTAGAGACG GGGTTTCACC
32851 ATGTTAGCCA GGGTGGTCTC AATCTCCTGA CCTCGTGATC TGCCCACCTC
32901 GATCTCCCAA AGTGCTGGGA TTACAAGGCG TGAGCCACTG CGCCCGGCAG
32951 CAGTTTCTCA GTTTTAATTT GGAGTTTTGC ATCTGTGTTC ATGAGTGAGC
33001 CTGAAATTTT CACTTTTCCA TATCTTATTT CTCTGGGTTC CTAGAATGAG
33051 CTAGAGAGTG TTCCTCCTTT CTGTTCTCTG GAAGAGTTTG TGTGAGATTA
33101 GAATGAGTGT GTCTGATAAT TTAGTTGCAT TCATTTATAA AATTCCTAGG
33151 CCTAGAGTTT TTTTTCTGGG AAAAGTTTAC ATTTTGACTC ATTTTTTTAG
33201 TAGTTTTAGG ACTGTTTAGG TTCTCTATTT CTTGATTGAG CCAGTTTTGA
33251 TAAGTTAATC TTTCTAATTT GTAGATATTT TCTCTAAGTT TGCAAATGTA
33301 ATACATAAAA CTTTCTTGTC ATTTCTCACC ATATCTGTAG TTCTATCTTT
33351 TTATTGCTAA TATTACTAAT TTGTACTTTG ACTATTTGTA TTTGTTACCT
33401 GTTGCCGAGT AACAATATTA GTACAAACCT AGTGGCTTAG AACAACACAC
33451 ATTGATTACT TCACCGTTTC TGTGTGTCAG AAGTCCAGGC GCGGCCTCGC
33501 AGGTCGTCCT CTGCCTCAGG GTCTCTCCGG GCTTCAGTCA GGGTGTTAGC
33551 CAGGACCGGG GTCTCGCCTG AGCTTCCAGT GAGGAAGGAT CTGCCTCTGA
33601 GCACACAGGG TCCTCGGCAC GATCCCATTC CTCAGCTGGA AGCTGCCGAC
33651 TGCCGTCTGC TGCGGGGCCT CTCTAGATGG CATCTTCACA AAAGCGAGAA
33701 GGGAGAGTTG GTAGAGGGAG TCTGCTAGCA CCATGGGAGT CGCGGTCACA
33751 CAGACCTCGG TCCCAGGACC CGCACCCATC AACCCTGCCG TGATCTGCTG
33801 GTTAAAGACA AGTCCCACGT CCCACAGGGT GACACTGGAG TAGACACTTC
33851 GCTCTGGCCT TTTCAGAGAA CTGGTTATTT TTTGGAAATA TCAGTTAGAT
33901 GTAGGATGGG TCTTGTCTTC TAAATCTATT GTTTTCTCTC TAATTGATTT
33951 TTTCCTGTTT TTATTTAGTT CACTTTGTTG GGTTTGCTCA AGCCTGGGTC
34001 ACTGGATCTC AGGGATGCTG CTCCTGTTTG CAGCTGTGTC TGCAGGGGCT
34051 TCCCAAGGCC TTGCTTTCCC CTCACGTCCC TTTCTCAGAC TCTGCCAATC
34101 CGCTTCCCGC TCTGGTGTCC TGTGGTTGCT TCTTTTTAAA ACCCTCATCG
34151 GTCTGTGTAA ACTGTTTATT TTTATGTGGT TTTTAAGGGA GACCATTCTC
34201 ATTCTTTTGA GACCCTGGAA AGGATGGAAT TGGGATAGGT AAACTGCTGT
34251 TTTACCAGAA TGTTCACTGG ACCAATCTCG TGTTCCAGGG AGACCCTCAC
34301 GCAGGGCTTA GAGTTCTGTC GGCGGCAGCA GAGGGCCGAT GGCTCCTGGG
34351 AAGGGTGAGT GAGCCTCCAC TCGTGAGTGC AGAGATGCAT GGGATCCAGA
34401 GGTTTCTGCT CTCACACACT GCGTTCATAA ATGTTGGCTT GTATGTTGTT
34451 GCTACACCAG AAGTTTCTGG AAGTGAGCTG CCAGCCCCGTG ACTTCTGGGG
34501 GACCTCGTTC CTTTGTGGCA TGCGTGGCCT TTGCCCCGGT GGAAATTGCT
34551 CAGTACGTTG CTGGGCGCAG CCGGGCTGCT GGGAGCGCGC TGTAGCCTGA
34601 GCGTGGCTAT TCCCTCCACC CTTTCTGCTT GCTCTTAGGG TCCAGCAGAC
```

FIGURE 3, page 11 of 26

```
34651 AGAGCTGCTG TCTTCCACGG CCTTAATGCC TGAGGCACTG GAGTTGGTGG
34701 GCTGGCTGGG GCACGTGTGA TTGTTGCAGA ATGCGTGTTG TTTCACACAC
34751 CGGCTGTGAA CAGGGTGGAA GGGCTGAGGC TCTCCCTGTT TCCCTCCAGC
34801 TCCTGGGGAG TTTGCTTCAC CTACGGCACC TGGTTTGGCC TGGAGGCCTT
34851 CGCCTGTATG GGGCAGACCT ACCGAGATGG GTGAGTGAGT GCCTGTCCTC
34901 TGGTGGGTGG GGGTTCTCAA CCCAATGCTC TGTCATGAGT GTTTTTTGCT
34951 TTGACATTTG GTTTTAGGGT TTGTTTGTTT GTTTGTTTGT TTTTGAGACG
35001 GAGTCTCGCT CTGTCAACCG GGCTGACATG CAGTGGCATG ATCCTAGCTC
35051 ACTGCAGTCT CAAACTCGTG GGCTCAAGCG ATCCTCCCGA GTAGCTGGGA
35101 TCACAGGTGC ACGCCACCAC CCCGGGCTAA TCTTTTAAAA CTTTTATGTA
35151 GAGATGGAGT CTTGCTGTGT TGCTCACACT GGTTTGGGCT CAAGCAGTCT
35201 TCCTACCTCG GCCTTCCAAA GTGCTGGGGT TACAGGCATG AGCCAATGTG
35251 CCTGGCCTGT TTTTAATATT TTTAAACAGT GAGATAAGAT CCCCGGTTGA
35301 AATGAAGATG TTTCCCTGGT CCCACAGCTC TCTGGAGCTT CCTGACATGT
35351 ATGCTGGAGG GACGCTTCTG GTCTCCGGCC CCTCCAGGCA TACAGATGCC
35401 TCCCAACCCT GAGTAGGAAG ATTAGGGTCC ACGGCCTCGC TGGAGCGGGT
35451 TAGAAGGCAG GAGATCTCCG GTCCCAGCCG TGTCTCCAGC CGCCGGACTC
35501 TCTCCCAGCC CTGTCTCCAG CTGCCCCACT GTCTCCCAGA GTCTGCCGTG
35551 TGGATGTTTA GAGGTGGGGA GCACCGTGCT TGGCTGAGTG CAGCTTGTGA
35601 GACGCTGCTC CCAAGCACTG CAGACCTCAC TCAGCCTGAC GCGTCCGTGA
35651 GGCCATCCTC GGTACTCGCA TGTCCCTTTG TCTTCCCAGC GACTCTGGGA
35701 GGCAGGAGTA TCTGTTCCCA GTTCACATCT GCAAAAGTCA AGCTCGGGTT
35751 TCAGTAGTGG CCCATGGCCC TTAGGTAGGG TGGCCCCATC GTGCAGGCTC
35801 CTCCCCGTAC CCCAAGGCAG CCTGCTGGGG TGAGAAGCCA GGGGTCTGGG
35851 ACCTTCCTTG GTGTGATGGT GTCTCCTGTC TCTGGTCTTT GCAGGACTGC
35901 CTGTGCAGAG GTCTCCCGGG CCTGTGACTT CCTGCTGTCC CGGCAGATGG
35951 CAGACGGAGG CTGGGGGGAG GACTTTGAGT CCTGCGAGGA GCGGCGTTAT
36001 TTGCAGAGTG CCCAGTCCCA GATCCATAAC ACATGCTGGG CCATGATGGG
36051 GCTGATGGCC GTTCGGTGGG GACGACGGGA CCGTCCCTGA GCCTTGGGTT
36101 TGGGTAGAGG AGGGACACTC AGCTGTGAGC CGGTGGCCTG GGCTGAGTGA
36151 ATGTAGAGAG GAGGGGAGGC CTGTGGGCCA GGTCAGCTGC CACTCTGGGA
36201 ACAGACACCT ACAAGAGCCA CATGCCTGGT TCCTGGGGCA AGAACGTGGG
36251 CTGCTCTGAC CAAGTGGGGC CCTGCAGAGA GGCTCGCCTC TTAGAAGTGA
36301 ACCACCCACC ATTAGCCATG TCAGTGGAAG AGCAAGCACA TCAGGGACCC
36351 ATGGAAACAG CGAGGTGGGC TGCGATGAGG ATGCTGCTTC CTGGTGTGGT
36401 AGTGATGACG GTCACAGCAG CTGCTCTCTG TGGCCCTACT GTGTTCACAG
36451 CTGGTGCTGA GCCACATATG TGCCAGGTGC ACACACACGC AGACGCATGC
36501 AGGCAGGCAT CAGTGTACAC ACTGATGTGC ACACACAGAT GTACATGGAG
36551 ACAGATGCAC ACACAGGCCT ATGCACACAC GTACGCATGC CCACACAGGC
36601 ACCTGTGTCC ACACACATAC AGATGCACCC ACAGCATCCC ATCTGTGCCA
36651 CACACTGACA TAGGTACATG GAGACAGATG CACACACAGG TCTGTGCACA
36701 CACGTATGCA TGCACAGGCA CCTGTGTACA CACACGTACA GATGCACCCA
36751 CAGGATCCCA TCTGTGCCAC ACACAGACGT AGGTACATGG AGACAGATGC
36801 ACACACAGGT CTGTGCACAC ACATACATAC GCATGCACAG GCACCTGTGT
36851 ACACACATGC AGATACACCC ACAGCATCCC ATCTGTGCCA CACACAGACA
36901 TAGGTACATG GAGACAGATG CACACACAGG TCTATGCACA CACATACGCA
36951 TGCACAGGCA CCTGTGTACA CACACGTACA GATGCACCCA CAGGATCCCA
37001 TCTGTGCCAC ACACAGACGT AGGTACATGG AGACAGATGC ACACACAGGT
37051 CTGTGCACAC ACATACATAC GCATGCACAG GCACCTGTGT ACACACACGC
37101 AGATACACCC ACAGCATACC ATCTGTGACA CACACAGACG TAGGTACATG
37151 GAGACAGATG CACACACATG TCTGTGCACA CACATACATA CGCATGCACA
37201 GGCACGTGTG TACACACATG CAGATACACC CACAGCATGC CATCTGTGAC
37251 ACACACAGAC GTAGGTACAT GGAGACACAT GCACACACAG GTCTGTGCAC
37301 ACACATACGC ATGCACAGGC ACCTATGTAC ACACATGCAG ATACACCCAC
37351 AGCATCCCAT CTGTGCCACA CACAGACATA GGTACATGAA GACAGATGCA
37401 CACACAGGTC TATGCACACA CGTATGCATG CACAGGCACC TGTGTACACA
37451 CATGCAGATG CACCCACAGT ATCCCATCTG TGCCACACAC AGACATACGT
37501 ACATGGAGAC AGATGCACAT ACAGGTCTAT GCACACATGT ACACATGCAC
37551 AGGCACCTGT GTACACACAT GCAGATGCAC CCGCAGTATC CCATCTGTGC
37601 CATACACAGA CATACGTACA TGGAGACAGA TGCACATACA GGTCTATGCA
37651 CACATGTACA CATGCACAGG CACCTGTGCA CACATATGCA GATGCACCCG
37701 CAGTATCCCA TCTGTGCCAC ACACAGACAT ACGTACATGG AGACAGATGT
37751 ACACACAGGT CTATGCACAC ATGTACACAT GCACAGGCAC CTGTGTACAC
```

FIGURE 3, page 12 of 26

37801 ACATGCAGAT GCACCCGCAG TATCCCATCT GTGCCACACA CAGACATACG
37851 TACATGGAGA CAGATGCACA CACAGGTCTA TGCACACATG TACACATGCA
37901 CAGGCACCTG TGCACACATA TGCAGATGCA CCCGCAGTAT CGCATCTGTG
37951 CCACACAGAC ATACGTACAT GGAGACAGAT GTACATACAG GTCTATGCAC
38001 ACATGTACAC ATGCACAGGC ACCTGTGCAC ACATACATAC AGATGCACCC
38051 GCAACATCCC GTCTGTGCTG CCCTATTAGG TTTGTGGCCA TTTGGGGAAT
38101 CTTCCTAAAA CCCTAAAAGC TAGGGCAGGT CTGCTTGAGC AGGAGCAGCA
38151 GGGTCTGGGG GACCCCTGAG GGCAGGACAG TCAGGGACCC ACAGTTGAGC
38201 TGGGCCCGCT GAGCCCTGGA TCCTTCTTGG TGTCTTATCC TGGCCAGCAA
38251 GCAAGTGTGA GCTCCTGTGG GTCTCCAGAG GCCCATGAGG ACCAGTGGGC
38301 CAGTTGGGAA CAAGGCTTGG CGTCCTCTTC AGGGGGGAAC ACCAGGGCAG
38351 GCCTGAGGAG GCCTGTGTCC CCAGCCTGTC ATTGCTGTGG CTCCGCTTCT
38401 CAGGGAGCCT AGGAAGAAGG TGTGGCAAGA GCCCGAGGCG CTGGCTGCAC
38451 CTGGCGGGGC CTGTGGGCGT CAGTTTAGAC CCATCCATTC TCACTGCAGC
38501 ATTCCAGGGT TTGCCCTTAT GCTCGGCTGT GTGAGGGTGA GGATGATGCT
38551 GTGGGGGCAT GCATGCTGGG TGTGTTTCAG CCTTCTCTTC CACCAGGCAT
38601 CCTGACATCG AGGCCCAGGA GAGAGGAGTC CGGTGTCTAC TTGAGAAACA
38651 GCTCCCCAAT GGCGACTGGC CGCAGGTATG CCGCCAGGGA CCTGAGCGCA
38701 CAAGGCCCAG CACTGACCTC CAGCGTGCAT GGCTGTTTCC ACGTCCCCCT
38751 GCTCTGTGTC CTTTTTGGGG TACTTTGGAC ACTTGGGAGG CGTCACCTCT
38801 GCCAGTGAAT GCCACAGTTG GTGGCAGGTC TGTGGCAGGT GGTCGGGTCC
38851 TAAAGTCCAG ATCTTGCTGT TGTTTCAAGT GATGCTCTGG GTGGGGGAGG
38901 AGCTGGATGG GAGAAGCCAG TGGGCGGGAA GCCTTTTTGC TGCAGGACAG
38951 ACCCTCCCAC TCCAGATGAC CTAGTGGCCC CTCACTGAGC CAGAAGTCCC
39001 TGTGGTGTGG GTGTCATGAG GTCATGTGAG GCCAACCGCC CTCCCCTGGG
39051 ATGAGGCTGA GTTGGTGGAA GCTGATGTGG TTGTGAGGGG CTGGTGACCC
39101 TGGCTTAGGG TTTGCTGCAG GGCGGGGAGT CTGAGCTGGG CTGATGGTGC
39151 CATGACTGAT GCGGGATGGA CTACTTGCTT TCCTATGCTC TTGCTTAATT
39201 AGCCCTTTCC AGGCTGACTC ACCCACAAGC CAGCCAAGCC AACAGCCAGG
39251 GCTCCAGTTC AGGGACTAGC CCTCAGCTGA CTGGTGAAGC CTTTGTGTTT
39301 ATTTCTCTGT GTTCTTTTAG GAAAACATTG CTGGGGTCTT CAACAAGTCC
39351 TGTGCCATCT CCTACACGAG CTACAGGAAC ATCTTCCCCA TCTGGGCCCT
39401 CGGCCGCTTC TCCCAGCTGT ACCCTGAGAG AGCCCCTTGCT GGCCACCCCT
39451 GAGAACATGC CTACCTGCTG GGTGCCGTCT GTGCGTTCCA GTGAGGCCAA
39501 GGGGTCCTGG CCGGGTTGGG GAGCCCTCCC ATAACCCTGT CTTGGGCTCC
39551 AACCCCTCAA CCTCTATCTC ATAGATGTGA ATCTGGGGGC CAGGCTGGAG
39601 GCAGGGATGG GGACAGGGTG GGTGGCTTAG ACTCTTGATT TTTACTGTAG
39651 GTTCATTTCT GAAAGTAGCT TGTCGGGCTT GGGTGAGGAA GGGGGCACAG
39701 GAGCCGTGAC CCCTGAGGAG GCACAGCGCC TTCTGCCACC TCTGGGCACG
39751 GCCTCAAGGT AGTGAGGCTA GGAGGTTTTT TCTGACCAAT AGCTGAGTTC
39801 TTGGGAGAGG AGCAGCTGTG CCTGTGTGAT TCCTTAGTGT CGAGTGGGCT
39851 CTGGGCTGGG GTCGGCCCTG GGCAGGCTTC TCCTGCACCT TTTGTCTGCT
39901 GGGCTGAGGG ACACGAGGGC AACCCTGTGA CAATGGCAGG TAGTGTGCAT
39951 CCGTGAATAG CCCAGTGCGG GGGTTGCTCA TGGAGCATCC TGAGGCCGTG
40001 CAGCAGGGAG CCCCATGCCC CTGGGTCGTG AGCTTGCCTG CGTATGGGGT
40051 GGTGTCATGG AGCCTCATGC CCCTGGGTCG TGAGCTCGCC TGAGTATGGG
40101 GTGGTGTCAT GGAGCCGCAT ACCCCTGGGT TGTGAGCTCG CCTGCATATG
40151 CAGGGTCTGT CATGGAACAT CCCAAGTCTG TGCAGCAGGG GAGCCCCATG
40201 CCCCTGGGAC ATGAACCCAC CTGCGTGGAA TGCTGTTTGT GAGGTGTCTA
40251 CAGGGTTTAT AGTAGTCTTG TGGACACAGA AATGCACAGG GGACACTTAC
40301 GGACACAGAA ATGCACAGGG GAGGCCGAGC ATAACCAGGG GTGAGGGGCA
40351 GGCAGCAGTT GTAGTTACTG CCGCGGGGCA CTGCTATGTG CAGGGACAGC
40401 CAGCGCCCAG CCCATCACCA CTCCCTGGGC TGGCTGGCAG GTATGGCACC
40451 CTGGGAGCCC GGCATATACC CAGGGCACCC CTACGGCTGC CGCCAGTCTC
40501 ATGCCCAGGT GGGTGCTCTG GGCTGGAGCG AGGGCCAGGT TTTGGGCCGA
40551 GGCTTCCCCA GGCAATCCTG TGAGCTCCCT TCTAGCCTCT GACCCAGTCT
40601 GGTCTGGCTT GCATGGATGT AGGGCTTGGG GTGGGAAGTT CAGGTCCTGG
40651 CTTTGCCTTT GCCTGATGTG GATGAGCAGC TCACATGCTC AGGGCCACCT
40701 GAGACTGTCA CTGCTCTCCC CTGGCTACTG GGAGGAGTCA CTGAGAGCTT
40751 CGTTACCCCT GCTGCCTTGC CCAGGGCACA CCCTATACCT CCTCATCTGC
40801 TCTTCCCCTC CCTGCCGCCT TCTGGGCAGG TAGCAGTCCC TGGCCTCTCC
40851 CCCTGGCTGA TCACTCTCCC TCAGGCAGTG GAGATCTGCG TCTGGACACC
40901 CTCAGATCCT GTCATTGCCT GCCCAGAGTC CTTCAGGGGC ACCCCTCTGC

FIGURE 3, page 13 of 26

40951 CTTGGTGTGC GGTCCAGGGC TCTCACCCAG GTGCCGCACC CTCTGGGGTC
41001 TTCTGTCCAG CTCCCTTGCC CCATGTGCTG TCACTGACTC TCCTTGGGAC
41051 TCGCCTGCCT GCTCAGAGCC CTGCAGGGCT TGGTCAGCTG CCTGTTCAGT
41101 GTCAACACTT CCCTGCACAT CTTAAAACTG GGCTTTATTT TCGCTGAAGG
41151 AACTGTGTTG GGACCCTTGA CATCTGTCAG GTTTGCACAT GCTGTTTTTT
41201 TTTCTCAGCC CACGTGTTCT CCCCCACGTG GGGTAGCAGC AGGACAGACA
41251 GTGAATCACA GAGTCTGCCC TGAGCAGAGG CTGCTGTCCC TGGGACTCCT
41301 AGCCATGGTC AGACTGTACA AAACGGTTTT CCAGAAATGA AATGTAAATC
41351 CATTTTTATA CTGAAAATGT TACTGAAAGT CACTTTTATG AGCATCTGCC
41401 TTAATAAACA GACATTGATT CCCTTATCAG AAGCCTGTCA CACTGTGTTT
41451 CGTTTCATCC TGGGGAGAAC TGCAGATTTG GGGTTTCTGG CTGTCATACG
41501 TCACCTGCCT GTGGGGCGAG TGGGAGGCCC AGCCTGGTTT AGGGAACAAG
41551 AGTGACGTGA GGAGTAGCAG GGTGCGTCTC CAGTTACCTG AGGGAAAACA
41601 GATATTTTAA GAGATAATAG CATAGCCTAT TTTAATATGT TTTAAAGGCC
41651 ATAAGCATAT CCAGGAAGAT AAATAAACGT GATACAATGT CCACATAGGA
41701 GGAACTTTCT TTCACTGCAT TGTTTTCCTT CACAGTGGCC TTCAAGTCAC
41751 AGGACGCAGC GATTCCCTGC CCTCTTCGGT GTTATTACAC AGGCAGGACT
41801 TCAGTGTCAG TATCCCTGCC TTCAGTCTTC TTTAGAAATC ACATCTGTGT
41851 TCAATCCATT GTTTAGAGGG AGTGTATTTT TCCTGTTCCA CGAAGAGGAC
41901 TTTTTGTTCA CAATTGGATC ACAATGCAGA GGAGTCTGTT CCTCCCCCGT
41951 CGGCTTCTCG GTGCTGGGAG GGTGACCTGT CCCAGATGAC TCATCACCCT
42001 GACATGCTCT TGACAAAGGA CACCACCAAG AGGAGATGGC AGCTGTACCG
42051 GTGCAGCCTC TGTCTGAGGG GGATATTTGC CTCAGTGTGA TTAAAAATCA
42101 GTCATGAAAG ATTTTTGAAT TCAGATTATT TTTATCAGGA ACAGATTTTG
42151 AACATCCTGA AATCTTTTCC CTGGCATCAT ATTAGGTTTT CTTTGTTCAC
42201 TATGATGTAA AGTTTCAGAC TCTTGATATT TTTAATATCA ACATAGACGG
42251 TAGGACAAGG AACGGTACCA GAAATGAGTA AAGAGACAAT AATGATAAGA
42301 TCGATTTATC AAGACATAAC AACCCCAAAT GTATATGCAC TAAATAACAG
42351 CTTCAAAATA CATGAAGCAA AATGGCAGAA TTGAAGAGAA TGAGATAAAA
42401 ACAGAATTTT AACGGGTGCT TTCCGTACTT TGTAACTGAC AGACATGAGA (SEQ ID NO:3)

FEATURES:

Start: 2034
Exon: 2034-2047
Intron: 2048-2179
Exon: 2180-2345
Intron: 2346-3088
Exon: 3089-3227
Intron: 3228-8043
Exon: 8044-8119
Intron: 8120-8806
Exon: 8807-8928
Intron: 8929-11095
Exon: 11096-11192
Intron: 11193-14163
Exon: 14164-14299
Intron: 14300-14894
Exon: 14895-15003
Intron: 15004-15390
Exon: 15391-15509
Intron: 15510-16853
Exon: 16854-16951
Intron: 16952-17636
Exon: 17637-17664
Intron: 17665-19945
Exon: 19946-20002
Intron: 20003-21064
Exon: 21065-21136
Intron: 21137-22389
Exon: 22390-22440
Intron: 22441-23113
Exon: 23114-23263
Intron: 23264-23922

Exon: 23923-24019
Intron: 24020-24749
Exon: 24750-24855
Intron: 24856-34288
Exon: 34289-34354
Intron: 34355-34799
Exon: 34800-34880
Intron: 34881-35894
Exon: 35895-36065
Intron: 36066-38596
Exon: 38597-38675
Intron: 38676-39320
Exon: 39321-39449
Stop: 39450

CHROMOSOME MAP POSITION:
Chromosome # 21

ALLELIC VARIANTS (SNPs):

| DNA Position | Major | Minor | Domain | Protein Position | Major | Minor |
|---|---|---|---|---|---|---|
| 478 | - | A | Beyond ORF(5') | | | |
| 891 | C | G | Beyond ORF(5') | | | |
| 948 | - | C | Beyond ORF(5') | | | |
| 3311 | A | T | Intron | | | |
| 3616 | T | C | Intron | | | |
| 3910 | G | A | Intron | | | |
| 6028 | G | A | Intron | | | |
| 8299 | G | A | Intron | | | |
| 8373 | C | G | Intron | | | |
| 8424 | A | G | Intron | | | |
| 8680 | A | G | Intron | | | |
| 8700 | C | G | Intron | | | |
| 8996 | A | C | Intron | | | |
| 10590 | T | C | Intron | | | |
| 11090 | G | C | Intron | | | |
| 11710 | G | A | Intron | | | |
| 12591 | G | A | Intron | | | |
| 13431 | - | T | Intron | | | |
| 14746 | C | G | Intron | | | |
| 14975 | G | C | Exon | 277 | P | P |
| 16031 | C | T | Intron | | | |
| 16891 | - | T | Exon | 339 | | V |
| 19359 | C | T | Intron | | | |
| 19405 | A | G | Intron | | | |
| 19653 | G | A | Intron | | | |
| 19742 | T | C | Intron | | | |
| 20054 | A | G | Intron | | | |
| 20627 | - | A G | Intron | | | |
| 21337 | T | C | Intron | | | |
| 21894 | C | T | Intron | | | |
| 23360 | G | T | Intron | | | |
| 26758 | A | C | Intron | | | |
| 27033 | T | C | Intron | | | |
| 27332 | C | A | Intron | | | |
| 27538 | C | A | Intron | | | |
| 27625 | G | C | Intron | | | |
| 27736 | A | G | Intron | | | |
| 30688 | T | C | Intron | | | |
| 31172 | C | T | Intron | | | |
| 31433 | C | T | Intron | | | |

FIGURE 3, page 15 of 26

| | | | | | | |
|---|---|---|---|---|---|---|
| 32660 | G | T | Intron | | | |
| 32981 | A | C | Intron | | | |
| 33557 | T | C | Intron | | | |
| 33652 | G | A | Intron | | | |
| 34390 | T | C | Intron | | | |
| 34399 | G | C | Intron | | | |
| 34989 | G | - | Intron | | | |
| 35067 | C | G | Intron | | | |
| 35495 | G | A | Intron | | | |
| 36001 | T | G | Exon | 631 | L | V |
| 38948 | C | T | Intron | | | |
| 39160 | T | C | Intron | | | |
| 40405 | G | A | Beyond ORF(3') | | | |
| 40794 | C | T | Beyond ORF(3') | | | |
| 40961 | A | G | Beyond ORF(3') | | | |
| 41891 | C | T | Beyond ORF(3') | | | |

Context:

DNA
Position

478
AGGTTCAGTGTGAGATTCCATCCAGGCTGAAGCCCCTTATCCCTATTCTTCATGTTTCTA
CATGGAGGAACTTACCTGGAGAAAAACTTCCAGCCTCTTTCTGCTTCCAGAGAAGTAGAG
TGACTCATTTGATTGAATTTCAGAGAACAGATAGGGTGGAGTGTGCTCAGGCTCCTCTGG
GTACTCTTTCTGGGGTCTGTGGGTTGACTGGAGGGGTGTCTTCTGGTGGGCACTCAATTG
CATAGTGCTTGGTGAGGCAGTTTCATGGCCTAGAGGCTGGGGATATGTTTGTCTGACTT
[-,A]
CGGGTGATTTAGTAGCTTGCCCTCTTGCTTGCAGATTTAAGCCTTGTCCTTCAAGCTAGG
TTTTTAATTTGTGGCAAAGCTGATATTTTGATACCCACCCATCTTATTGCTGTGTCTTTT
TCATCCGTTTCTGAACTGGGATAGGAAGAGGTGATTATCCTTGATTGTCTAAAACCCCGC
TATTCCACTGTGGGGAAGGTGCCTGTGGGTATTCTTTTGTCCACTCTCTCTTCCAACTTT
CTCCTCCGGCTTGCTGTGGCTCACCGCCCCTTCGAAGTTAGGCTGGGGGTAGGAATTGAG

891
TGTCTTTTTCATCCGTTTCTGAACTGGGATAGGAAGAGGTGATTATCCTTGATTGTCTAA
AACCCCGCTATTCCACTGTGGGGAAGGTGCCTGTGGGTATTCTTTTGTCCACTCTCTCTT
CCAACTTTCTCCTCCGGCTTGCTGTGGCTCACCGCCCCTTCGAAGTTAGGCTGGGGGTAG
GAATTGAGGAGTGGGTGCCGAAATGCTCACTAGGCTGGGGCAGTTGTAACTGGATGTCAG
GGCTTCTGTGGGCCAGGTGAAGACATGCTGGGGTCTTCTGTGGGTCCTTGACCTGACTTA
[C,G]
GGACCACTGGCTGCAGCCTCCAGACGTCAGCCATGTTTCCAACAGTCAGACGCCCCCTGC
CCTGTTGCGCCCGGCTGTCCCTTCCAAGTTCGGTCACTCGCTCTGCCTCCATCTTCCTCT
TCCCTCTGCTGCTAAGGCTTTTCACCTTTAATTTCTCCTGGGGCCACCCCCAACTCCAGC
GACCCCGTGAGCAGCTGAGGCTCTACCGCGCTCGGTCCTGGCCAGCGACGCAGCCCTTCC
CTGGCGGGGCTCCAGGGCTTCTGGCCCCTGTGGTCCGCCAGGTGTGGGGGCCCACGGCCT

948
TAAAACCCCGCTATTCCACTGTGGGGAAGGTGCCTGTGGGTATTCTTTTGTCCACTCTCT
CTTCCAACTTTCTCCTCCGGCTTGCTGTGGCTCACCGCCCCTTCGAAGTTAGGCTGGGGG
TAGGAATTGAGGAGTGGGTGCCGAAATGCTCACTAGGCTGGGGCAGTTGTAACTGGATGT
CAGGGCTTCTGTGGGCCAGGTGAAGACATGCTGGGGTCTTCTGTGGGTCCTTGACCTGAC
TTAGGGACCACTGGCTGCAGCCTCCAGACGTCAGCCATGTTTCCAACAGTCAGACGCCCC
[-,C]
TGCCCTGTTGCGCCCGGCTGTCCCTTCCAAGTTCGGTCACTCGCTCTGCCTCCATCTTCC
TCTTCCCTCTGCTGCTAAGGCTTTTCACCTTTAATTTCTCCTGGGGCCACCCCCAACTCC
AGCGACCCCGTGAGCAGCTGAGGCTCTACCGCGCTCGGTCCTGGCCAGCGACGCAGCCCT
TCCCTGGCGGGGCTCCAGGGCTTCTGGCCCCTGTGGTCCGCCAGGTGTGGGGGCCCACGG
CCTCACCGCGCCTACCCCACTCCCCCGGCGAAGCTACGCGGCGCTCAGCTTCCCAGGGA

3311
TGTATGTGAAGAGGGTTCCTCTGGCCGGGCAACAGTCCCGTCAGCTATCTCTTTTTTTTT
TTTTCGATCTCTTTGCAGAAGAATTACTTTAAGGACTTGCCCAAAGCCCACACCGCCTTT
GAGGGGGCTCTGAACGGGATGACATTTTACGTGGGGCTGCAGGCTGAGGATGGGCACTGG
ACGGGTGATTATGGTGGCCCACTTTTCCTCCTGCCAGGTAGGAGTATGCTGCCCCAGCCT
GATGGTATGGCCACCCTGGATCACCCTTGGGATCCTGGCCCAGCCTGGTCTAGGGTTTTG
[A,T]

TGAAGCAGGTGAAAATCCAGGGGCTCACAAGAAAAGGGCTGGCAAACTCTGCCCTATGTC
AGAGTCGTCCTGCTATTGGTCTAGGGGATCAGCTAGCCTTGCCAGTGTAGGGTGACAGGC
TCTCTGATAAGAGAAGCAAGTGGTTCTCTAGGGCTCTGTGTTGCCTTGAGGGAGGAGGAA
GGTGGGCTTTGAAGTCTCAGTACAGGATGGGATGGACATTCCAGGTGGAAGGCCCAGCCT
ATGCCAAGGGGCTGTAGGTGGGCAGAGTGGTGGGTGGGGAGCTGATATCTGCTGTGAACT

3616
GCAGGTGAAAATCCAGGGGCTCACAAGAAAAGGGCTGGCAAACTCTGCCCTATGTCAGAG
TCGTCCTGCTATTGGTCTAGGGGATCAGCTAGCCTTGCCAGTGTAGGGTGACAGGCTCTC
TGATAAGAGAAGCAAGTGGTTCTCTAGGGCTCTGTGTTGCCTTGAGGGAGGAGGAAGGTG
GGCTTTGAAGTCTCAGTACAGGATGGGATGGACATTCCAGGTGGAAGGCCCAGCCTATGC
CAAGGGGCTGTAGGTGGGCAGAGTGGTGGGTGGGGAGCTGATATCTGCTGTGAACTTCCT
[T,C]
GGGGCTATTGCAGGAGAGCTTCAGGTTCAGGCTGGTGAGTAGGAGGAGCATAGCAGTTGG
ACTGCCTGGGTATTGAACTGATTTGGCTACACAAGACTATTTTGCATCCTGGGAGTGTTT
CTCTACAGAAATCCTCAGCCTTGTAAAATGGGAAATTCCCTCCTATGAATTTATGCAATA
GGACTTTTTTCCCTAGTGACTTGTAATCACATTGTTTCAATGACGTGAATTCCTACATAA
ATAGGTTTTGTTTCTGTGATAACTCTTACTGATACATCATTTTCTTTTACTACGCTGACT

3910
CTTCCTCGGGGCTATTGCAGGAGAGCTTCAGGTTCAGGCTGGTGAGTAGGAGGAGCATAG
CAGTTGGACTGCCTGGGTATTGAACTGATTTGGCTACACAAGACTATTTTGCATCCTGGG
AGTGTTTCTCTACAGAAATCCTCAGCCTTGTAAAATGGGAAATTCCCTCCTATGAATTTA
TGCAATAGGACTTTTTTCCCTAGTGACTTGTAATCACATTGTTTCAATGACGTGAATTCC
TACATAAATAGGTTTTGTTTCTGTGATAACTCTTACTGATACATCATTTTCTTTTACTAC
[G,A]
CTGACTTTGTAATAGATAGAAAGTCCTTATATACCTTTGTTGCCTTTCTTTTTAAAACAT
CTCTTACCTGTGTCTATTCATTTACTCATCCAAATTGCCTTTATCCTGATTTTGTCCCAG
ACTTGAAATGAAGTTGCAATAGGCTTATATGTTAGTTTGGGAAGAGTTGGCCTTTAACGT
TAAAAACAGTTCCATGGTGTTTACTGTAGGCCAAGCCCTGCTCAAGGCCTGTTCTTCTTT
TAGTCCTTAGAATAAGCCTAATGAGATACATTAGAAAGCTGAGGCACATTTATTCCAGGT

6028
GTCTCTTGCCTTGGCACCAAGGTGGCTTGCCACCCACAGCCTCTCGAGTAGCTGGGATTA
CAGCCATGTGCCACCATGCCTGGCTAATTTTTGTATTTTTGGTAGAGACAGGTTTTCACC
TTGTTGGTCAGGCTGGTCTCGAACTCCTGACCTCGTGATCCCCCACCCCCCACCCCCAGC
CTCCCAAAGTGCTGGGATTACAGGCGTGAGCCACTGCACCTGGCTGAGTTGGAGCTTTTC
TTCCCTCTTTTTGGACTTTGGAAAATGCTCTTGGTCCATGATGCTATGTAGACAGCTCCC
[G,A]
TTGACTGTGGCCTGTGCGGCATTGGGCAGCACTCTGGTGAACACTGAATCGGGTCTGACC
TCCTAGCCCCACCATTTACTGGCTGAGCCTCAGTTTCCTTGCCTGTAAAATCAGGAAGAT
GCTGGCTCTGCTCCTCTCTGCACATTTCCCCGTCCTAACAACATTATAACTGTTAGGAAA
GAGACGGGCTTGTTTTGGGATGGCTCATTTTATGTGACCCTGTGCGCTGTCTCTGAGTCC
ATCTGCCCTTCTTCCAGGGTGTAGGGACCAGCCCCACAGGGTCGGTGGGTCTCTCCCTGT

8299
CATGACCACCTGTCCCCAGTGAGGAACATCTCTCCTGCCACACAGGCCTCCTGATCACTT
GCCACGTGGCACGCATCCCTCTGCCAGCCGGATACAGAGAAGAGATTGTGCGGTACCTGC
GGTCAGTGCAGCTCCCTGACGGTGGCTGGGGCCTGTGAGTGTGCCTGCCCCTGTGTCACT
GCACATGTGCATGTGTGTGTTCTCATGATGTAGGAGATGCTTGGGTTTCCAGGCAGCTGC
CAGGGGTTAGGAGTGATTGCAGCTGTGGGTGTGGGGTGGGTGAGGGAGAGACTAGCAGGC
[G,A]
GGGAGTGGGCTGAAGGCCATGCAGGTGGGGCCTCGGCTTCACATCTTTTGTTAAATGGAT
TTTGTGGCTGTTACGACACTCTTGAGACCCACATGTGAAAACTGTCAGTCTGTTATCACT
TAAGACAGAAGAAAATTGCCCTTGACTCTGGGCTGGCAGCAGGTGGAGACAAGGCCTGAC
AGCTTTCCTGCCATGTGGCACACACTTTGGGAGCAGAGCCATAGCCCAAAGTGGACCGCC
CTTGAGCTAGAAGTGTTGACTCAGGCGTGGGAAGGTGTAGAGCAGGCGGGTCACGGTGAG

8373
ATCCCTCTGCCAGCCGGATACAGAGAAGAGATTGTGCGGTACCTGCGGTCAGTGCAGCTC
CCTGACGGTGGCTGGGGCCTGTGAGTGTGCCTGCCCCTGTGTCACTGCACATGTGCATGT
GTGTGTTCTCATGATGTAGGAGATGCTTGGGTTTCCAGGCAGCTGCCAGGGGTTAGGAGT
GATTGCAGCTGTGGGTGTGGGGTGGGTGAGGGAGAGACTAGCAGGCGGGGAGTGGGCTGA
AGGCCATGCAGGTGGGGCCTCGGCTTCACATCTTTTGTTAAATGGATTTTGTGGCTGTTA
[C,G]
GACACTCTTGAGACCCACATGTGAAAACTGTCAGTCTGTTATCACTTAAGACAGAAGAAA
ATTGCCCTTGACTCTGGGCTGGCAGCAGGTGGAGACAAGGCCTGACAGCTTTCCTGCCAT
GTGGCACACACTTTGGGAGCAGAGCCATAGCCCAAAGTGGACCGCCCTTGAGCTAGAAGT

FIGURE 3, page 17 of 26

```
        GTTGACTCAGGCGTGGGAAGGTGTAGAGCAGGCGGGTCACGGTGAGGAAGGAGTGGGGGG
        CTCAGTTGTCATGGGAGGTGCATGAATTCGTACTGCAGAGTGGCTGCTCAGGGGTCTCCT

8424    GTGCAGCTCCCTGACGGTGGCTGGGGCCTGTGAGTGTGCCTGCCCCTGTGTCACTGCACA
        TGTGCATGTGTGTGTTCTCATGATGTAGGAGATGCTTGGGTTTCCAGGCAGCTGCCAGGG
        GTTAGGAGTGATTGCAGCTGTGGGTGTGGGGTGGGTGAGGGAGAGACTAGCAGGCGGGGA
        GTGGGCTGAAGGCCATGCAGGTGGGGCCTCGGCTTCACATCTTTTGTTAAATGGATTTTG
        TGGCTGTTACGACACTCTTGAGACCCACATGTGAAAACTGTCAGTCTGTTATCACTTAAG
        [A,G]
        CAGAAGAAAATTGCCCTTGACTCTGGGCTGGCAGCAGGTGGAGACAAGGCCTGACAGCTT
        TCCTGCCATGTGGCACACACTTTGGGAGCAGAGCCATAGCCCAAAGTGGACCGCCCTTGA
        GCTAGAAGTGTTGACTCAGGCGTGGGAAGGTGTAGAGCAGGCGGGTCACGGTGAGGAAGG
        AGTGGGGGGCTCAGTTGTCATGGGAGGTGCATGAATTCGTACTGCAGAGTGGCTGCTCAG
        GGGTCTCCTGTGTTGACATGTTATGTCAGGTTAAGCCATTTTAGCATTCTTAGTTTTCTG

8680    CTTGAGACCCACATGTGAAAACTGTCAGTCTGTTATCACTTAAGACAGAAGAAAATTGCC
        CTTGACTCTGGGCTGGCAGCAGGTGGAGACAAGGCCTGACAGCTTTCCTGCCATGTGGCA
        CACACTTTGGGAGCAGAGCCATAGCCCAAAGTGGACCGCCCTTGAGCTAGAAGTGTTGAC
        TCAGGCGTGGGAAGGTGTAGAGCAGGCGGGTCACGGTGAGGAAGGAGTGGGGGGCTCAGT
        TGTCATGGGAGGTGCATGAATTCGTACTGCAGAGTGGCTGCTCAGGGGTCTCCTGTGTTG
        [A,G]
        CATGTTATGTCAGGTTAAGCCATTTTAGCATTCTTAGTTTTCTGAGGAAACTCCACAGAA
        AGTTTTGCTTTATTTCTTAGAAGTAAGGACAGATACCGGTTTCTCACCTGTCCTCTGCTC
        CTGTAGGCACATTGAGGATAAGTCCACCGTGTTTGGGACTGCGCTCAACTATGTGTCTCT
        CAGAATTCTGGGTGTTGGGCCTGACGATCCTGACCTGGTACGAGCCCGGAACATTCTTCA
        CAAGAAAGGTACGGCATGTGCAGCATGTGCTGGGCCAGGGGTTCGTGTCAACTCGATAAT

8700    ACTGTCAGTCTGTTATCACTTAAGACAGAAGAAAATTGCCCTTGACTCTGGGCTGGCAGC
        AGGTGGAGACAAGGCCTGACAGCTTTCCTGCCATGTGGCACACACTTTGGGAGCAGAGCC
        ATAGCCCAAAGTGGACCGCCCTTGAGCTAGAAGTGTTGACTCAGGCGTGGGAAGGTGTAG
        AGCAGGCGGGTCACGGTGAGGAAGGAGTGGGGGGCTCAGTTGTCATGGGAGGTGCATGAA
        TTCGTACTGCAGAGTGGCTGCTCAGGGGTCTCCTGTGTTGACATGTTATGTCAGGTTAAG
        [C,G]
        CATTTTAGCATTCTTAGTTTTCTGAGGAAACTCCACAGAAAGTTTTGCTTTATTTCTTAG
        AAGTAAGGACAGATACCGGTTTCTCACCTGTCCTCTGCTCCTGTAGGCACATTGAGGATA
        AGTCCACCGTGTTTGGGACTGCGCTCAACTATGTGTCTCTCAGAATTCTGGGTGTTGGGC
        CTGACGATCCTGACCTGGTACGAGCCCGGAACATTCTTCACAAGAAAGGTACGGCATGTG
        CAGCATGTGCTGGGCCAGGGGTTCGTGTCAACTCGATAATGAGCTCTCACAAACGAGATA

8996    TAAGCCATTTTAGCATTCTTAGTTTTCTGAGGAAACTCCACAGAAAGTTTTGCTTTATTT
        CTTAGAAGTAAGGACAGATACCGGTTTCTCACCTGTCCTCTGCTCCTGTAGGCACATTGA
        GGATAAGTCCACCGTGTTTGGGACTGCGCTCAACTATGTGTCTCTCAGAATTCTGGGTGT
        TGGGCCTGACGATCCTGACCTGGTACGAGCCCGGAACATTCTTCACAAGAAAGGTACGGC
        ATGTGCAGCATGTGCTGGGCCAGGGGTTCGTGTCAACTCGATAATGAGCTCTCACAAACG
        [A,C]
        GATACAGAAAGATGCACTTGCAGCTGAAACAGTGGGCAAAAGCACATGAGCAGGGAATTT
        GTCAAAGCAGAAGTAGGCAGACACTGTTTAACCTAGGCATCATTTTTTAAAAAAGCAAAT
        TAAGAGCCAGGCACAGTGAGTGGCTCACGCCTGCAATTCCAGCACTTTGGGAGACTGAGG
        TAGAAGGACCACTTCAACCTAAGAGTTCGAGGCCAGCCTGGGCAACATAGTGAGACCTGG
        TCTCTACAAAAACAATAAAATATTAGCCAGGTGTGATGATATGCACCTGTAGTCTCAGCT

10590   CATGAGATCCTGCCTTCTTTCTTGGTGAGCTTGTCACTATTGTCCTCAGTTCACTGTCAG
        CCTTTGGTGTCGTTGATGCTGCGTCCCCAAGGCTGCTGTCCGGTTCCCACCACACTCCTG
        GCGCCTGCCTGGTGAAGGAACGTGTTTAGGCTGCACTTTGCCTAGTAGCTTTGTGGGTCT
        TTATTGACTTTTGCATACCTTTTGGGGTTTGGAGCAGGGACTCCTCAGAAGCATGTTTAG
        ATGGTGTGGCTGTGCCAGGACTGCTGCTGCTGAAGTGGCTCTGGCATGGGGCCAGCGTGC
        [T,C]
        GGAGCTACTCTGGAGTCTAGGGTCGTCTTTGTTCCCATACAGGACCAGTCTGCCAAGTGG
        AGATGACACAGACTGGGGCAGCTCAGGCTTGGCTCAGAGGGCGAGGCTGAGTGTGCGCTG
        TCACTTCCCCACCTTGCCTTCTCCAGGCGCATGTGCACCTGGGCCCCTCGCTCACCTGAG
        CACTGAGGTGTCCCTGGACCTTCCCAGGTAGCTGTCTTCATGTGCTCCTTCCTGGGGCCA
        GGGGTTGCAAACACCTCTCCTGGGGCTGGACACACACACTCCCAGGAAAGCCACTGGTTC
```

FIGURE 3, page 18 of 26

11090 CTTCCCAGGTAGCTGTCTTCATGTGCTCCTTCCTGGGGCCAGGGGTTGCAAACACCTCTC
CTGGGGCTGGACACACACACTCCCAGGAAAGCCACTGGTTCCACCTAGGGGGCCGTGTAT
CCAGGCAAGTTCTCAGCACTCTGGAACCTGCTTCGCACATGGGGGTCGCAAGATCCACAT
GAGGCTGCCCTTGCCTCATGGAGAGGGGCACACGTGACTCCCAGAGGGTGAAGCTTCCCA
GCTAGAGGCAGTGCAGACTTTGCTGACAGGAAGCAGATGACGTGGCCTATTCTCTCCCC
[G,C]
CTCAGGTGGTGCTGTGGCCATCCCCTCCTGGGGGAAGTTCTGGCTGGCTGTCCTGAATGT
TTACAGCTGGGAAGGCCTCAATACCCTGTTCCCAGAGATGTGGTATGTCTGCTGTTGATT
GGGTTGTTGGGTCGCTGCTGCTGTCCCGGGGAGTAGAGTGACAGGGACCGTGGGTCAGGT
GCAGGCTGTGACAGCAGAGAGGGGTGGGCATTCTGTGGGTGGGTGGAGTTAGGCTCCTGG
CAGAGGCCCTGATCAAGCTTGAGTCCTGTAGGGGTACAGAAAGGGGGAGGTTCCCAATTG

11710 CATGGATGGAGGTACCCCGAGTCAGGCTGCAGGCAGGGCTGGGTGGCTTCCCTCTTGCTG
TGGAAGACTCAGCATCTGTAGAAGTGGGGGGGTGCCCCTCCCCCAGCCTGCACAGGGGCG
TCCTGTGTTGCTGCTGCTGCGTTTGTCTCCTTTGCTGGTGAATGTGAAGTGTGTCCCGAC
GTGACACCTCACCTGTGGACTCAGCGTGTGTGCCTTTAAAAGATCAGTGTCTGTGGCCAG
GTGGGGTGGCTCATGCCTGTAATCCCAGCACTTCGGGAGGCCGAGGCGGGCAGATCACGA
[G,A]
GTCAAGGGATCGAGACCATCCTGGCCAACATAGTGAAATCCCGTCTCTACTAAAAATACA
AAAATTAGCTGGGCGTGGCGGCGCGTGCCTCTAGTTTCCAGCTACTCGGGAGGCTGAGGC
AGGAGAATCACTTGACCCTGGGAGGCAGAGGTTACCGTGAGCCGAGATCGTGCCACCATA
TTCCAGCCTGGCGACGGAGTGAGACTCTGTCTCAAAAAAAAAAAAAAAAAAGATCAGTGTT
TGTTTTTTTAAACAGAACCACATACTGTTTAAATACCCAGCAAAATCAACATTAATTTCT

12591 GTGCTGGGAGCCATGAGCCACTGCTCCCGGCCTTATGTGGTGTCTTTAACCAGTGTCTTG
TAACATTTTATGGCTATCTATTGAAAGCAGTGGACATCTCCCCAGAAAACACTCGTGCAT
ATGAGTTTACCCCGTTATGCATTTTGGGAAGTGAGACCCTGGAACCACACAGAGCCCCTG
CTGGCTTCCTTGAGTGTTGTGGGAACCCTGGTGGGGGTGTCCCCTACAGAGCTATCATCA
GGGCTGGGGGGGTCCCTTGTGTTAGATGACTTTGGTGCGGGGGTGGGGGGTGGGGGGTCA
[G,A]
GTTAGGGGAGGCAGGAAGTGAAGGGGCCGCTCAAGAAAGGACAGCAGCAGTGTCCTGATG
CAAAGGCCGGGGGCTTAACCCCGGAAGCCAGTTTGGGTGGTGACGGGGAGGCACAGGGAT
GGTGAGATCACCCCGGGAGGGTAGACAGAGATACCAGAGTAGGGGGCAGGGTTAGGGTGC
CGCTACCTGAGGCGGGCCGTAGAGCACATAGGTTGGGAGGTGTCCTGGGGCCATTCAAAT
GCCCGCTGGACTCTGCGCCTCGCCCGTGTGTAATGAGCGGCAGAGGAAGGACTGAGACGG

13431 AAAAACACCCTTTTAAGTAAGTGGGTGTGAAAGTGGGCCAAGGCCTGATGCCACAGTCAG
GGAGCAGGGAAGGCTCAGCATTGCTCACCCTCACTTAAGGATGGGGCTAGCATCACATAA
GGCATCACATAAGGATGGGGGCTAGCAGGGAAAGGGAGAGAAAACACATGAGGCACACAC
AGACCCTGGGAAGCTGGTGGAGCTGTGCTAACGTCAGCAGACCAGTGATCAAAGACCCAG
GCCTTGGGGAGATTCCACAGACCTACAGACCTACAGTTTCTTTTTTCTTTCTTTTTCTTT
[-,T]
TTTTTTTTTTTTTGAGACAGAGTCTCTCGCTCTGTCACCAGGCTGTGTGCAGTGGCACAA
TCTCGGCTCACTGCAACCTCCTCCCAGGTTCAAGCGATTCTCCTGCCTCAGCCTCCCGAG
TAGCTGGGACTAGAGGCACACACCACCATGCCTGGCTTATTTTTGTATTTTTAGTAGAGA
TGGGGTTTCGCCATGTTGGTCAGGCTGGTCTCAAACTCCTGACCTCAAGTGATCCACCAG
CCTCGGCCTCCCAAAGTGCTAGGGTTACAGGCGTGAGCCACCGTGCCCCTCCTAAAGTTT

14746 CATCCTATAATAAACAGTGAGCAAGCTCTGCCCAGAGGGGACTTGTGCTATGGGACAGTC
AGTAGCTGTAGCCCAGGGTTCCTGGGGGGGACTTCCAGGACTCAAGGGATGCAGGAGGCA
GATGTGCACTGTGTCCTCTGGAAGCAGGCCTGAGGCGAGGTTTGAGGTGCAGGATGTTTA
TCAGGCCTGCCATGGGGAAGAAGGAGGGGCAGAGGGAGGAAATGAGCTTCTGGGCAGACC
TGGGACTCATGGAGCTGGGGAGCTCCTCAGAGCGGTCCTCCCATAGGGGGCCTTCATGTG
[C,G]
CCTCGGGGTCAGTTGCTGGAGGGACCCCCACCCAGGAAGGGACTGGCCCAGGGCCCTGAG
GGCGGATGGTGGGAGGCCACCCCTCCTGGTTTGAGCCAGGCCTACCAGGTGCTCCCAGGC
CCCAAGGCTCAGACACTGCCCCTACCAGGAGCTCTATGTGGAGGACTTCGCCAGCATTGA
CTGGCTGGCGCAGAGGAACAACGTGGCCCCCGACGAGCTGTACACGCCGCACAGCTGGCT
GCTCCGCGTGGTATATGGTGAGCGCCTCCTGAGGGGCCGGCAGGGCAGCCCAGGGTCAGG

14975 CTGGGCAGACCTGGGACTCATGGAGCTGGGGAGCTCCTCAGAGCGGTCCTCCCATAGGGG
GCCTTCATGTGCCCTCGGGGTCAGTTGCTGGAGGGACCCCCACCCAGGAAGGGACTGGCC
CAGGGCCCTGAGGGCGGATGGTGGGAGGCCACCCCTCCTGGTTTGAGCCAGGCCTACCAG

FIGURE 3, page 19 of 26

GTGCTCCCAGGCCCCAAGGCTCAGACACTGCCCCTACCAGGAGCTCTATGTGGAGGACTT
CGCCAGCATTGACTGGCTGGCGCAGAGGAACAACGTGGCCCCCGACGAGCTGTACACGCC
[G,C]
CACAGCTGGCTGCTCCGCGTGGTATATGGTGAGCGCCTCCTGAGGGGCCGGCAGGGCAGC
CCAGGGTCAGGGTCAGGGTGTCGCCCACTCATTCACGCACTCATCCCCTGCCAGCGGCAC
TGGGCCACCTCCTCTGTGCCAGGCCCCAGGGGGCGGGATCTCATCGCCCTGCCCCTCCAC
CCTGAGAACCAGCTGGTCTTCTACTCTCAGGAGTCCACCCTGTGCAAGGGTGTGTGGTAG
GAGGTGTGGGGCAGCCCCTCCTGGGCAGGGAAGGAGGAGCTCAGAGACCAGGCCTGGGGG

16031 TTCCGTCCCCCACCGGCTCTTGTCCTCAGTGTGCCTGGACACTCTCCTAGAGGCCCCTCC
CTGAGATCTTGCTGGCTAGCTGGCTAGCTGGGAGGGGTGCTTTTTCCTCACTTGGTTCCC
TCTCCCCAAACAGTTCATCATTCGCCATTCTCCCGTGGGGTTTAGACATGCCCAGGGTGG
GTGGGAGTAGCAGGTGCCACTCCTGATTCCTCCTGCCTAGCTAGGGACTTGGAGCTCTCA
CCTCTGTGGGGCCTGCAGGGGTCCAGGTGTGGCCAGTTCAGTGACCTTAGAGGGTGCAAT
[C,T]
CCCGGGCTGTGCTGGTGCGTGGCCGCCTCCTGACAGAGTCAGCAGGCCCTGGGCTGTGCT
GCAGCTGCTGCCGTAGCTGTGCGCGTAGCTGCTGCGGTGTAGTGGGTTGGCTTAGGCATT
CTCTGGACATACCCAGGTGGCACTGGGCCACTGAGTCCCACCCTGACACTGCATCTCGGA
TTTTCTGGGCCTCATGCCACCTCAGTGGATCACAAATCCTGACTGACCCTGCAGCGGGTC
CCTTGTTTTTGCTCAGCAGTGATGTGGTTCTTTGTGGGTTTTGGTTTAATCCCATATAG

16891 GTGGAGTGCTGCTCCTTCTCACAGCCTAAGGCAGGCTGTGGCCTTGGCCGACACTGCCTC
TGTCTGAGTTGGGTCCTGGGGACACAGTTGTTGCCCATCCTCGCTCAGGAAATGCCTGTT
AGAGCAGAAGGCCCCTGTCCTGGCCCTGAGTGATCTGCACGGCACTTTATGCCTGGGGGC
TGCTGTGGATCTGGACGAGACCTTGTCCCTGGAGGCTGCTGTGGGTCTGGAGCGGAGCCT
TGACAGGGCTGTCTCTCCTGCAGATCTCGAAAACCATCAACATGCTTGTGCGCTGGTATG
[-,T]
GGACGGGCCCGCCTCCACTGCCTTCCAGGAGCATGTCTCCAGAATCCCGGACTATCTCTG
GTGAGTGTGGCTGGGATATGCTGGCGGGGCCTCTCACGAAGACTGGATCTGAGCCCCAGC
TGCATCCCAGTGAGGGGGCCCCCACGGTGCCATCTGGGAATACTGCCAGGGAATACCTCC
AGGAACCAGCAGTGTCAGGGCTTGTGGAAGCCACTGAGGGTTGTCTTTGAATTGGAAGAT
TTGCCACCCAGTGGAAGTGTGGGGTGTTCCCAGAAGGTAGAGTGAGGAAGGGGGTGGTAG

19359 CCACACACCACCCCCTGCCCAGTCCCCATGTCTGTCTGGTCAGTGCCCAGCTCTGTCTCA
CTAGGGTTTGGTCACCGGCCCTTTGAACTGAGACCAGGCTGTGTACCTGTGAGCCCAGCT
CGGGGTGAGATTTGAGGTGGAGCCTTCCCAGCCCTGTGCAGAATTCCCATCACCTCCAGG
TGTACTCAGAAATGGGGATCATTGGCCAGGTGCGGTGGCTCACGCCTGTAATCCCTACAC
TTTGGGAGGCCAAGGTGGGCGGATCACAAGGTCAGGAGATAGAGACCATCCTGGCTAACA
[C,T]
GGTGAAACCCCGATGCTACTAAAAAATACAAAAAAAATTAGCTGGATGTGCTGGCAGGAG
CCTGTAATCCCAGCTACTCCGGAGGCTGAGGCAGGAGAATGGCGTGAACCCAGGAGGCGG
AGCTTGCAGCGAGCTGAGATCACGCCACTGCACTCCAGCCTGGGCAACAGAGCGAGACTT
CATCTCAAAAAAAAAAGAAATGGGGTCATTTCCAGGCATCACCATGACTGAGGTGCGCCA
CTGTCATTGGGTGAGAGCAGCTGGATGCTCTATGTGTAGGTGCTGGAGCCTCTGAGGGAT

19405 CCAGCTCTGTCTCACTAGGGTTTGGTCACCGGCCCTTTGAACTGAGACCAGGCTGTGTAC
CTGTGAGCCCAGCTCGGGGTGAGATTTGAGGTGGAGCCTTCCCAGCCCTGTGCAGAATTC
CCATCACCTCCAGGTGTACTCAGAAATGGGGATCATTGGCCAGGTGCGGTGGCTCACGCC
TGTAATCCCTACACTTTGGGAGGCCAAGGTGGGCGGATCACAAGGTCAGGAGATAGAGAC
CATCCTGGCTAACACGGTGAAACCCCGATGCTACTAAAAAATACAAAAAAAATTAGCTGG
[A,G]
TGTGCTGGCAGGAGCCTGTAATCCCAGCTACTCCGGAGGCTGAGGCAGGAGAATGGCGTG
AACCCAGGAGGCGGAGCTTGCAGCGAGCTGAGATCACGCCACTGCACTCCAGCCTGGGCA
ACAGAGCGAGACTTCATCTCAAAAAAAAAAGAAATGGGGTCATTTCCAGGCATCACCATG
ACTGAGGTGCGCCACTGTCATTGGGTGAGAGCAGCTGGATGCTCTATGTGTAGGTGCTGG
AGCCTCTGAGGGATCGTCCAGTCCTAGAAGTGTCCTCAGAGGGACACTGTCCTGCCTGGT

19653 CTAACACGGTGAAACCCCGATGCTACTAAAAAATACAAAAAAAATTAGCTGGATGTGCTG
GCAGGAGCCTGTAATCCCAGCTACTCCGGAGGCTGAGGCAGGAGAATGGCGTGAACCCAG
GAGGCGGAGCTTGCAGCGAGCTGAGATCACGCCACTGCACTCCAGCCTGGGCAACAGAGC
GAGACTTCATCTCAAAAAAAAAAGAAATGGGGTCATTTCCAGGCATCACCATGACTGAGG
TGCGCCACTGTCATTGGGTGAGAGCAGCTGGATGCTCTATGTGTAGGTGCTGGAGCCTCT
[G,A]

FIGURE 3, page 20 of 26

AGGGATCGTCCAGTCCTAGAAGTGTCCTCAGAGGGACACTGTCCTGCCTGGTGGCCCATG
AAGAAAGGGAGGGCTCCCTGAGTCTCCCTGACGTGTGTCTGCCTGCAGGGCTCAGCCTTC
TCTGAGGCCCTTGTCAGCCATGAGGGGTGCCCAGGGCTCAGAGCCTGAGGCTGAGCGTTG
GCTGGGTGGGAGCCCCCACACCTGGCCCTCAGGCGCCCATTGGATCCTGGAGGCAGTGGC
TGGGAGTGGGAGGGGCTGCATCTGCTGCTGTAACACCATCCTTTGTGTGTAGGGCACCAA

19742
AGGCTGAGGCAGGAGAATGGCGTGAACCCAGGAGGCGGAGCTTGCAGCGAGCTGAGATCA
CGCCACTGCACTCCAGCCTGGGCAACAGAGCGAGACTTCATCTCAAAAAAAAAAGAAATG
GGGTCATTTCCAGGCATCACCATGACTGAGGTGCGCCACTGTCATTGGGTGAGAGCAGCT
GGATGCTCTATGTGTAGGTGCTGGAGCCTCTGAGGGATCGTCCAGTCCTAGAAGTGTCCT
CAGAGGGACACTGTCCTGCCTGGTGGCCCATGAAGAAAGGGAGGGCTCCCTGAGTCTCCC
[T,C]
GACGTGTGTCTGCCTGCAGGGCTCAGCCTTCTCTGAGGCCCTTGTCAGCCATGAGGGGTG
CCCAGGGCTCAGAGCCTGAGGCTGAGCGTTGGCTGGGTGGGAGCCCCCACACCTGGCCCT
CAGGCGCCCATTGGATCCTGGAGGCAGTGGCTGGGAGTGGGAGGGGCTGCATCTGCTGCT
GTAACACCATCCTTTGTGTGTAGGGCACCAACGGCTCACAGATCTGGGACACCGCATTCG
CCATCCAGGCTCTGCTTGAGGTTCGTGGCTCCTTCTCTTTTCTCAGCCTCAGCTGACCTT

20054
GCCTGCAGGGCTCAGCCTTCTCTGAGGCCCTTGTCAGCCATGAGGGGTGCCCAGGGCTCA
GAGCCTGAGGCTGAGCGTTGGCTGGGTGGGAGCCCCCACACCTGGCCCTCAGGCGCCCAT
TGGATCCTGGAGGCAGTGGCTGGGAGTGGGAGGGGCTGCATCTGCTGCTGTAACACCATC
CTTTGTGTGTAGGGCACCAACGGCTCACAGATCTGGGACACCGCATTCGCCATCCAGGCT
CTGCTTGAGGTTCGTGGCTCCTTCTCTTTTCTCAGCCTCAGCTGACCTTCCTGTGCACGT
[A,G]
AGCCCACGCATCCACCTGAGGGCAGCACTGCTGGCCACACACTTGCCACTCCTCGATACT
TCCAGTGACCTGGGCTCTGGCCTCTGGCTTCAGAGGGTCGTGCTGTGGAGGGGGCGGCCT
TGGCCAGCAGCCTTGGGTGTTGGGCTGGGTCGGGGGCCTTGGGAGGGCAGGGGCTGGAGG
CTGTGTGAGAAGGGGAGTCTGGTGAAGGCTGTTTCTGAGAGTGCAGGCAGGAGTGGGACT
CCAGGCTCTTCTTAGAACTGGAACTGCTTGGGCCAGGCACGGTGGCTCACACCTGTAATC

20627
CCAGGCACGGTGGCTCACACCTGTAATCCCAGCACTTTGGGAGGCCGAGGAGGGTGGATC
ACGAGGTCAGGAGTTCAAGACCAGCCTGGCCAAGATGGTGAAACCCCGTCTCTACTAAAA
GTACACAAAAATTAGCCAAGCGTGGTGGCGGGCACCTGTAATCCCAGCTACTTGGGAGGC
TGAGGCAGAGAATTGCTTGAACCCGGGAAGTGGAGGGTGCAGCGAGCCGAGATTGTGCCA
CTGCACTCCAGCCTGGGTGACAGAGAGAGGCTCCGTCTCAAAAAAAAAAAAAAAAAAAAA
[-,A,G]
AACTGGAACTGTTTGTTATGGGCATTCTCGAGCCAGTACTGGAGAAAAACGAGAGTGGAT
TTTTATGCCGGTGGGAATGAGGTAGGTGGGATTCTGAAGGTGTTTCTGGAGAGCCCTGAG
GGCTGGGCCACGCAAAGGGCCTGCCTACACAGGGTGCTGGAGACCCTCTGGGCATGGATG
CTGGCCAGGCAGGGGGGTGCTGGCATCCATAAATGGTCTCCTGCGCCCTTCCATCTTCAG
TCATATCTCATGGACTTTTGCTGTTTTGTCTTTAAAGGTAAGTGCAGCAGGAGACCCTGG

21337
AGCCTCTCTGTCCTGCTGTCTCTTCCAGGCGGGCGGGCACCACAGGCCCGAGTTTTCGTC
CTGCCTGCAGAAGGCTCATGAGTTCCTGAGGCTCTCACAGGTGAGGCCGGTGCCTGGGGC
TCTGAGGGGGCTGAAGAGGGGGATCAGGGCTGGGAGCTCCTGCAGGCAGAAGTGCCCACC
TCACCTCCACCCTGCCCTATTTCCTGCACTGGTGTTTCAGGGTCACCCCCACCCTCCCAT
CCCCTCCCTAGCCCCTGCTCCATCCACCGGTCCTCCTCGGGCTGGCCTCACCTGGGGCAG
[T,C]
TCTCTGAGGCCTGCAGGGTGCTGGGGGTGCTGGCAGTTTCTGCGTCCTGCTCATGTTGGA
GCCACTGTGTGCAAGGGCCAGGCACGGGCAGGGGCTGTGTACCCTGAGCTGCACAGCCTA
CACGGCACCTCCATGTCTCTGAAGCACCTTCTGCCCATGGAGGTGACGCCAGCCTGTGGA
CTTGCCCTCCTGAGACTGTTTGCAGCAAAAGCCCCGGTCCCTCCTGCCAGATCAGCTGCC
CACAGACCCTGCCCGAGCCCATAGTTTGACCTCAGTGTCTCTCACACGTGCCTGCACCCC

21894
GCCCATAGTTTGACCTCAGTGTCTCTCACACGTGCCTGCACCCCAGTCTGCAGCCACAGT
CATCCCATACATGCGCCCCAACCTCCCGTGTCTCCCACACCCTGTCCCGGCCACGGCCTC
AGCCAGTGTCCCTCTGCCTGGAACCGCTGCCCCCCAGCCCCGTCTCCCTCCCTTCAGCTC
TCACTAGGACATTGTTCTGCAGGGCTTCTGGGTCTTCCTGGCCTCTGTGTGGCCAAGGCT
GGCACCCATCTTGGGCTCAAGCAGAGGAGGGGCATTGTCCTGCTGTGCCTGGCCCAATGG
[C,T]
GGCCTGCTCCTGCTCCTGCCTCCTGCCCAGGACTTGCTCTGGGTGATGGGGACTTGGGGA
GGCTGACTGAACCCTACGGCACTCCAGGCCTCTTCCCTTCTCACTGAGGTGAGAGAGGCA
GCCAGAAGCTGAGGTTGTTCAGGAGGCATTGGGGGCGCCTGGCACAGAGCACACCCGCAG

FIGURE 3, page 21 of 26

AGACCTGGGCCCCCTCCCTGCCTTCTGGCCGGTGGGGAGATCACAGGGGAGTCAGGTGCT
GACTCCCAGTCCCGTCTGGGCTGGTTTGAGCCCTCGCTGGCCAGTCACGTTTCCCAGCAG

23360 TGAGAACTGGGGTGTGGACACCCCCAGCCTGGAGTCATGGCTTGTGCTCTGCAGGGTGGC
TTCTCCTTCAGTACGCTGGACTGCGGCTGGATCGTTTCTGACTGCACGGCTGAGGCCTTG
AAGGCTGTGCTGCTCCTGCAGGAGAAGTGTCCCCATGTCACCGAGCACATCCCCAGAGAA
CGGCTCTGCGATGCTGTGGCTGTGGTAAGGCTGTGGTCCCAGCAGCCCCGTCCATACCTC
GTGTCCTGCAGATGAGCTGCGTGCTCACTTCCACTCCTGTGGGCTCCAGCCCAGCACACA
[G,T]
TCCGGCCAGGCCGTAGGAGCTTGTCCTTGGATGGTGTCTATATGTGGAGAACTGTGAGCT
CTGGCTGGACCCCTAGGGGCCTTGCTGGGCTGTGTGCACAGGGCCCTGCACTGCGGAGCT
GGTGTCCAGCCCAGCCACCGATACTTGGGGGAGCCGGCGTGGCCCCCAAGGTTTCTCTCT
GGTGGTTTCCACTGGGTGTCTGAAGAGGGAATTTGTTGGTGTTGGTTTTGGTGCCACATC
CTTTCAGCACATCTGGCTTTTGTGTGTGTTTCCCAGTGGAGACCCTGCCCTTTTCTGGCA

26758 CAACCTCCGTTTCCGGGGTTCAAGCGATTCTCCTGCCTCAGCCTCCCGAGTAGCTGGGAC
TACAGGTGCTGACCACCATGACTGGCCAATTTTTTGGTATTTTTATTAGAGACAGGGTTT
TACCATGTTGTCCAAGCTGGTCTTGAACTCCTGACCTCAGGTGATCCACCTTCCTTGGCC
TCCCAGAGTGCTGGGATTACAGGTGTGAGCCACCACACTGGCCTTTGCTATTTTCTTTCT
CCTTTATTTTTCTAACTTGAATACTTAGATATTTGATTTTCAGGCTTTTATTGAAATATG
[A,C]
ATTTGAGGCTATAAATGAGTTTTGAGATATCATTCAGTTAAATGTGTGTTCTGGTGCTTG
CTGTGGTAGCACAGATACTAAAAGTGTTTTCTGTTTCTACTGTTCTTCTCTGGCCCATGA
GTTATGTGGGAGTATGCTGCTTCATTTACAATCTGAGAATGTTCTGGTGTGGTTTTTTTG
GAAGCCGTGGATGGAGCAGGGGTTTTCTTGTGCTTCACAGGTGCAGCTAGGAGGGCACTG
TGTCCAGGGTCTTCTGTCGGCCTGGCGTGGCCCTTGGCCATGTGCTGCTCTGCGGCATGA

27033 ATTTTCAGGCTTTTATTGAAATATGAATTTGAGGCTATAAATGAGTTTTGAGATATCATT
CAGTTAAATGTGTGTTCTGGTGCTTGCTGTGGTAGCACAGATACTAAAAGTGTTTTCTGT
TTCTACTGTTCTTCTCTGGCCCATGAGTTATGTGGGAGTATGCTGCTTCATTTACAATCT
GAGAATGTTCTGGTGTGGTTTTTTTGGAAGCCGTGGATGGAGCAGGGGTTTTCTTGTGCT
TCACAGGTGCAGCTAGGAGGGCACTGTGTCCAGGGTCTTCTGTCGGCCTGGCGTGGCCCT
[T,C]
GGCCATGTGCTGCTCTGCGGCATGAGGTGGGCGTGAGTTGTCCTCAGCCACATTTAGAGA
ATTGGCCTTTTAAAAAATAGATCATCTTTTAAAAATCACTGTAATAAAAGTAAAGCAGGT
TCTTTGCAAACAAGACTTGCAAAATACAGAGAAGCGCAAAGAAGAAGCTAAGTCGCCCCT
CCTCGCCCCTGAAGGAGAATCTGCTGTTGCTGTTTGGTCTCCACATTTCCATGGCGGCTT
GCTGCCCCTTTCACGCCTGGCCCACTTTGTGCCTGGTGAGGTTTCTAAAAGCCCCACCCT

27332 TTGGCCATGTGCTGCTCTGCGGCATGAGGTGGGCGTGAGTTGTCCTCAGCCACATTTAGA
GAATTGGCCTTTTAAAAAATAGATCATCTTTTAAAAATCACTGTAATAAAAGTAAAGCAG
GTTCTTTGCAAACAAGACTTGCAAAATACAGAGAAGCGCAAAGAAGAAGCTAAGTCGCCC
CTCCTCGCCCCTGAAGGAGAATCTGCTGTTGCTGTTTGGTCTCCACATTTCCATGGCGGC
TTGCTGCCCCTTTCACGCCTGGCCCACTTTGTGCCTGGTGAGGTTTCTAAAAGCCCCACC
[C,A]
TTGAGCGCGCTCCTCCAGCACGAGCAGTAATGGCACAGGTGTTGTGTCATTTTACTCAGT
AGCCTCTGGGTTATTTTTCAGTTTTCCTTGTTGTTTTTTAGCTTTTCCCCATTTTAACCT
TAACTGGTATTTTCTTGTTAAATATTTATTCATGACCATTATTATTCCCTAGAGCCACAT
GGCTTGGGGTCCACCTGCCTGGGTCCGCCCCCATCCCTGCCCCTTCTGGCTGTCTGACCT
GGCCTGGTGACTTCTCTTCTCTGCTCATCTCTCTCCCTGCCTGAGTGGGCAAGAGTACAG

27538 TGTTGCTGTTTGGTCTCCACATTTCCATGGCGGCTTGCTGCCCCTTTCACGCCTGGCCCA
CTTTGTGCCTGGTGAGGTTTCTAAAAGCCCCACCCTTGAGCGCGCTCCTCCAGCACGAGC
AGTAATGGCACAGGTGTTGTGTCATTTTACTCAGTAGCCTCTGGGTTATTTTTCAGTTTT
CCTTGTTGTTTTTTAGCTTTTCCCCATTTTAACCTTAACTGGTATTTTCTTGTTAAATAT
TTATTCATGACCATTATTATTCCCTAGAGCCACATGGCTTGGGGTCCACCTGCCTGGGTC
[C,A]
GCCCCCATCCCTGCCCCTTCTGGCTGTCTGACCTGGCCTGGTGACTTCTCTTCTCTGCTC
ATCTCTCTCCCTGCCTGAGTGGGCAAGAGTACAGCCTCACAGAGTGGTGGGATTGTGTGA
GATGCCACAGGGAAGCACATGTCAGTTGTTGTCACTGTGTAGAACAATGAGTCCCGGATG
TGGCCCGCAGGGGAGCAATGGTGACTTAATCGCGGGCTTCCTCTGCATTTCTTTGGTGAC
TTCCAAGCTAGAACATTCTTTTTTTGTTTATTTGTTTGAAGCAGGGTCTCACTCTGTTAC

FIGURE 3, page 22 of 26

27625 CCCCACCCTTGAGCGCGCTCCTCCAGCACGAGCAGTAATGGCACAGGTGTTGTGTCATTT
TACTCAGTAGCCTCTGGGTTATTTTTCAGTTTTCCTTGTTGTTTTTTAGCTTTTCCCCAT
TTTAACCTTAACTGGTATTTTCTTGTTAAATATTTATTCATGACCATTATTATTCCCTAG
AGCCACATGGCTTGGGGTCCACCTGCCTGGGTCCGCCCCCATCCCTGCCCCTTCTGGCTG
TCTGACCTGGCCTGGTGACTTCTCTTCTCTGCTCATCTCTCTCCCTGCCTGAGTGGGCAA
[G,C]
AGTACAGCCTCACAGAGTGGTGGGATTGTGTGAGATGCCACAGGGAAGCACATGTCAGTT
GTTGTCACTGTGTAGAACAATGAGTCCCGGATGTGGCCCGCAGGGGAGCAATGGTGACTT
AATCGCGGGCTTCCTCTGCATTTCTTTGGTGACTTCCAAGCTAGAACATTCTTTTTTTGT
TTATTTGTTTGAAGCAGGGTCTCACTCTGTTACCTAGGCTGGAGTGCAGTAGCAAAATCA
TGGCTCACCACAGTCTCAAACTTCCGGGCTCAAGCAATCCTCCCACCTCAGCCTCCTGAG

27736 TTTCCCCATTTTAACCTTAACTGGTATTTTCTTGTTAAATATTTATTCATGACCATTATT
ATTCCCTAGAGCCACATGGCTTGGGGTCCACCTGCCTGGGTCCGCCCCCATCCCTGCCCC
TTCTGGCTGTCTGACCTGGCCTGGTGACTTCTCTTCTCTGCTCATCTCTCTCCCTGCCTG
AGTGGGCAAGAGTACAGCCTCACAGAGTGGTGGGATTGTGTGAGATGCCACAGGGAAGCA
CATGTCAGTTGTTGTCACTGTGTAGAACAATGAGTCCCGGATGTGGCCCGCAGGGGAGCA
[A,G]
TGGTGACTTAATCGCGGGCTTCCTCTGCATTTCTTTGGTGACTTCCAAGCTAGAACATTC
TTTTTTTGTTTATTTGTTTGAAGCAGGGTCTCACTCTGTTACCTAGGCTGGAGTGCAGTA
GCAAAATCATGGCTCACCACAGTCTCAAACTTCCGGGCTCAAGCAATCCTCCCACCTCAG
CCTCCTGAGTAGCTGGGACTACAGGTGCATACCATCACCTGTGGCTAATTTTTTAAATGT
TTTGTATTTTTTAAATGTTGCTCAGGCTGGTCTTGAACTGCTGGGCTCAAGCAATCCTCC

30688 TACGCAATTGATTTTGATACTGATCTCATAGCTAGACAATTTTGCTAAACTTTTAAAAAA
ATTTATGTACTTTATCTTTTATAGCAGCTTTAAATTTACAGAAAATTTGAGTGGAAGATG
CAGTGTTCCCATAAAGCCGCTAACTCCTCGCACCTTCCCTCAAGTTTCCCCAGTACTAAC
ATCTTGCATTCAAGTGGTGCGTTTGCAACATTCATAAATTATTATCGTCCAGAGTCCATT
GTTTACATTCAGCTTCCTCTTCATGTTGTTCATTCTGTGGTTTCACAGATGTGTGATGCA
[T,C]
GTGCCCACCACTGCAGTGTCACACAGGATCTCACTGCCCCGGAGTCCTCTGCGCTGTCCC
CGCCTCCAGAACCCCTTAGTAGCAAACACTGATATTTTTACTGTCTCCATAGTTTTGCCT
TTTCAGACTGACCTATTTCACTTAGTAAGAAGCATTTAAGATTCCTGAGTCTCTTTCTAT
GGCTCAATAGCACATTTCTTTTTAGTGCTGAATAATATTCCATTGTCTGGATGTACCACA
GTTTATTCATTCACCTACTAAGGTGAATGTCTTGCTTGCTTCCAAGTTTTGGCAACTATG

31172 TCAATAGCACATTTCTTTTTAGTGCTGAATAATATTCCATTGTCTGGATGTACCACAGTT
TATTCATTCACCTACTAAGGTGAATGTCTTGCTTGCTTCCAAGTTTTGGCAACTATGAAT
AAAGTTGCTATCAATGTTAGCGTGCACATAAGTTTTCAGCTCATTTGGGTAAATGCCAAG
AAGCATGATTGCGGGATCCTATGGTAAGAGTGTGTTTAGTTCTGTAAGAAGCTGCCAAAC
TGTATCTTAAGTGGCTGCACCATTTGCGTTTCCACCAGCAATGATGAGCGTTTTGTTGCT
[C,T]
CACATCCTCACCAGCATTTGCTGTTGTGTTTTGGGTTTTAGCCTTTCTAAGAGGTGTGTA
GTGGTATCTCCTTGTTTCAATTTGCAATTCCCTAATGACATTATGTTAAAATCTTGTCAT
ATAGTTATTTGCCATCTGTGTATCTTTTTCAGTGATGTGTCCTTTAAAGTCTTTGGCTCA
TTTTTAAATTAAATTTTCTTATTGTTGAGTTTTAGTTCTTCATATATTTTGGCTGCCAGT
CCTTTATCAGATATGTCTTTCGCAAATATTTTCTGCCTGTGTCTTGTCTTTTCATTCTAT

31433 ATTTGCGTTTCCACCAGCAATGATGAGCGTTTTGTTGCTCCACATCCTCACCAGCATTTG
CTGTTGTGTTTTGGGTTTTAGCCTTTCTAAGAGGTGTGTAGTGGTATCTCCTTGTTTCAA
TTTGCAATTCCCTAATGACATTATGTTAAAATCTTGTCATATAGTTATTTGCCATCTGTG
TATCTTTTTCAGTGATGTGTCCTTTAAAGTCTTTGGCTCATTTTTAAATTAAATTTTCTT
ATTGTTGAGTTTTAGTTCTTCATATATTTTGGCTGCCAGTCCTTTATCAGATATGTCTTT
[C,T]
GCAAATATTTTCTGCCTGTGTCTTGTCTTTTCATTCTATTAACAGTATCTTTTGCAGAGC
CAGTTTTCATTTCAAGGAAGTCCAGCTTATCAATGTTCTCTTTCATGTATCATGTTTTTG
GTGTTGTATCTAAAAAGTTACTGCCAAGCCCAAGGGTACCTAGATTTTTTCCTGTGTTAT
ATTCTAGGATTTTTAAAGTTTTGCATTTTACATCTAGGTCCATGATTCATTTTGAGTTAA
CTTTTGTGAAGGGTTTATGGTTTGTGTCTAGATTTTTTTTTTTTTTTTTTTTTTGCATGT

32660 CTCCTGGGCTTAAGGAATCCTCCTGTCTCAGCCTCCTGAGCAGCTAGGACCACAGGCATG
TGCCACTACGTTCAGCTAATTTTTCAATTTTTTTGTAGAGATGGGATCTTGCTCTGTTGC
CCAGGCTGGTCTCAAACTCCCGTCTGCTTTGAGATGATTATATATTTGTGTCCTTTGTTA

FIGURE 3, page 23 of 26

ATTTAGAGGATTATTATGGATTTTTCTAATGTTAAGACACCTTTGTATTTCTGAGATCGA
CCTTAGTATTGGTCTATATTTAAGACAGTATTCAGTTTCTCAGTTGTTTTTTGTTTTTTG
[G,T]
TTTTTTTTTTTGAGACAGAGTCTCTGTCTCCCAGGCTGGAGTCCAGTGGCACAATCTCAG
CTCACCGCAAGCTCTGCCTCCCGGATTCACGCCATTCTCCTGCCTCAGCCTCCCGAGTAG
CTGGGACTACAGGCGCCTGTCATCATGCCCAGCTAATTTTTTGTATTTTTAGTAGAGACG
GGGTTTCACCATGTTAGCCAGGGTGGTCTCAATCTCCTGACCTCGTGATCTGCCCACCTC
GATCTCCCAAAGTGCTGGGATTACAAGGCGTGAGCCACTGCGCCCGGCAGCAGTTTCTCA

32981

TCTCTGTCTCCCAGGCTGGAGTCCAGTGGCACAATCTCAGCTCACCGCAAGCTCTGCCTC
CCGGATTCACGCCATTCTCCTGCCTCAGCCTCCCGAGTAGCTGGGACTACAGGCGCCTGT
CATCATGCCCAGCTAATTTTTTGTATTTTTAGTAGAGACGGGGTTTCACCATGTTAGCCA
GGGTGGTCTCAATCTCCTGACCTCGTGATCTGCCCACCTCGATCTCCCAAAGTGCTGGGA
TTACAAGGCGTGAGCCACTGCGCCCGGCAGCAGTTTCTCAGTTTTAATTTGGAGTTTTGC
[A,C]
TCTGTGTTCATGAGTGAGCCTGAAATTTTCACTTTTCCATATCTTATTTCTCTGGGTTCC
TAGAATGAGCTAGAGAGTGTTCCTCCTTTCTGTTCTCTGGAAGAGTTTGTGTGAGATTAG
AATGAGTGTGTCTGATAATTTAGTTGCATTCATTTATAAAATTCCTAGGCCTAGAGTTTT
TTTTCTGGGAAAAGTTTACATTTTGACTCATTTTTTTAGTAGTTTTAGGACTGTTTAGGT
TCTCTATTTCTTGATTGAGCCAGTTTTGATAAGTTAATCTTTCTAATTTGTAGATATTTT

33557

AATCTTTCTAATTTGTAGATATTTTTCTCTAAGTTTGCAAATGTAATACATAAAACTTTCT
TGTCATTTCTCACCATATCTGTAGTTCTATCTTTTTATTGCTAATATTACTAATTTGTAC
TTTGACTATTTGTATTTGTTACCTGTTGCCGAGTAACAATATTAGTACAAACCTAGTGGC
TTAGAACAACACACATTGATTACTTCACCGTTTCTGTGTGTCAGAAGTCCAGGCGCGGCC
TCGCAGGTCGTCCTCTGCCTCAGGGTCTCTCCGGGCTTCAGTCAGGGTGTTAGCCAGGAC
[T,C]
GGGGTCTCGCCTGAGCTTCCAGTGAGGAAGGATCTGCCTCTGAGCACACAGGGTCCTCGG
CACGATCCCATTCCTCAGCTGGAAGCTGCCGACTGCCGTCTGCTGCGGGGCCTCTCTAGA
TGGCATCTTCACAAAAGCGAGAAGGGAGAGTTGGTAGAGGGAGTCTGCTAGCACCATGGG
AGTCGCGGTCACACAGACCTCGGTCCCAGGACCCGCACCCATCAACCCTGCCGTGATCTG
CTGGTTAAAGACAAGTCCCACGTCCCACAGGGTGACACTGGAGTAGACACTTCGCTCTGG

33652

TATTGCTAATATTACTAATTTGTACTTTGACTATTTGTATTTGTTACCTGTTGCCGAGTA
ACAATATTAGTACAAACCTAGTGGCTTAGAACAACACACATTGATTACTTCACCGTTTCT
GTGTGTCAGAAGTCCAGGCGCGGCCTCGCAGGTCGTCCTCTGCCTCAGGGTCTCTCCGGG
CTTCAGTCAGGGTGTTAGCCAGGACCGGGGTCTCGCCTGAGCTTCCAGTGAGGAAGGATC
TGCCTCTGAGCACACAGGGTCCTCGGCACGATCCCATTCCTCAGCTGGAAGCTGCCGACT
[G,A]
CCGTCTGCTGCGGGGCCTCTCTAGATGGCATCTTCACAAAAGCGAGAAGGGAGAGTTGGT
AGAGGGAGTCTGCTAGCACCATGGGAGTCGCGGTCACACAGACCTCGGTCCCAGGACCCG
CACCCATCAACCCTGCCGTGATCTGCTGGTTAAAGACAAGTCCCACGTCCCACAGGGTGA
CACTGGAGTAGACACTTCGCTCTGGCCTTTTCAGAGAACTGGTTATTTTTTGGAAATATC
AGTTAGATGTAGGATGGGTCTTGTCTTCTAAATCTATTGTTTTCTCTCTAATTGATTTTT

34390

CTCTGCCAATCCGCTTCCCGCTCTGGTGTCCTGTGGTTGCTTCTTTTTAAAACCCTCATC
GGTCTGTGTAAACTGTTTATTTTTATGTGGTTTTTAAGGGAGACCATTCTCATTCTTTTG
AGACCCTGGAAAGGATGGAATTGGGATAGGTAAACTGCTGTTTTACCAGAATGTTCACTG
GACCAATCTCGTGTTCCAGGGAGACCCTCACGCAGGGCTTAGAGTTCTGTCGGCGGCAGC
AGAGGGCCGATGGCTCCTGGGAAGGGTGAGTGAGCCTCCACTCGTGAGTGCAGAGATGCA
[T,C]
GGGATCCAGAGGTTTCTGCTCTCACACACTGCGTTCATAAATGTTGGCTTGTATGTTGTT
GCTACACCAGAAGTTTCTGGAAGTGAGCTGCCAGCCCGTGACTTCTGGGGGACCTCGTTC
CTTTGTGGCATGCGTGGCCTTTGCCCCGGTGGAAATTGCTCAGTACGTTGCTGGGCGCAG
CCGGGCTGCTGGGAGCGCGCTGTAGCCTGAGCGTGGCTATTCCCTCCACCCTTTCTGCTT
GCTCTTAGGGTCCAGCAGACAGAGCTGCTGTCTTCCACGGCCTTAATGCCTGAGGCACTG

34399

TCCGCTTCCCGCTCTGGTGTCCTGTGGTTGCTTCTTTTTAAAACCCTCATCGGTCTGTGT
AAACTGTTTATTTTTATGTGGTTTTTAAGGGAGACCATTCTCATTCTTTTGAGACCCTGG
AAAGGATGGAATTGGGATAGGTAAACTGCTGTTTTACCAGAATGTTCACTGGACCAATCT
CGTGTTCCAGGGAGACCCTCACGCAGGGCTTAGAGTTCTGTCGGCGGCAGCAGAGGGCCG
ATGGCTCCTGGGAAGGGTGAGTGAGCCTCCACTCGTGAGTGCAGAGATGCATGGGATCCA
[G,C]

FIGURE 3, page 24 of 26

```
         AGGTTTCTGCTCTCACACACTGCGTTCATAAATGTTGGCTTGTATGTTGTTGCTACACCA
         GAAGTTTCTGGAAGTGAGCTGCCAGCCCGTGACTTCTGGGGGACCTCGTTCCTTTGTGGC
         ATGCGTGGCCTTTGCCCCGGTGGAAATTGCTCAGTACGTTGCTGGGCGCAGCCGGGCTGC
         TGGGAGCGCGCTGTAGCCTGAGCGTGGCTATTCCCTCCACCCTTTCTGCTTGCTCTTAGG
         GTCCAGCAGACAGAGCTGCTGTCTTCCACGGCCTTAATGCCTGAGGCACTGGAGTTGGTG

34989    TGGAGTTGGTGGGCTGGCTGGGGCACGTGTGATTGTTGCAGAATGCGTGTTGTTTCACAC
         ACCGGCTGTGAACAGGGTGGAAGGGCTGAGGCTCTCCCTGTTTCCCTCCAGCTCCTGGGG
         AGTTTGCTTCACCTACGGCACCTGGTTTGGCCTGGAGGCCTTCGCCTGTATGGGGCAGAC
         CTACCGAGATGGGTGAGTGAGTGCCTGTCCTCTGGTGGGTGGGGGTTCTCAACCCAATGC
         TCTGTCATGAGTGTTTTTTGCTTTGACATTTGGTTTTAGGGTTTGTTTGTTTGTTTGTTT
         [G,-]
         TTTTTGAGACGGAGTCTCGCTCTGTCAACCGGGCTGACATGCAGTGGCATGATCCTAGCT
         CACTGCAGTCTCAAACTCGTGGGCTCAAGCGATCCTCCCGAGTAGCTGGGATCACAGGTG
         CACGCCACCACCCCGGGCTAATCTTTTAAAACTTTTATGTAGAGATGGAGTCTTGCTGTG
         TTGCTCACACTGGTTTGGGCTCAAGCAGTCTTCCTACCTCGGCCTTCCAAAGTGCTGGGG
         TTACAGGCATGAGCCAATGTGCCTGGCCTGTTTTTAATATTTTTAAACAGTGAGATAAGA

35067    GGAAGGGCTGAGGCTCTCCCTGTTTCCCTCCAGCTCCTGGGGAGTTTGCTTCACCTACGG
         CACCTGGTTTGGCCTGGAGGCCTTCGCCTGTATGGGGCAGACCTACCGAGATGGGTGAGT
         GAGTGCCTGTCCTCTGGTGGGTGGGGGTTCTCAACCCAATGCTCTGTCATGAGTGTTTTT
         TGCTTTGACATTTGGTTTTAGGGTTTGTTTGTTTGTTTGTTTGTTTTTGAGACGGAGTCT
         CGCTCTGTCAACCGGGCTGACATGCAGTGGCATGATCCTAGCTCACTGCAGTCTCAAACT
         [C,G]
         GTGGGCTCAAGCGATCCTCCCGAGTAGCTGGGATCACAGGTGCACGCCACCACCCCGGGC
         TAATCTTTTAAAACTTTTATGTAGAGATGGAGTCTTGCTGTGTTGCTCACACTGGTTTGG
         GCTCAAGCAGTCTTCCTACCTCGGCCTTCCAAAGTGCTGGGGTTACAGGCATGAGCCAAT
         GTGCCTGGCCTGTTTTTAATATTTTTAAACAGTGAGATAAGATCCCCGGTTGAAATGAAG
         ATGTTTCCCTGGTCCCACAGCTCTCTGGAGCTTCCTGACATGTATGCTGGAGGGACGCTT

35495    CAGTCTTCCTACCTCGGCCTTCCAAAGTGCTGGGGTTACAGGCATGAGCCAATGTGCCTG
         GCCTGTTTTTAATATTTTTAAACAGTGAGATAAGATCCCCGGTTGAAATGAAGATGTTTC
         CCTGGTCCCACAGCTCTCTGGAGCTTCCTGACATGTATGCTGGAGGGACGCTTCTGGTCT
         CCGGCCCCTCCAGGCATACAGATGCCTCCCAACCCTGAGTAGGAAGATTAGGGTCCACGG
         CCTCGCTGGAGCGGGTTAGAAGGCAGGAGATCTCCGGTCCCAGCCGTGTCTCCAGCCGCC
         [G,A]
         GACTCTCTCCCAGCCCTGTCTCCAGCTGCCCCACTGTCTCCCAGAGTCTGCCGTGTGGAT
         GTTTAGAGGTGGGGAGCACCGTGCTTGGCTGAGTGCAGCTTGTGAGACGCTGCTCCCAAG
         CACTGCAGACCTCACTCAGCCTGACGCGTCCGTGAGGCCATCCTCGGTACTCGCATGTCC
         CTTTGTCTTCCCAGCGACTCTGGGAGGCAGGAGTATCTGTTCCCAGTTCACATCTGCAAA
         AGTCAAGCTCGGGTTTCAGTAGTGGCCCATGGCCCTTAGGTAGGGTGGCCCCATCGTGCA

36001    GGCAGGAGTATCTGTTCCCAGTTCACATCTGCAAAAGTCAAGCTCGGGTTTCAGTAGTGG
         CCCATGGCCCTTAGGTAGGGTGGCCCCATCGTGCAGGCTCCTCCCCGTACCCCAAGGCAG
         CCTGCTGGGGTGAGAAGCCAGGGGTCTGGGACCTTCCTTGGTGTGATGGTGTCTCCTGTC
         TCTGGTCTTTGCAGGACTGCCTGTGCAGAGGTCTCCCGGGCCTGTGACTTCCTGCTGTCC
         CGGCAGATGGCAGACGGAGGCTGGGGGGAGGACTTTGAGTCCTGCGAGGAGCGGCGTTAT
         [T,G]
         TGCAGAGTGCCCAGTCCCAGATCCATAACACATGCTGGGCCATGATGGGGCTGATGGCCG
         TTCGGTGGGGACGACGGGACCGTCCCTGAGCCTTGGGTTTGGGTAGAGGAGGGACACTCA
         GCTGTGAGCCGGTGGCCTGGGCTGAGTGAATGTAGAGAGGAGGGGAGGCCTGTGGGCCAG
         GTCAGCTGCCACTCTGGGAACAGACACCTACAAGAGCCACATGCCTGGTTCCTGGGGCAA
         GAACGTGGGCTGCTCTGACCAAGTGGGGCCCTGCAGAGAGGCTCGCCTCTTAGAAGTGAA

38948    ACAGCTCCCCAATGGCGACTGGCCGCAGGTATGCCGCCAGGGACCTGAGCGCACAAGGCC
         CAGCACTGACCTCCAGCGTGCATGGCTGTTTCCACGTCCCCCTGCTCTGTGTCCTTTTTG
         GGGTACTTTGGACACTTGGGAGGCGTCACCTCTGCCAGTGAATGCCACAGTTGGTGGCAG
         GTCTGTGGCAGGTGGTCGGGTCCTAAAGTCCAGATCTTGCTGTTGTTTCAAGTGATGCTC
         TGGGTGGGGGAGGAGCTGGATGGGAGAAGCCAGTGGGCGGGAAGCCTTTTTGCTGCAGGA
         [C,T]
         AGACCCTCCCACTCCAGATGACCTAGTGGCCCCTCACTGAGCCAGAAGTCCCTGTGGTGT
         GGGTGTCATGAGGTCATGTGAGGCCAACCGCCCTCCCCTGGGATGAGGCTGAGTTGGTGG
         AAGCTGATGTGGTTGTGAGGGGCTGGTGACCCTGGCTTAGGGTTTGCTGCAGGGCGGGGA
```

FIGURE 3, page 25 of 26

GTCTGAGCTGGGCTGATGGTGCCATGACTGATGCGGGATGGACTACTTGCTTTCCTATGC
TCTTGCTTAATTAGCCCTTTCCAGGCTGACTCACCCACAAGCCAGCCAAGCCAACAGCCA

39160
GATCTTGCTGTTGTTTCAAGTGATGCTCTGGGTGGGGGAGGAGCTGGATGGGAGAAGCCA
GTGGGCGGGAAGCCTTTTTGCTGCAGGACAGACCCTCCCACTCCAGATGACCTAGTGGCC
CCTCACTGAGCCAGAAGTCCCTGTGGTGTGGGTGTCATGAGGTCATGTGAGGCCAACCGC
CCTCCCCTGGGATGAGGCTGAGTTGGTGGAAGCTGATGTGGTTGTGAGGGGCTGGTGACC
CTGGCTTAGGGTTTGCTGCAGGGCGGGGAGTCTGAGCTGGGCTGATGGTGCCATGACTGA
[T,C]
GCGGGATGGACTACTTGCTTTCCTATGCTCTTGCTTAATTAGCCCTTTCCAGGCTGACTC
ACCCACAAGCCAGCCAAGCCAACAGCCAGGGCTCCAGTTCAGGGACTAGCCCTCAGCTGA
CTGGTGAAGCCTTTGTGTTTATTTCTCTGTGTTCTTTTAGGAAAACATTGCTGGGGTCTT
CAACAAGTCCTGTGCCATCTCCTACACGAGCTACAGGAACATCTTCCCCATCTGGGCCCT
CGGCCGCTTCTCCCAGCTGTACCCTGAGAGAGCCCTTGCTGGCCACCCCTGAGAACATGC

40405
TGTCATGGAGCCGCATACCCCTGGGTTGTGAGCTCGCCTGCATATGCAGGGTCTGTCATG
GAACATCCCAAGTCTGTGCAGCAGGGGAGCCCCATGCCCCTGGGACATGAACCCACCTGC
GTGGAATGCTGTTTGTGAGGTGTCTACAGGGTTTATAGTAGTCTTGTGGACACAGAAATG
CACAGGGGACACTTACGGACACAGAAATGCACAGGGGAGGCCGAGCATAACCAGGGGTGA
GGGGCAGGCAGCAGTTGTAGTTACTGCCGCGGGGCACTGCTATGTGCAGGGACAGCCAGC
[G,A]
CCCAGCCCATCACCACTCCCTGGGCTGGCTGGCAGGTATGGCACCCTGGGAGCCCGGCAT
ATACCCAGGGCACCCCTACGGCTGCCGCCAGTCTCATGCCCAGGTGGGTGCTCTGGGCTG
GAGCGAGGGCCAGGTTTTGGGCCGAGGCTTCCCCAGGCAATCCTGTGAGCTCCCTTCTAG
CCTCTGACCCAGTCTGGTCTGGCTTGCATGGATGTAGGGCTTGGGGTGGGAAGTTCAGGT
CCTGGCTTTGCCTTTGCCTGATGTGGATGAGCAGCTCACATGCTCAGGGCCACCTGAGAC

40794
CAGTCTCATGCCCAGGTGGGTGCTCTGGGCTGGAGCGAGGGCCAGGTTTTGGGCCGAGGC
TTCCCCAGGCAATCCTGTGAGCTCCCTTCTAGCCTCTGACCCAGTCTGGTCTGGCTTGCA
TGGATGTAGGGCTTGGGGTGGGAAGTTCAGGTCCTGGCTTTGCCTTTGCCTGATGTGGAT
GAGCAGCTCACATGCTCAGGGCCACCTGAGACTGTCACTGCTCTCCCCTGGCTACTGGGA
GGAGTCACTGAGAGCTTCGTTACCCCTGCTGCCTTGCCCAGGGCACACCCTATACCTCCT
[C,T]
ATCTGCTCTTCCCCTCCCTGCCGCCTTCTGGGCAGGTAGCAGTCCCTGGCCTCTCCCCCT
GGCTGATCACTCTCCCTCAGGCAGTGGAGATCTGCGTCTGGACACCCTCAGATCCTGTCA
TTGCCTGCCCAGAGTCCTTCAGGGGCACCCCTCTGCCTTGGTGTGCGGTCCAGGGCTCTC
ACCCAGGTGCCGCACCCTCTGGGGTCTTCTGTCCAGCTCCCTTGCCCCATGTGCTGTCAC
TGACTCTCCTTGGGACTCGCCTGCCTGCTCAGAGCCCTGCAGGGCTTGGTCAGCTGCCTG

40961
GCCTGATGTGGATGAGCAGCTCACATGCTCAGGGCCACCTGAGACTGTCACTGCTCTCCC
CTGGCTACTGGGAGGAGTCACTGAGAGCTTCGTTACCCCTGCTGCCTTGCCCAGGGCACA
CCCTATACCTCCTCATCTGCTCTTCCCCTCCCTGCCGCCTTCTGGGCAGGTAGCAGTCCC
TGGCCTCTCCCCCTGGCTGATCACTCTCCCTCAGGCAGTGGAGATCTGCGTCTGGACACC
CTCAGATCCTGTCATTGCCTGCCCAGAGTCCTTCAGGGGCACCCCTCTGCCTTGGTGTGC
[A,G]
GTCCAGGGCTCTCACCCAGGTGCCGCACCCTCTGGGGTCTTCTGTCCAGCTCCCTTGCCC
CATGTGCTGTCACTGACTCTCCTTGGGACTCGCCTGCCTGCTCAGAGCCCTGCAGGGCTT
GGTCAGCTGCCTGTTCAGTGTCAACACTTCCCTGCACATCTTAAAACTGGGCTTTATTTT
CGCTGAAGGAACTGTGTTGGGACCCTTGACATCTGTCAGGTTTGCACATGCTGTTTTTTT
TTCTCAGCCCACGTGTTCTCCCCCACGTGGGGTAGCAGCAGGACAGACAGTGAATCACAG

41891
AGGGAAAACAGATATTTTAAGAGATAATAGCATAGCCTATTTTAATATGTTTTAAAGGCC
ATAAGCATATCCAGGAAGATAAATAAACGTGATACAATGTCCACATAGGAGGAACTTTCT
TTCACTGCATTGTTTTCCTTCACAGTGGCCTTCAAGTCACAGGACGCAGCGATTCCCTGC
CCTCTTCGGTGTTATTACACAGGCAGGACTTCAGTGTCAGTATCCCTGCCTTCAGTCTTC
TTTAGAAATCACATCTGTGTTCAATCCATTGTTTAGAGGGAGTGTATTTTTCCTGTTCCA
[C,T]
GAAGAGGACTTTTTGTTCACAATTGGATCACAATGCAGAGGAGTCTGTTCCTCCCCCGTC
GGCTTCTCGGTGCTGGGAGGGTGACCTGTCCCAGATGACTCATCACCCTGACATGCTCTT
GACAAAGGACACCACCAAGAGGAGATGGCAGCTGTACCGGTGCAGCCTCTGTCTGAGGGG
GATATTTGCCTCAGTGTGATTAAAAATCAGTCATGAAAGATTTTTGAATTCAGATTATTT
TTATCAGGAACAGATTTTGAACATCCTGAAATCTTTTCCCTGGCATCATATTAGGTTTTC

FIGURE 3, page 26 of 26

ISOLATED NUCLEIC ACID MOLECULES ENCODING HUMAN LANOSTEROL SYNTHASE PROTEINS, AND RELATED PRODUCTS AND PROCESSES

FIELD OF THE INVENTION

The present invention is in the field of enzyme proteins that are related to the lanosterol synthase enzyme subfamily, recombinant DNA molecules, and protein production. The present invention specifically provides novel peptides and proteins that effect protein phosphorylation and nucleic acid molecules encoding such peptide and protein molecules, all of which are useful in the development of human therapeutics and diagnostic compositions and methods.

BACKGROUND OF THE INVENTION

Many human enzymes serve as targets for the action of pharmaceutically active compounds. Several classes of human enzymes that serve as such targets include helicase, steroid esterase and sulfatase, convertase, synthase, dehydrogenase, monoxygenase, transferase, kinase, glutanase, decarboxylase, isomerase and reductase. It is therefore important in developing new pharmaceutical compounds to identify target enzyme proteins that can be put into high-throughput screening formats. The present invention advances the state of the art by providing novel human drug target enzymes related to the lanosterol synthase subfamily.

Lanosterol Synthase

The novel human protein, and encoding gene, provided by the present invention is related to lanosterol synthase enzymes. Specifically, the protein provided by the present invention is 11 amino acids shorter in exon 4 compared with the art-known lanosterol synthase protein provided in Genbank gi4505027 (see the amino acid sequence alignment of the protein of the present invention against gi4505027 provided in FIG. 2).

Lanosterol synthase enzymes are important for catalyzing the cyclization of squalene-2,3-epoxide lanosterol, which is the parental compound of all mammalian steroids (Young et al., *Human Genet* May 1996;97(5):620–4). Baker et al. (*Biochem Biophys Res Commun* Aug. 4, 1995; 213(1):154–60) cloned and characterized the human lanosterol synthase gene and found that it encoded a predicted 83 kDa protein of 732 amino acids; this amino acid sequence shared 36–40% identity with yeast and plant homologues and 83% identity with *Rattus norvegicus* lanosterol synthase. For a further review of the lanosterol synthase gene/protein, see Sung et al., *Biol Pharm Bull* October 1995; 18(10):1459–61.

Enzyme proteins, particularly members of the lanosterol synthase enzyme subfamily, are a major target for drug action and development. Accordingly, it is valuable to the field of pharmaceutical development to identify and characterize previously unknown members of this subfamily of enzyme proteins. The present invention advances the state of the art by providing previously unidentified human enzyme proteins, and the polynucleotides encoding them, that have homology to members of the lanosterol synthase enzyme subfamily. These novel compositions are useful in the diagnosis, prevention and treatment of biological processes associated with human diseases.

SUMMARY OF THE INVENTION

The present invention is based in part on the identification of amino acid sequences of human enzyme peptides and proteins that are related to the lanosterol synthase enzyme subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate enzyme activity in cells and tissues that express the enzyme. Experimental data as provided in FIG. 1 indicates expression in humans in teratocarcinoma, ovary, uterus, muscle, brain, colon, and hippocampus.

DESCRIPTION OF THE FIGURE SHEETS

FIG. 1 provides the nucleotide sequence of a cDNA molecule that encodes the enzyme protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in humans in teratocarcinoma, ovary, uterus, muscle, brain, colon, and hippocampus.

FIG. 2 provides the predicted amino acid sequence of the enzyme of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the enzyme protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs were identified at 56 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a enzyme protein or part of a enzyme protein and are related to the lanosterol synthase enzyme subfamily. Utilizing these sequences, additional genomic sequences were assembled and transcript and/or cDNA sequences were isolated and characterized. Based on this analysis, the present invention provides amino acid sequences of human enzyme peptides and proteins that are related to the lanosterol synthase enzyme subfamily, nucleic acid sequences in the form of transcript sequences, cDNA sequences and/or genomic sequences that encode these enzyme peptides and proteins, nucleic acid variation (allelic information), tissue distribution of expression, and information about the closest art known protein/peptide/domain that has structural or sequence homology to the enzyme of the present invention.

In addition to being previously unknown, the peptides that are provided in the present invention are selected based on their ability to be used for the development of commercially important products and services. Specifically, the present peptides are selected based on homology and/or structural relatedness to known enzyme proteins of the lanosterol synthase enzyme subfamily and the expression pattern observed. Experimental data as provided in FIG. 1 indicates expression in humans in teratocarcinoma, ovary, uterus, muscle, brain, colon, and hippocampus. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known lanosterol synthase family or subfamily of enzyme proteins.

Specific Embodiments

Peptide Molecules

The present invention provides nucleic acid sequences that encode protein molecules that have been identified as being members of the enzyme family of proteins and are related to the lanosterol synthase enzyme subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the enzyme peptides of the present invention, enzyme peptides, or peptides/proteins of the present invention.

The present invention provides isolated peptide and protein molecules that consist of, consist essentially of, or comprise the amino acid sequences of the enzyme peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the enzyme peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated enzyme peptide can be purified from cells that naturally express it, purified from cells that have been altered to express it (recombinant), or synthesized using known protein synthesis methods. Experimental data as provided in FIG. 1 indicates expression in humans in teratocarcinoma, ovary, uterus, muscle, brain, colon, and hippocampus. For example, a nucleic acid molecule encoding the enzyme peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the enzyme peptides of the present invention are the naturally occurring mature proteins. A brief description of how various types of these proteins can be made/isolated is provided below.

The enzyme peptides of the present invention can be attached to heterologous sequences to form chimeric or fusion proteins. Such chimeric and fusion proteins comprise a enzyme peptide operatively linked to a heterologous protein having an amino acid sequence not substantially homologous to the enzyme peptide. "Operatively linked" indicates that the enzyme peptide and the heterologous protein are fused in-frame. The heterologous protein can be fused to the N-terminus or C-terminus of the enzyme peptide.

In some uses, the fusion protein does not affect the activity of the enzyme peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant enzyme peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., *Current Protocols in Molecular Biology,* 1992). Moreover, many expression vectors are commercially available that already encode a fusion moiety (e.g., a GST protein). A enzyme peptide-encoding nucleic acid can be cloned into such an expression vector such that the fusion moiety is linked in-frame to the enzyme peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the enzyme peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A.M, ed., Oxford University Press, New York, 1988; *Biocomputing: Informatics and Genome Projects,* Smith, D. W., ed., Academic Press, New York, 1993; *Computer Analysis of Sequence Data, Part* 1, Griffin, A. M., and Griffin, H. G. eds., Humana Press, New Jersey, 1994; *Sequence Analysis in Molecular Biology,* von Heinje, G. Academic Press, 1987; and *Sequence Analysis Primer,* Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package, using either a Blossom 62 matrix or a PAM250 matrix, and a gap weight of 16, 14, 12, 10, 8, 6, or 4 and a length-weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS; 4:11–17 (1989)) which has been incorporated into the ALIGN program (version 2.0), using a PAMI20 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the enzyme peptides of the present invention as well as being encoded by the same genetic locus as the enzyme peptide provided herein. The gene encoding the novel enzyme of the present invention is located on a genome component that has been mapped to human chromosome 21 (as indicated in FIG. 3), which is supported by multiple lines of evidence, such as STS and BAC map data.

Allelic variants of a enzyme peptide can readily be identified as being a human protein having a high degree (significant) of sequence homology/identity to at least a portion of the enzyme peptide as well as being encoded by the same genetic locus as the enzyme peptide provided herein. Genetic locus can readily be determined based on the genomic information provided in FIG. 3, such as the genomic sequence mapped to the reference human. The gene encoding the novel enzyme of the present invention is located on a genome component that has been mapped to human chromosome 21 (as indicated in FIG. 3), which is supported by multiple lines of evidence, such as STS and BAC map data. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a enzyme peptide encoding nucleic acid molecule under stringent conditions as more fully described below.

FIG. 3 provides information on SNPs that have been found in the gene encoding the enzyme of the present invention. SNPs were identified at 56 different nucleotide positions, including a non-synonymous coding SNP at position 36001 (protein position 631). Changes in the amino acid sequence caused by these SNPs is indicated in FIG. 3 and can readily be determined using the universal genetic code and the protein sequence provided in FIG. 2 as a reference. Some of these SNPs, located outside the ORF and in introns, may affect gene transcription.

Paralogs of a enzyme peptide can readily be identified as having some degree of significant sequence homology/identity to at least a portion of the enzyme peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a enzyme peptide encoding nucleic acid molecule under moderate to stringent conditions as more fully described below.

Orthologs of a enzyme peptide can readily be identified as having some degree of significant sequence homology/identity to at least a portion of the enzyme peptide as well as being encoded by a gene from another organism. Preferred orthologs will be isolated from mammals, preferably primates, for the development of human therapeutic targets and agents. Such orthologs will be encoded by a nucleic acid sequence that will hybridize to a enzyme peptide encoding nucleic acid molecule under moderate to stringent conditions, as more fully described below, depending on the degree of relatedness of the two organisms yielding the proteins.

Non-naturally occurring variants of the enzyme peptides of the present invention can readily be generated using recombinant techniques. Such variants include, but are not limited to deletions, additions and substitutions in the amino acid sequence of the enzyme peptide. For example, one class of substitutions are conserved amino acid substitution. Such substitutions are those that substitute a given amino acid in a enzyme peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant enzyme peptides can be fully functional or can lack function in one or more activities, e.g. ability to bind substrate, ability to phosphorylate substrate, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as enzyme activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention farther provides fragments of the enzyme peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a enzyme peptide. Such fragments can be chosen based on the ability to retain one or more of the biological activities of the enzyme peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the enzyme peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in enzyme peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties,* 2nd Ed., T. E. Creighton, W. H. Freeman and Company, New York (1993). Many detailed reviews are available on this subject, such as by Wold, F., *Posttranslational Covalent Modification of Proteins,* B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the enzyme peptides of the present invention also encompass derivatives or analogs in which a substituted amino acid residue is not one encoded by the genetic code, in which a substituent group is included, in which the mature enzyme peptide is fused with another compound, such as a compound to increase the half-life of the enzyme peptide (for example, polyethylene glycol), or in which the additional amino acids are fused to the mature enzyme peptide, such as a leader or secretory sequence or a sequence for purification of the mature enzyme peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a enzyme-effector protein interaction or enzyme-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

The potential uses of the peptides of the present invention are based primarily on the source of the protein as well as the class/action of the protein. For example, enzymes isolated from humans and their human/mammalian orthologs serve as targets for identifying agents for use in mammalian therapeutic applications, e.g. a human drug, particularly in modulating a biological or pathological response in a cell or tissue that expresses the enzyme. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus. A large percentage of pharmaceutical agents are being developed that modulate the activity of enzyme proteins, particularly members of the lanosterol synthase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in humans in teratocarcinoma, ovary, uterus, muscle, brain, colon, and hippocampus. Such uses can readily be determined using the information provided herein, that which is known in the art, and routine experimentation.

The proteins of the present invention (including variants and fragments that may have been disclosed prior to the present invention) are useful for biological assays related to enzymes that are related to members of the lanosterol synthase subfamily. Such assays involve any of the known enzyme functions or activities or properties useful for diagnosis and treatment of enzyme-related conditions that are specific for the subfamily of enzymes that the one of the present invention belongs to, particularly in cells and tissues that express the enzyme. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus.

The proteins of the present invention are also useful in drug screening assays, in cell-based or cell-free systems. Cell-based systems can be native, i.e., cells that normally express the enzyme, as a biopsy or expanded in cell culture. Experimental data as provided in FIG. 1 indicates expression in humans in teratocarcinoma, ovary, uterus, muscle, brain, colon, and hippocampus. In an alternate embodiment, cell-based assays involve recombinant host cells expressing the enzyme protein.

The polypeptides can be used to identify compounds that modulate enzyme activity of the protein in its natural state or an altered form that causes a specific disease or pathology associated with the enzyme. Both the enzymes of the present invention and appropriate variants and fragments can be used in high-throughput screens to assay candidate compounds for the ability to bind to the enzyme. These compounds can be further screened against a functional enzyme to determine the effect of the compound on the enzyme activity. Further, these compounds can be tested in animal or invertebrate systems to determine activity/effectiveness. Compounds can be identified that activate (agonist) or inactivate (antagonist) the enzyme to a desired degree.

Further, the proteins of the present invention can be used to screen a compound for the ability to stimulate or inhibit interaction between the enzyme protein and a molecule that normally interacts with the enzyme protein, e.g. a substrate or a component of the signal pathway that the enzyme protein normally interacts (for example, another enzyme). Such assays typically include the steps of combining the enzyme protein with a candidate compound under conditions that allow the enzyme protein, or fragment, to interact with the target molecule, and to detect the formation of a complex between the protein and the target or to detect the biochemical consequence of the interaction with the enzyme protein and the target, such as any of the associated effects of signal transduction such as protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., *Nature* 354:82–84 (1991); Houghten et al., *Nature* 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., *Cell* 72:767–778 (1993)); 3) antibodies (e.g., polyclonal, monoclonal, humanized, anti-idiotypic, chimeric, and single chain antibodies as well as Fab, $F(ab')_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant enzymes or appropriate fragments containing mutations that affect enzyme function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) enzyme activity. The assays typically involve an assay of events in the signal transduction pathway that indicate enzyme activity. Thus, the phosphorylation of a substrate, activation of a protein, a change in the expression of genes that are up- or down-regulated in response to the enzyme protein dependent signal cascade can be assayed.

Any of the biological or biochemical functions mediated by the enzyme can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the enzyme can be assayed. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus.

Binding and/or activating compounds can also be screened by using chimeric enzyme proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native enzyme. Accordingly, a different set of signal transduction components is available as an end-point assay for activation. This allows for assays to be performed in other than the specific host cell from which the enzyme is derived.

The proteins of the present invention are also useful in competition binding assays in methods designed to discover compounds that interact with the enzyme (e.g. binding partners and/or ligands). Thus, a compound is exposed to a enzyme polypeptide under conditions that allow the compound to bind or to otherwise interact with the polypeptide. Soluble enzyme polypeptide is also added to the mixture. If the test compound interacts with the soluble enzyme polypeptide, it decreases the amount of complex formed or activity from the enzyme target. This type of assay is particularly useful in cases in which compounds are sought that interact with specific regions of the enzyme. Thus, the soluble polypeptide that competes with the target enzyme region is designed to contain peptide sequences corresponding to the region of interest.

To perform cell free drug screening assays, it is sometimes desirable to immobilize either the enzyme protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}S$-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of enzyme-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a enzyme-binding protein and a candidate compound are incubated in the enzyme protein-presenting wells and the amount of complex trapped in the well can be quantitated. Methods for detecting such complexes, in addition to those described above for the GST-immobilized complexes, include immunodetection of complexes using antibodies reactive with the enzyme protein target molecule, or which are reactive with enzyme protein and compete with the target molecule, as well as enzyme-linked assays which rely on detecting an enzymatic activity associated with the target molecule.

Agents that modulate one of the enzymes of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of enzyme protein activity identified according to these drug screening assays can be used to treat a subject with a disorder mediated by the enzyme pathway, by treating cells or tissues that express the enzyme. Experimental data as provided in FIG. 1 indicates expression in humans in teratocarcinoma, ovary, uterus, muscle, brain, colon, and hippocampus. These methods of treatment include the steps of administering a modulator of enzyme activity in a pharmaceutical composition to a subject in need of such treatment, the modulator being identified as described herein.

In yet another aspect of the invention, the enzyme proteins can be used as "bait proteins" in a two-hybrid assay or three-hybrid assay (see, e.g., U.S. Pat. No. 5,283,317; Zervos et al. (1993) *Cell* 72:223–232; Madura et al. (1993) *J. Biol. Chem.* 268:12046–12054; Bartel et al. (1993) *Biotechniques* 14:920–924; Iwabuchi et al. (1993) *Oncogene* 8:1693–1696; and Brent WO94/10300), to identify other proteins, which bind to or interact with the enzyme and are involved in enzyme activity. Such enzyme-binding proteins are also likely to be involved in the propagation of signals by the enzyme proteins or enzyme targets as, for example, downstream elements of a enzyme-mediated signaling pathway. Alternatively, such enzyme-binding proteins are likely to be enzyme inhibitors.

The two-hybrid system is based on the modular nature of most transcription factors, which consist of separable DNA-binding and activation domains. Briefly, the assay utilizes two different DNA constructs. In one construct, the gene that codes for a enzyme protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a enzyme-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the enzyme protein.

This invention further pertains to novel agents identified by the above-described screening assays. Accordingly, it is within the scope of this invention to further use an agent identified as described herein in an appropriate animal model. For example, an agent identified as described herein (e.g., a enzyme-modulating agent, an antisense enzyme nucleic acid molecule, a enzyme-specific antibody, or a enzyme-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The enzyme proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in humans in teratocarcinoma, ovary, uterus, muscle, brain, colon, and hippocampus. The method involves contacting a biological sample with a compound capable of interacting with the enzyme protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered enzyme activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the enzyme protein in which one or more of the enzyme functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and enzyme activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in humans in teratocarcinoma, ovary, uterus, muscle, brain, colon, and hippocampus. Accordingly, methods for treatment include the use of the enzyme protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the enzyme proteins. Antibodies can be prepared from any region of the peptide as described herein. However, preferred regions will include those involved in function/activity and/or enzyme/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in humans in teratocarcinoma, ovary, uterus, muscle, brain, colon, and hippocampus. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in humans in teratocarcinoma, ovary, uterus, muscle, brain, colon, and hippocampus. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in humans in teratocarcinoma, ovary, uterus, muscle, brain, colon, and hippocampus. Thus, where a specific protein has been correlated with expression in a specific tissue, antibodies that are specific for this protein can be used to identify a tissue type.

The antibodies are also useful for inhibiting protein function, for example, blocking the binding of the enzyme peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nuleic acid arrays and similar methods have been developed for antibody arrays.

Nucleic Acid Molecules

The present invention further provides isolated nucleic acid molecules that encode a enzyme peptide or protein of the present invention (cDNA, transcript and genomic sequence). Such nucleic acid molecules will consist of, consist essentially of, or comprise a nucleotide sequence that encodes one of the enzyme peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the enzyme peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (anti-sense strand).

The invention further provides nucleic acid molecules that encode fragments of the peptides of the present invention as well as nucleic acid molecules that encode obvious variants of the enzyme proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. The gene encoding the novel enzyme of the present invention is located on a genome component that has been mapped to human chromosome 21 (as indicated in FIG. 3), which is supported by multiple lines of evidence, such as STS and BAC map data.

FIG. 3 provides information on SNPs that have been found in the gene encoding the enzyme of the present invention. SNPs were identified at 56 different nucleotide positions, including a non-synonymous coding SNP at position 36001 (protein position 631). Changes in the amino acid sequence caused by these SNPs is indicated in FIG. 3 and can readily be determined using the universal genetic code and the protein sequence provided in FIG. 2 as a reference. Some of these SNPs, located outside the ORF and in introns, may affect gene transcription.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6×sodium chloride/sodium citrate (SSC) at about 45 C, followed by one or more washes in 0.2×SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs were identified at 56 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. The gene encoding the novel enzyme of the present invention is located on a genome component that has been mapped to human chromosome 21 (as indicated in FIG. 3), which is supported by multiple lines of evidence, such as STS and BAC map data.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in enzyme protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a enzyme protein, such as by measuring a level of a enzyme-encoding nucleic acid in a sample of cells from a subject e.g., mRNA or genomic DNA, or determining if a enzyme gene has been mutated. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus.

Nucleic acid expression assays are useful for drug screening to identify compounds that modulate enzyme nucleic acid expression.

The invention thus provides a method for identifying a compound that can be used to treat a disorder associated with nucleic acid expression of the enzyme gene, particularly biological and pathological processes that are mediated by the enzyme in cells and tissues that express it. Experimental data as provided in FIG. 1 indicates expression in humans in teratocarcinoma, ovary, uterus, muscle, brain, colon, and hippocampus. The method typically includes assaying the ability of the compound to modulate the expression of the enzyme nucleic acid and thus identifying a compound that can be used to treat a disorder characterized by undesired enzyme nucleic acid expression. The assays can be performed in cell-based and cell-free systems. Cell-based assays include cells naturally expressing the enzyme nucleic acid or recombinant cells genetically engineered to express specific nucleic acid sequences.

The assay for enzyme nucleic acid expression can involve direct assay of nucleic acid levels, such as mRNA levels, or on collateral compounds involved in the signal pathway. Further, the expression of genes that are up- or down-regulated in response to the enzyme protein signal pathway can also be assayed. In this embodiment the regulatory regions of these genes can be operably linked to a reporter gene such as luciferase.

Thus, modulators of enzyme gene expression can be identified in a method wherein a cell is contacted with a candidate compound and the expression of mRNA determined. The level of expression of enzyme mRNA in the presence of the candidate compound is compared to the level of expression of enzyme mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate enzyme nucleic acid expression in cells and tissues that express the enzyme. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus. Modulation includes both up-regulation (i.e. activation or agonization) or down-regulation (suppression or antagonization) or nucleic acid expression.

Alternatively, a modulator for enzyme nucleic acid expression can be a small molecule or drug identified using the screening assays described herein as long as the drug or small molecule inhibits the enzyme nucleic acid expression in the cells and tissues that express the protein. Experimental data as provided in FIG. 1 indicates expression in humans in teratocarcinoma, ovary, uterus, muscle, brain, colon, and hippocampus.

The nucleic acid molecules are also useful for monitoring the effectiveness of modulating compounds on the expression or activity of the enzyme gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in enzyme nucleic acid expression, and particularly in qualitative changes that lead to pathology. The nucleic acid molecules can be used to detect mutations in enzyme genes and gene expression products such as mRNA. The nucleic acid molecules can be used as hybridization probes to detect naturally occurring genetic mutations in the enzyme gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the enzyme gene associated with a dysfunction provides a diagnostic tool for an active disease or susceptibility to disease when the disease results from overexpression, underexpression, or altered expression of a enzyme protein.

Individuals carrying mutations in the enzyme gene can be detected at the nucleic acid level by a variety of techniques. FIG. 3 provides information on SNPs that have been found in the gene encoding the enzyme of the present invention. SNPs were identified at 56 different nucleotide positions, including a non-synonymous coding SNP at position 36001 (protein position 631). Changes in the amino acid sequence caused by these SNPs is indicated in FIG. 3 and can readily be determined using the universal genetic code and the protein sequence provided in FIG. 2 as a reference. Some of these SNPs, located outside the ORF and in introns, may affect gene transcription. The gene encoding the novel enzyme of the present invention is located on a genome component that has been mapped to human chromosome 21 (as indicated in FIG. 3), which is supported by multiple lines of evidence, such as STS and BAC map data. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a enzyme gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant enzyme gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the enzyme gene in an individual in order to select an appropriate compound or dosage regimen for treatment. FIG. 3 provides information on SNPs that have been found in the gene encoding the enzyme of the present invention. SNPs were identified at 56 different nucleotide positions, including a non-synonymous coding SNP at position 36001 (protein position 631). Changes in the amino acid sequence caused by these SNPs is indicated in FIG. 3 and can readily be determined using the universal genetic code and the protein sequence provided in FIG. 2 as a reference. Some of these SNPs, located outside the ORF and in introns, may affect gene transcription.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control enzyme gene expression in cells, tissues, and organisms. A DNA antisense nucleic acid molecule is designed to be complementary to a region of the gene involved in transcription, preventing transcription and hence production of enzyme protein. An antisense RNA or DNA nucleic acid molecule would hybridize to the mRNA and thus block translation of mRNA into enzyme protein.

Alternatively, a class of antisense molecules can be used to inactivate mRNA in order to decrease expression of enzyme nucleic acid. Accordingly, these molecules can treat a disorder characterized by abnormal or undesired enzyme nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the enzyme protein, such as substrate binding.

The nucleic acid molecules also provide vectors for gene therapy in patients containing cells that are aberrant in enzyme gene expression. Thus, recombinant cells, which include the patient's cells that have been engineered ex vivo and returned to the patient, are introduced into an individual where the cells produce the desired enzyme protein to treat the individual.

The invention also encompasses kits for detecting the presence of a enzyme nucleic acid in a biological sample. Experimental data as provided in FIG. 1 indicates that the enzymes of the present invention are expressed in humans in teratocarcinoma, ovary, uterus, muscle, brain, and colon, as indicated by virtual northern blot analysis. In addition, PCR-based tissue screening panels indicate expression in the hioppocampus. For example, the kit can comprise reagents such as a labeled or labelable nucleic acid or agent capable of detecting enzyme nucleic acid in a biological sample; means for determining the amount of enzyme nucleic acid in the sample; and means for comparing the amount of enzyme nucleic acid in the sample with a standard. The compound or agent can be packaged in a suitable container. The kit can further comprise instructions for using the kit to detect enzyme protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the enzyme proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the enzyme gene of the present invention. FIG. 3 provides information on SNPs that have been found in the gene encoding the enzyme of the present invention. SNPs were identified at 56 different nucleotide positions, including a non-synonymous coding SNP at position 36001 (protein position 631). Changes in the amino acid sequence caused by these SNPs is indicated in FIG. 3 and can readily be determined using the universal genetic code and the protein sequence provided in FIG. 2 as a reference. Some of these SNPs, located outside the ORF and in introns, may affect gene transcription.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques,* Elsevier Science Publishers, Amsterdam, The Netherlands (1986); Bullock, G. R. et al., *Techniques in Immunocytochemistry,* Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology,* Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified enzyme gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extrachromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli,* the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.,* Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd ed.,* Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli,* Streptomyces, and *Salmonella typhimurium.* Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroenzyme. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli.* (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kuijan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed., Cold Spring Harbor Laboratory,* Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed.,* Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as enzymes, appropriate secretion signals are incorporated into the vector. The signal sequence can be endogenous to the peptides or heterologous to these peptides.

Where the peptide is not secreted into the medium, which is typically the case with enzymes, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a enzyme protein or peptide that can be further purified to produce desired amounts of enzyme protein or fragments. Thus, host cells containing expression vectors are useful for peptide production.

Host cells are also useful for conducting cell-based assays involving the enzyme protein or enzyme protein fragments, such as those described above as well as other formats known in the art. Thus, a recombinant host cell expressing a native enzyme protein is useful for assaying compounds that stimulate or inhibit enzyme protein function.

Host cells are also useful for identifying enzyme protein mutants in which these functions are affected. If the mutants naturally occur and give rise to a pathology, host cells containing the mutations are useful to assay compounds that have a desired effect on the mutant enzyme protein (for example, stimulating or inhibiting function) which may not be indicated by their effect on the native enzyme protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a enzyme protein and identifying and evaluating modulators of enzyme protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the enzyme protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the enzyme protein to particular cells.

Methods for generating transgenic animals via embryo manipulation and nmicroinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo,* (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, enzyme protein activation, and signal transduction, may not be evident from in vitro cell-free or cell-based assays. Accordingly, it is useful to provide non-human transgenic animals to assay in vivo enzyme protein function, including substrate interaction, the effect of specific mutant enzyme proteins on enzyme protein function and substrate interaction, and the effect of chimeric enzyme proteins. It is also possible to assess the effect of null mutations, that is, mutations that substantially or completely eliminate one or more enzyme protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule comprising a nucleotide sequence selected from the group consisting of:

(a) a cDNA sequence that encodes SEQ ID NO:2;

(b) SEQ ID NO:1;

(c) nucleotides 34–2196 of SEQ ID NO:1; and (d) a nucleotide sequence that is completely complementary to a nucleotide sequence of any of (a)–(c).

2. A nucleic acid vector comprising the nucleic acid molecule of claim 1.

3. The vector of claim 2, wherein said vector is selected from the group consisting of a plasmid, a virus, and a bacteriophage.

4. The vector of claim 2, wherein said isolated nucleic acid molecule is inserted into said vector in proper orientation and correct reading frame such that a polypeptide comprising SEQ ID NO:2 may be expressed by a cell transformed with said vector.

5. The vector of claim 4, wherein said isolated nucleic acid molecule is operatively linked to a promoter sequence.

6. A host cell containing the vector of claim 2.

7. A process for producing a polypeptide comprising culturing the host cell of claim 6 under conditions sufficient for the production of the polypeptide encoded by the vector, and recovering said polypeptide.

8. An isolated nucleic acid molecule consisting of a nucleotide sequence selected from the group consisting of:

(a) a nucleotide sequence that encodes a polypeptide comprising the amino acid sequence of SEQ ID NO:2;

(b) a nucleotide sequence consisting of SEQ ID NO:1;

(c) a nucleotide sequence consisting of SEQ ID NO:3; and (d) a nucleotide sequence that is completely complementary to a nucleotide sequence of any of (a)–(c).

9. A nucleic acid vector comprising the nucleic acid molecule of claim 8.

10. The vector of claim 9, wherein said vector is selected from the group consisting of a plasmid, a virus, and a bacteriophage.

11. The vector of claim 9, wherein said isolated nucleic acid molecule is inserted into said vector in proper orientation and correct reading frame such that a polypeptide comprising SEQ ID NO:2 may be expressed by a cell transformed with said vector.

12. The vector of claim 11, wherein said isolated nucleic acid molecule is operatively linked to a promoter sequence.

13. A host cell containing the vector of claim 9.

14. A process for producing a polypeptide comprising culturing the host cell of claim 13 under conditions sufficient for the production of the polypeptide encoded by the vector, and recovering said polypeptide.

15. An isolated nucleic acid molecule consisting of a nucleotide sequence selected from the group consisting of:

(a) a nucleotide sequence that encodes a polypeptide comprising the amino acid sequence of SEQ ID NO:2, except that residue 631 of SEQ ID NO:2 is leucine; and (b) a nucleotide sequence that is completely complementary to a nucleotide sequence of (a).

16. A nucleic acid vector comprising the nucleic acid molecule of claim 15.

17. The vector of claim 16, wherein said vector is selected from the group consisting of a plasmid, a virus, and a bacteriophage.

18. The vector of claim 16, wherein said isolated nucleic acid molecule is inserted into said vector in proper orientation and correct reading frame such that a polypeptide comprising SEQ ID NO:2, except that residue 631 of SEQ ID NO:2 is leucine, may be expressed by a cell transformed with said vector.

19. The vector of claim 18, wherein said isolated nucleic acid molecule is operatively linked to a promoter sequence.

20. A host cell containing the vector of claim 16.

21. A process for producing a polypeptide comprising culturing the host cell of claim 20 under conditions sufficient for the production of the polypeptide encoded by the vector, and recovering said polypeptide.

22. An isolated polynucleotide consisting of the nucleotide sequence of SEQ ID NO:1.

23. An isolated polynucleotide consisting of the nucleotide sequence of SEQ ID NO:3.

* * * * *

SEQUENCE LISTING

```
<160> NUMBER OF SEQ ID NOS: 4

<210> SEQ ID NO 1
<211> LENGTH: 4239
<212> TYPE: DNA
<213> ORGANISM: Human

<400> SEQUENCE: 1

tggcagtggg cggcgtagag cactgcagca gcaatgacgg agggcacgtg tctgcggcgc      60

cgagggggcc cctacaagac cgagcccgcc accgacctcg gccgctggcg actcaactgc     120

gagaggggcc ggcagacgtg gacctacctg caggacgagc gcgccggccg cgagcagacc     180

ggcctggaag cctacgccct ggggctggac accaagaatt actttaagga cttgcccaaa     240

gcccacaccg cctttgaggg ggctctgaac gggatgacat tttacgtggg gctgcaggct     300

gaggatgggc actggacggg tgattatggt ggcccacttt tcctcctgcc aggcctcctg     360

atcacttgcc acgtggcacg catccctctg ccagccggat acagagaaga gattgtgcgg     420

tacctgcggc acattgagga taagtccacc gtgtttggga ctgcgctcaa ctatgtgtct     480

ctcagaattc tgggtgttgg gcctgacgat cctgacctgg tacgagcccg gaacattctt     540

cacaagaaag gtggtgctgt ggccatcccc tcctggggga agttctggct ggctgtcctg     600

aatgtttaca gctgggaagg cctcaatacc ctgttcccag agatgtggct gtttcctgac     660

tgggcaccgg cacacccctc cacactctgg tgccactgcc ggcaggtgta cctgcccatg     720

agctactgct acgccgttcg gctgagtgcc gcggaagacc cgctggtcca gagcctccgc     780

caggagctct atgtggagga cttcgccagc attgactggc tggcgcagag gaacaacgtg     840

gcccccgacg agctgtacac gccgcacagc tggctgctcc gcgtggtata tgcgctcctc     900

aacctgtatg agcaccacca cagtgcccac ctgcggcagc gggccgtgca gaagctgtat     960

gaacacattg tggccgacga ccgattcacc aagagcatca gcatcggccc gatctcgaaa    1020

accatcaaca tgcttgtgcg ctggtatgtg gacgggcccg cctccactgc cttccaggag    1080

catgtctcca gaatcccgga ctatctctgg atgggccttg acggcatgaa aatgcagggc    1140
```

-continued

```
accaacggct cacagatctg ggacaccgca ttcgccatcc aggctctgct tgaggcgggc   1200
gggcaccaca ggcccgagtt ttcgtcctgc ctgcagaagg ctcatgagtt cctgaggctc   1260
tcacaggtcc cagataaccc tcccgactac cagaagtact accgccagat gcgcaagggt   1320
ggcttctcct tcagtacgct ggactgcggc tggatcgttt ctgactgcac ggctgaggcc   1380
ttgaaggctg tgctgctcct gcaggagaag tgtccccatg tcaccgagca catccccaga   1440
gaacggctct gcgatgctgt ggctgtgctg ctgaacatga gaaatccaga tggagggttc   1500
gccacctatg agaccaagcg tggggggcac ttgctggagc tgctgaaccc ctcggaggtc   1560
ttcggggaca tcatgattga ctacacctat gtggagtgca cctcagccgt gatgcaggcg   1620
cttaagtatt tccacaagcg tttcccggag cacagggcag cggagatccg ggagaccctc   1680
acgcagggct tagagttctg tcggcggcag cagagggccg atggctcctg ggaaggctcc   1740
tggggagttt gcttcaccta cggcacctgg tttggcctgg aggccttcgc ctgtatgggg   1800
cagacctacc gagatgggac tgcctgtgca gaggtctccc gggcctgtga cttcctgctg   1860
tcccggcaga tggcagacgg aggctggggg gaggactttg agtcctgcga ggagcggcgt   1920
tatgtgcaga gtgcccagtc ccagatccac aacacatgct gggccatgat ggggctgatg   1980
gccgttcggc atcctgacat cgaggcccag gagagaggag tccggtgtct acttgagaaa   2040
cagctcccca atggcgactg gccgcaggaa aacattgctg ggtcttcaa caagtcctgt   2100
gccatctcct acacgagcta caggaacatc ttccccatct gggccctcgg ccgcttctcc   2160
cagctgtacc ctgagagagc ccttgctggc cacccctgag aacatgccta cctgctgggt   2220
gccgtctgtg cgttccagtg aggccaaggg gtcctggccg ggttggggag ccctcccata   2280
accctgtctt gggctccaac cctcaacct ctatctcata gatgtgaatc tgggggccag   2340
gctggaggca gggatgggga cagggtgggt ggcttagact cttgattttt actgtaggtt   2400
catttctgaa agtagcttgt cggcttgggg tgaggaaggg ggcacaggag ccgtgacccc   2460
tgaggaggca cagcgccttc tgccacctct gggcacggcc tcaaggtagt gaggctagga   2520
ggtttttct gaccaatagc tgagttcttg ggagaggagc agctgtgcct gtgtgattcc   2580
ttagtgtcga gtgggctctg ggctggggtc ggccctgggc aggcttctcc tgcacctttt   2640
gtctgctggg ctgagggaca cgagggcaac cctgtgacaa tggcaggtag tgtgcatccg   2700
tgaatagccc agtgcggggg ttgctcatgg agcatcctga ggccgtgcag cagggagccc   2760
catgcccctg ggtcgtgagc ttgcctgcgt atggggtggt gtcatggagc ctcatgcccc   2820
tgggtcgtga gctcgcctga gtatggggtg gtgtcatgga gccgcatacc cctgggttgt   2880
gagctcgcct gcatatgcag ggtctgtcat ggaacatccc aagtctgtgc agcagggagc   2940
cccatgcccc tgggacatga acccacctgc gtggaatgct gtttgtgagg tgtctacagg   3000
gtttatagta gtcttgtgga cacagaaatg cacaggggac acttacggac acagaaatgc   3060
acaggggagg ccgagcataa ccaggggtga ggggcaggca gcagttgtag ttactgccgc   3120
ggggcactgc tatgtgcagg gacagccagc gcccagccca tcaccactcc ctgggctggc   3180
tggcaggtat ggcaccctgg gagcccggca tatacccagg gcacccctac ggctgccgcc   3240
agtctcatgc ccaggtgggt gctctgggct ggagcgaggg ccaggttttg ggccgaggct   3300
tccccaggca atcctgtgag ctcccttcta gcctctgacc cagtctggtc tggcttgcat   3360
ggatgtaggg cttggggtgg gaagttcagg tcctggcttt gcctttgcct gatgtggatg   3420
agcagctcac atgctcaggg ccacctgaga ctgtcactgc tctcccctgg ctactgggag   3480
```

-continued

```
gagtcactga gagcttcgtt acccctgctg ccttgcccag ggcacaccct atacctcctc   3540

atctgctctt cccctccctg ccgccttctg ggcaggtagc agtccctggc ctctcccccct  3600

ggctgatcac tctccctcag gcagtggaga tctgcgtctg gacaccctca gatcctgtca   3660

ttgcctgccc agagtccttc aggggcaccc ctctgccttg gtgtgcggtc cagggctctc   3720

acccaggtgc cgcaccctct ggggtcttct gtccagctcc cttgccccat gtgctgtcac   3780

tgactctcct tgggactcgc ctgcctgctc agagccctgc agggcttggt cagctgcctg   3840

ttcagtgtca acacttccct gcacatctta aaactgggct ttattttcgc tgaaggaact   3900

gtgttgggac ccttgacatc tgtcaggttt gcacatgctg ttttttttc tcagcccacg   3960

tgttctcccc cacgtggggt agcagcagga cagacagtga atcacagagt ctgccctgag   4020

cagaggctgc tgtccctggg actcctagcc atggtcagac tgtacaaaac ggttttccag   4080

aaatgaaatg taaatccatt tttatactga aaatgttact gaaagtcact tttatgagca   4140

tctgccttaa taaacagaca ttgattccct taaaaaaaaa aaaaaaaaaa aaaaaaaaaa   4200

aaaaaaaaaa aaaaaaaaaa aaaaaaaaaa aaaaaaaaa                          4239
```

<210> SEQ ID NO 2
<211> LENGTH: 721
<212> TYPE: PRT
<213> ORGANISM: Human

<400> SEQUENCE: 2

```
Met Thr Glu Gly Thr Cys Leu Arg Arg Arg Gly Gly Pro Tyr Lys Thr
 1               5                  10                  15

Glu Pro Ala Thr Asp Leu Gly Arg Trp Arg Leu Asn Cys Glu Arg Gly
            20                  25                  30

Arg Gln Thr Trp Thr Tyr Leu Gln Asp Glu Arg Ala Gly Arg Glu Gln
        35                  40                  45

Thr Gly Leu Glu Ala Tyr Ala Leu Gly Leu Asp Thr Lys Asn Tyr Phe
    50                  55                  60

Lys Asp Leu Pro Lys Ala His Thr Ala Phe Glu Gly Ala Leu Asn Gly
65                  70                  75                  80

Met Thr Phe Tyr Val Gly Leu Gln Ala Glu Asp Gly His Trp Thr Gly
                85                  90                  95

Asp Tyr Gly Gly Pro Leu Phe Leu Leu Pro Gly Leu Leu Ile Thr Cys
            100                 105                 110

His Val Ala Arg Ile Pro Leu Pro Ala Gly Tyr Arg Glu Glu Ile Val
        115                 120                 125

Arg Tyr Leu Arg His Ile Glu Asp Lys Ser Thr Val Phe Gly Thr Ala
    130                 135                 140

Leu Asn Tyr Val Ser Leu Arg Ile Leu Gly Val Gly Pro Asp Asp Pro
145                 150                 155                 160

Asp Leu Val Arg Ala Arg Asn Ile Leu His Lys Lys Gly Gly Ala Val
                165                 170                 175

Ala Ile Pro Ser Trp Gly Lys Phe Trp Leu Ala Val Leu Asn Val Tyr
            180                 185                 190

Ser Trp Glu Gly Leu Asn Thr Leu Phe Pro Glu Met Trp Leu Phe Pro
        195                 200                 205

Asp Trp Ala Pro Ala His Pro Ser Thr Leu Trp Cys His Cys Arg Gln
    210                 215                 220

Val Tyr Leu Pro Met Ser Tyr Cys Tyr Ala Val Arg Leu Ser Ala Ala
225                 230                 235                 240
```

-continued

```
Glu Asp Pro Leu Val Gln Ser Leu Arg Gln Glu Leu Tyr Val Glu Asp
                245                 250                 255

Phe Ala Ser Ile Asp Trp Leu Ala Gln Arg Asn Asn Val Ala Pro Asp
            260                 265                 270

Glu Leu Tyr Thr Pro His Ser Trp Leu Leu Arg Val Val Tyr Ala Leu
        275                 280                 285

Leu Asn Leu Tyr Glu His His His Ser Ala His Leu Arg Gln Arg Ala
    290                 295                 300

Val Gln Lys Leu Tyr Glu His Ile Val Ala Asp Asp Arg Phe Thr Lys
305                 310                 315                 320

Ser Ile Ser Ile Gly Pro Ile Ser Lys Thr Ile Asn Met Leu Val Arg
                325                 330                 335

Trp Tyr Val Asp Gly Pro Ala Ser Thr Ala Phe Gln Glu His Val Ser
            340                 345                 350

Arg Ile Pro Asp Tyr Leu Trp Met Gly Leu Asp Gly Met Lys Met Gln
        355                 360                 365

Gly Thr Asn Gly Ser Gln Ile Trp Asp Thr Ala Phe Ala Ile Gln Ala
    370                 375                 380

Leu Leu Glu Ala Gly Gly His His Arg Pro Glu Phe Ser Ser Cys Leu
385                 390                 395                 400

Gln Lys Ala His Glu Phe Leu Arg Leu Ser Gln Val Pro Asp Asn Pro
                405                 410                 415

Pro Asp Tyr Gln Lys Tyr Tyr Arg Gln Met Arg Lys Gly Gly Phe Ser
            420                 425                 430

Phe Ser Thr Leu Asp Cys Gly Trp Ile Val Ser Asp Cys Thr Ala Glu
        435                 440                 445

Ala Leu Lys Ala Val Leu Leu Leu Gln Glu Lys Cys Pro His Val Thr
    450                 455                 460

Glu His Ile Pro Arg Glu Arg Leu Cys Asp Ala Val Ala Val Leu Leu
465                 470                 475                 480

Asn Met Arg Asn Pro Asp Gly Gly Phe Ala Thr Tyr Glu Thr Lys Arg
                485                 490                 495

Gly Gly His Leu Leu Glu Leu Leu Asn Pro Ser Glu Val Phe Gly Asp
            500                 505                 510

Ile Met Ile Asp Tyr Thr Tyr Val Glu Cys Thr Ser Ala Val Met Gln
        515                 520                 525

Ala Leu Lys Tyr Phe His Lys Arg Phe Pro Glu His Arg Ala Ala Glu
    530                 535                 540

Ile Arg Glu Thr Leu Thr Gln Gly Leu Glu Phe Cys Arg Arg Gln Gln
545                 550                 555                 560

Arg Ala Asp Gly Ser Trp Glu Gly Ser Trp Gly Val Cys Phe Thr Tyr
                565                 570                 575

Gly Thr Trp Phe Gly Leu Glu Ala Phe Ala Cys Met Gly Gln Thr Tyr
            580                 585                 590

Arg Asp Gly Thr Ala Cys Ala Glu Val Ser Arg Ala Cys Asp Phe Leu
        595                 600                 605

Leu Ser Arg Gln Met Ala Asp Gly Gly Trp Gly Glu Asp Phe Glu Ser
    610                 615                 620

Cys Glu Glu Arg Arg Tyr Val Gln Ser Ala Gln Ser Gln Ile His Asn
625                 630                 635                 640

Thr Cys Trp Ala Met Met Gly Leu Met Ala Val Arg His Pro Asp Ile
                645                 650                 655

Glu Ala Gln Glu Arg Gly Val Arg Cys Leu Leu Glu Lys Gln Leu Pro
```

-continued

```
            660                 665                 670

Asn Gly Asp Trp Pro Gln Glu Asn Ile Ala Gly Val Phe Asn Lys Ser
        675                 680                 685

Cys Ala Ile Ser Tyr Thr Ser Tyr Arg Asn Ile Phe Pro Ile Trp Ala
    690                 695                 700

Leu Gly Arg Phe Ser Gln Leu Tyr Pro Glu Arg Ala Leu Ala Gly His
705                 710                 715                 720

Pro


<210> SEQ ID NO 3
<211> LENGTH: 42450
<212> TYPE: DNA
<213> ORGANISM: Human

<400> SEQUENCE: 3

tcatgactgc ccctagaagc ttaactgtgt caattctcag acgtagttta cagctttttc      60

ttttctttca gacattaaaa agagcggatt attttactca taaaaagtcc agtccattaa     120

gatatcaaaa ctcaaactct tatccagttg aaacctcttc cctcacctag ctttgccagg     180

ttcagtgtga gattccatcc aggctgaagc cccttatccc tattcttcat gtttctacat     240

ggaggaactt acctggagaa aaacttccag cctctttctg cttccagaga agtagagtga     300

ctcatttgat tgaatttcag agaacagata gggtggagtg tgctcaggct cctctgggta     360

ctctttctgg ggtctgtggg ttgactggag gggtgtcttc tggtgggcac tcaattgcat     420

agtgcttggt gaggcagttt catggcctag aggctggggg atatgtttgt ctgacttacg     480

ggtgatttag tagcttgccc tcttgcttgc agatttaagc cttgtccttc aagctaggtt     540

tttaatttgt ggcaaagctg atattttgat acccacccat cttattgctg tgtctttttc     600

atccgtttct gaactgggat aggaagaggt gattatcctt gattgtctaa aaccccgcta     660

ttccactgtg gggaaggtgc ctgtgggtat tcttttgtcc actctctctt ccaactttct     720

cctccggctt gctgtggctc accgcccctt cgaagttagg ctgggggtag gaattgagga     780

gtgggtgccg aaatgctcac taggctgggg cagttgtaac tggatgtcag ggcttctgtg     840

ggccaggtga agacatgctg gggtcttctg tgggtccttg acctgactta gggaccactg     900

gctgcagcct ccagacgtca gccatgtttc caacagtcag acgcccccctg ccctgttgcg     960

cccggctgtc ccttccaagt tcggtcactc gctctgcctc catcttcctc ttccctctgc    1020

tgctaaggct tttcaccttt aatttctcct ggggccaccc ccaactccag cgaccccgtg    1080

agcagctgag gctctaccgc gctcggtcct ggccagcgac gcagcccttc cctggcgggg    1140

ctccagggct tctggcccct gtggtccgcc aggtgtgggg gcccacggcc tcaccgcgcc    1200

taccccactc cccccggcga agctacgcgg cgctcagctt cccagggacg ccggcggcgc    1260

cctcggctcc tccgctccgc cccgccctcc ccctggtctc gcactggagc cgacggcccg    1320

cgcccacctc acctcagggc ggcctcccgc ccccaccccc ggccccggcg tccgggcaaa    1380

tcctgcagcg cgagagcaat tccctgccac ccgaccttcg cactcgctgt cgctcgctcg    1440

agcctcgctc cccacgtcct tccttccgac ccgcggctgg accctcctca caaatttctc    1500

agagaggctc acctcaaagc gcggcgcacg aggccgggct cccgggacgc aagcctctag    1560

agggcgcgcg agaggccccg cccccgccct tcggccccac ccaccagccc cgcccccacc    1620

cgcacccacc aggccccgcc cccacctccc cacccaccag ccccgccccc acctccccac    1680

ccaccagccc cgcccctcat gccccgccaa taaggcccca cccgcctccc ccgtcccgtc    1740
```

-continued

```
gccttcaccc accatccccg ctccctcagg ccccgcccca cgccgcatgg ggcaccaagc   1800
gctccaccac tgtggtcgcc tggcacaccc cggggtcacg ctcgcggcgc tctgattggt   1860
tgcgtgggcg tcggcccacc taagcctgag cgcctgccga ggcctgcgcc tgcgtagtgc   1920
gcgcgggagg ggcgggaggg gcgggagggg cgggaggggc ggggctgggc ggcaggtccc   1980
gggtgcggac atctggcagc tggcagtggg cggcgtagag cactgcagca gcaatgacgg   2040
agggcacgtg agtcccctcg ccccgggctc ctgacgaatg cggggtggtc ctaggtgctg   2100
aggagagcgc gactggggca gtgggccggc ggccggcgtt ggggcggggc ctgggtcgct   2160
gatggccggt ggtcctcagg tgtctgcggc gccgaggggg ccccctacaag accgagcccg  2220
ccaccgacct cggccgctgg cgactcaact gcgagagggg ccggcagacg tggacctacc   2280
tgcaggacga gcgcgccggc cgcgagcaga ccggcctgga agcctacgcc ctggggctgg   2340
acaccgtaag ttgcttccgc ggagcgtcag cgagctcggg accctgaggg gtgagccgtg   2400
aggagcacgt tttctctcag aaaggcgggt gggaggaccc ggccagcgac gcccatcccc   2460
aaggcgagcg cccacgggaa ctgcgttcgc gggcccctcc gcttcagccc cttcatctct   2520
aaaccacgca taggagactc ctaatgtttt attttttagc accttatttt gagataattt   2580
ttgacttata ggagagttgc aaagatagtt gtaactttgt ttttattcac aaaaagtgtt   2640
tggatccact gtcttagttg tgtgcattgt aagagatttt ggtcgtcaga gtctgcagtg   2700
taaacagggt ctcctgccga gccccggcca ccgagggaaa ggctgtgccg ccccttgggc   2760
cctctttgag aggcccgagt cccaggccca ggtcggcacc cgtgccccac cctacagtct   2820
gggtgcctgg tttattccag acatcttgga gaagttgtga agaatacatg actggcaaat   2880
aaagcaacga aaatgtgcag ctgttctttt actttgctga ggtgtgatgc tctcatcaaa   2940
gagtttcaga cttttgatgg aaacagctga aacttttaaa gtaatttaca ttcactgttt   3000
tgacttgggc tgtatgtgaa gagggttcct ctggccgggc aacagtcccg tcagctatct   3060
cttttttttt ttttcgatct ctttgcagaa gaattacttt aaggacttgc ccaaagccca   3120
caccgccttt gagggggctc tgaacgggat gacattttac gtggggctgc aggctgagga   3180
tgggcactgg acgggtgatt atggtggccc acttttcctc ctgccaggta ggagtatgct   3240
gccccagcct gatggtatgg ccaccctgga tcacccttgg gatcctggcc cagcctggtc   3300
tagggttttg atgaagcagg tgaaaatcca ggggctcaca agaaaagggc tggcaaactc   3360
tgccctatgt cagagtcgtc ctgctattgg tctaggggat cagctagcct tgccagtgta   3420
gggtgacagg ctctctgata agagaagcaa gtggttctct agggctctgt gttgccttga   3480
gggaggagga aggtgggctt tgaagtctca gtacaggatg ggatggacat tccaggtgga   3540
aggcccagcc tatgccaagg ggctgtaggt gggcagagtg gtgggtgggg agctgatatc   3600
tgctgtgaac ttcctcgggg ctattgcagg agagcttcag gttcaggctg gtgagtagga   3660
ggagcatagc agttggactg cctgggtatt gaactgattt ggctacacaa gactattttg   3720
catcctggga gtgtttctct acagaaatcc tcagccttgt aaaatgggaa attccctcct   3780
atgaatttat gcaataggac ttttttccct agtgacttgt aatcacattg tttcaatgac   3840
gtgaattcct acataaatag gttttgtttc tgtgataact cttactgata catcattttc   3900
ttttactacg ctgactttgt aatagataga aagtccttat atacctttgt tgcctttctt   3960
tttaaaacat ctcttacctg tgtctattca tttactcatc caaattgcct ttatcctgat   4020
tttgtcccag acttgaaatg aagttgcaat aggcttatat gttagtttgg gaagagttgg   4080
cctttaacgt taaaaacagt tccatggtgt ttactgtagg ccaagccctg ctcaaggcct   4140
```

-continued

```
gttcttcttt tagtccttag aataagccta atgagataca ttagaaagct gaggcacatt   4200
tattccaggt aaccagacta gcaggaggag cactgggatc cccatctctg ctttgacttc   4260
tagccctgct gccacctgga ctgtacagca ttgagttttt ctgtcctggg atttgagggc   4320
ctgtccttag gggaagtcaa ggtgctcttc ttcccttggc cccatcaggg cctgtttaga   4380
ctgttctcag ggctcgtggt aaggcaatga catagagttg gtcaggagat gggtcagccc   4440
cactttgcct ctgtagcctg acctgtgaca ggattggaat caggtttggt catgtgcaca   4500
gtgtcaggca tgcagtggtg cttggtcagt ggggattact gtgttgtttg ttcttgctgc   4560
tttggctctg ggcttagctg gctgggaccc ttcctgtggg ctggctgtga gttggagttt   4620
ttttgtattt tttttttttt tttgagacag cgttcgctct tgttccccag gctggagtgc   4680
aatggcacaa ttttggctcg ttgcagcctc tgcctcctgg gtgcaagtga ttctcctgcc   4740
tcagcctcct gtagggtcca gccccacagg gtcggtaggt tttctccct gtgtgcggag    4800
atgagagatt gtagaaataa agacacaaga cagagagatg aaagaaaaga cagctgggcc   4860
ccgggggacc actaccacca agacgtggaa accggtagtg gccctgaatg ccaggctgcg   4920
ctgatattta ttggatacaa gacaaagggg cagggtaagg agtgtgagcc atctccaatg   4980
ataggtaagg tcacatgggt cacgtgtcca ctggacagtg ggcccttccc tgcctggcag   5040
ccgaggcaga gagtgggaga gagagagaga gagacagctt atgccattat ttctgcatat   5100
cagagacttt tagtactttc actaattttg ctactgttat ctaaaaggca gagccaggtg   5160
tacagggtgg aacatgaaag tggactagga gcgtgaccac tgaagcacag catcacaggg   5220
agatggttag gcctccggat aactgcgggt gggcctgact gatgtcaggc cgtcccacaa   5280
gaggtggagg agtagagtct tctctaaact cccccgggga aagggagatt ccctttcccg   5340
gtatgctaag tagcgggtgt ttttccttga cactgacgct accgctagac cacggttggg   5400
tccgcttggc aacgggcctc ttcccagatg ctggcgttac cgctagacca aggagccctc   5460
tagtggcctt gtccgggctt aacagaaggc tctcactctt gtcttctggt cacttctcac   5520
tatgtctctt cagctcctat ctctgtatgg cctggttttt cctaggttat gattgtagag   5580
cgaggattat tataatattg gaataaagag taattgctac aaactaatga ttaatgatat   5640
tcatatataa tcatatgtat gatctagatc tagtataact cttgttgttt tatatatttt   5700
attatactgg aacagctcgt gccctcggtc tcttgccttg gcaccaaggt ggcttgccac   5760
ccacagcctc tcgagtagct gggattacag ccatgtgcca ccatgcctgg ctaatttttg   5820
tatttttggt agagacaggt tttcaccttg ttggtcaggc tggtctcgaa ctcctgacct   5880
cgtgatcccc caccccccac ccccagcctc ccaaagtgct gggattacag gcgtgagcca   5940
ctgcacctgg ctgagttgga gcttttcttc cctctttttg gactttggaa aatgctcttg   6000
gtccatgatg ctatgtagac agctcccgtt gactgtggcc tgtgcggcat tgggcagcac   6060
tctggtgaac actgaatcgg gtctgacctc ctagccccac catttactgg ctgagcctca   6120
gtttccttgc ctgtaaaatc aggaagatgc tggctctgct cctctctgca catttccccg   6180
tcctaacaac attataactg ttaggaaaga gacgggcttg ttttgggatg gctcatttta   6240
tgtgaccctg tgcgctgtct ctgagtccat ctgcccttct tccagggtgt agggaccagc   6300
cccacagggt cggtgggtct ctccctgtgt gcggcgatga gagagtgtag aaataaagac   6360
acaagacaaa gagataaaag acagctgggc ccgggggacc actgccacca atgcatggag   6420
accagtagtg gccccgaatg tctggctgtg ctgttattta ttggatacaa agcaaaaggg   6480
```

-continued

```
gcagggtaaa gagtgtgagt catctccagt gataggtaag gtcacatggg tcacgtgtcc   6540
actgggacag gggggccttc cctgcctggc agccgaggca gagagaggag acacagagaa   6600
agaaaactta tgccattatt tctgcatatc agagactttt agtactttca ctaattgact   6660
actgctatct agaaggcaga gccaggtgta caggatggaa catgaaggcg gactaggagc   6720
gtgaccactg aagcacagca tcacagggag acaggcctcc ggataactgc gggcaggtct   6780
gactaatgtg aggccctcca caagaggtgg aggagcagag tcttctctaa attcccccgg   6840
ggaaagggag cctccctttc ccggtctgct aagtagcggg tgttgttcct tgacactttt   6900
cgctaccgct agaccaccgt ccgctcggca acgggcgtct tcccagacgc tggcgttacc   6960
actagaccaa ggagcccttt tgctggcccc gtccgggcat aacagaaggc tcgcactcct   7020
gtcttctggt cacacctcac tatgtcccct cagctcctat ctctgtatgg cctggttttt   7080
cctaggttat gattgtagag cgaggattat tataatattg ggataaagag taattactac   7140
aaactaatga ttaatgatat tcatatatct ctaagatcta tatctggtat aactattctt   7200
gttttatatt ttattatact ggaacagctc gtgtcctcgg tctcttgcct tggcgcctgg   7260
gtggcttgcc gcccacacag ggcatgtctg gatggtttga acactagggc ttctgatgct   7320
ctaagccaga gtcaggtatt cattccatgg cacatgtggc tggggtctgc cctgagacct   7380
gtcccgtgcc aggctctggg ggcacatggc tgatggaacc aagcatgggg agtgaaggtg   7440
gagggtggcc tgtgagcacc atgcctgaga ggaccaggct ggggacggaa ggttcttagt   7500
ggataatatt tattgtctct gcctcccccc tgacatttgc aaagcggcat atgcttgtaa   7560
aaaaattttg aaacagaaaa atataaataa ataagtaggt attaccacat gcaagggtga   7620
ccaattttgt atttttcttc ccagcagatg ttaaagcaag accaacagtc tcccctcatg   7680
gaaggcccac tgatctaaaa tgctggttcc ttttggacct tcagggcact tgggggagac   7740
cttcctgagg tgctgtgcag tgtctggtgt ttctcagacc caggtggtca tgggagccag   7800
gcgtggctga gtgggctcta caggccctag gcagggagca tcgcctgtgc tgtggctgac   7860
gttccttctg gccctgttcc caaagttccc catgggggcc tgggaggaat ggcctttcca   7920
gggggtgttt ttatgagaag gaggtagctc cctgttggag tgaggtgctc aggaggaaag   7980
gggcctggtc ttagcagtca tgaccacctg tccccagtga ggaacatctc tcctgccaca   8040
caggcctcct gatcacttgc cacgtggcac gcatccctct gccagccgga tacagagaag   8100
agattgtgcg gtacctgcgg tcagtgcagc tccctgacgg tggctggggc ctgtgagtgt   8160
gcctgcccct gtgtcactgc acatgtgcat gtgtgtgttc tcatgatgta ggagatgctt   8220
gggtttccag gcagctgcca ggggttagga gtgattgcag ctgtgggtgt ggggtgggtg   8280
agggagagac tagcaggcgg ggagtgggct gaaggccatg caggtggggc ctcggcttca   8340
catcttttgt taaatggatt ttgtggctgt tacgacactc ttgagaccca catgtgaaaa   8400
ctgtcagtct gttatcactt aagacagaag aaaattgccc ttgactctgg gctggcagca   8460
ggtggagaca aggcctgaca gctttcctgc catgtggcac acactttggg agcagagcca   8520
tagcccaaag tggaccgccc ttgagctaga agtgttgact caggcgtggg aaggtgtaga   8580
gcaggcgggt cacggtgagg aaggagtggg gggctcagtt gtcatgggag gtgcatgaat   8640
tcgtactgca gagtggctgc tcaggggtct cctgtgttga catgttatgt caggttaagc   8700
cattttagca ttcttagttt tctgaggaaa ctccacagaa agttttgctt tatttcttag   8760
aagtaaggac agataccggt ttctcacctg tcctctgctc ctgtaggcac attgaggata   8820
agtccaccgt gtttgggact gcgctcaact atgtgtctct cagaattctg ggtgttgggc   8880
```

-continued

```
ctgacgatcc tgacctggta cgagcccgga acattcttca caagaaaggt acggcatgtg   8940
cagcatgtgc tgggccaggg gttcgtgtca actcgataat gagctctcac aaacgagata   9000
cagaaagatg cacttgcagc tgaaacagtg ggcaaaagca catgagcagg gaatttgtca   9060
aagcagaagt aggcagacac tgtttaacct aggcatcatt ttttaaaaaa gcaaattaag   9120
agccaggcac agtgagtggc tcacgcctgc aattccagca ctttgggaga ctgaggtaga   9180
aggaccactt caacctaaga gttcgaggcc agcctgggca acatagtgag acctggtctc   9240
tacaaaaaca ataaaatatt agccaggtgt gatgatatgc acctgtagtc tcagctactt   9300
ggaggctagt aaggcaggag gatcacttga gcccaggagt tctgggttgc aatgagctgg   9360
ttgtactact gcactctagc ctgggtgaca gagtgcgacc ctgtctctaa taaaataaaa   9420
aagccaagca aactaagaca accaggtaat tctgtttgtt tcctgaattg gcaaaaactt   9480
aaacgaaccg tgttaatatg tccaccttct ggggggcagc ctggctgcag gcaagagcag   9540
ccctggagct tgcaccttcc aagctgatcg tctacctctc caagcccggg gctgtccacc   9600
tctccaagcc cggggctgtc cacctctcca agcccggggc tgtccacctc tccaagcccc   9660
gggctgtcca cctctccaag ccccgggttg tcttacctct ccaagcccca actgtctact   9720
tctccaagcc ctggtctggc tacctctcca agccctgggc tgtccacctc tccaagcgcc   9780
aactatcttt ctctccaagc cctggcctgg ctacctctcc aagccccagg ctgtccacct   9840
ctccaagccc caactgtcta cctctccaag ccccggcctg gctacctctc caagcccctg   9900
gctacctctc catgcccggc ctggctacct ctcctcttgc ctataggccc tgaggggcaa   9960
ttccagccca agggaatcca tggctcctgc tgctccaaga aaacctagtt tatgttgtgg  10020
ctctgcagag cctggcctgg tcttgtcctc tgtgtttcac agaccttccg tagccagtcc  10080
cacctgccct gctctctgct gcatgcgcag gggcctcctg tcagctcctc agagaccctt  10140
attatcccag ggctcgccat gcactgcctc cttcgcctgg agcctcttac cttccactcc  10200
tgccccgctg gctcacactt tacgtgttcc ttctttgagg acctcttcct gacctaccgt  10260
gccaggtgga gtgtcctgtt acgcattctc atgagatcct gccttctttc ttggtgagct  10320
tgtcactatt gtcctcagtt cactgtcagc ctttggtgtc gttgatgctg cgtccccaag  10380
gctgctgtcc ggttcccacc acactcctgg cgcctgcctg gtgaaggaac gtgtttaggc  10440
tgcactttgc ctagtagctt tgtgggtctt tattgacttt tgcatacctt ttggggtttg  10500
gagcagggac tcctcagaag catgtttaga tggtgtggct gtgccaggac tgctgctgct  10560
gaagtggctc tggcatgggg ccagcgtgct ggagctactc tggagtctag ggtcgtcttt  10620
gttcccatac aggaccagtc tgccaagtgg agatgacaca gactggggca gctcaggctt  10680
ggctcagagg gcgaggctga gtgtgcgctg tcacttcccc accttgcctt ctccaggcgc  10740
atgtgcacct gggcccctcg ctcacctgag cactgaggtg tccctggacc ttcccaggta  10800
gctgtcttca tgtgctcctt cctggggcca ggggttgcaa acacctctcc tggggctgga  10860
cacacacact cccaggaaag ccactggttc cacctagggg gccgtgtatc caggcaagtt  10920
ctcagcactc tggaacctgc ttcgcacatg gggtcgcaa gatccacatg aggctgccct   10980
tgcctcatgg agaggggcac acgtgactcc cagagggtga agcttcccag ctagaggcag  11040
tgcagacttt gctgacagga agcagatgac gtgggcctat tctctccccg ctcaggtggt  11100
gctgtggcca tcccctcctg gggaagttc tggctggctg tcctgaatgt ttacagctgg   11160
gaaggcctca ataccctgtt cccagagatg tggtatgtct gctgttgatt gggttgttgg  11220
```

-continued

```
gtcgctgctg ctgtcccggg gagtagagtg acagggaccg tgggtcaggt gcaggctgtg  11280
acagcagaga ggggtgggca ttctgtgggt gggtggagtt aggctcctgg cagaggccct  11340
gatcaagctt gagtcctgta ggggtacaga aaggggggagg ttcccaattg agcaggaaga  11400
aggctgtgcc atggatggag gtaccccgag tcaggctgca ggcagggctg ggtggcttcc  11460
ctcttgctgt ggaagactca gcatctgtag aagtgggggg gtgcccctcc cccagcctgc  11520
acaggggcgt cctgtgttgc tgctgctgcg tttgtctcct ttgctggtga atgtgaagtg  11580
tgtcccgacg tgacacctca cctgtggact cagcgtgtgt gcctttaaaa gatcagtgtc  11640
tgtggccagg tggggtggct catgcctgta atcccagcac ttcgggaggc cgaggcgggc  11700
agatcacgag gtcaagggat cgagaccatc ctggccaaca tagtgaaatc ccgtctctac  11760
taaaaataca aaaattagct gggcgtggcg gcgcgtgcct ctagtttcca gctactcggg  11820
aggctgaggc aggagaatca cttgaccctg ggaggcagag gttaccgtga gccgagatcg  11880
tgccaccata ttccagcctg gcgacggagt gagactctgt ctcaaaaaaa aaaaaaaaaa  11940
gatcagtgtt tgttttttta aacagaacca catactgttt aaatacccag caaaatcaac  12000
attaatttct tattatctgg tgtgtgtttt ttttgttttg ttttgagacg gagtctagct  12060
ttgtcactca ggctggagtg cagtggcgtg atttggggtc actgcaacct ccgcctcccg  12120
gattcaagca attctcctgc ctctgcctcc cgagtagctg ggattacagt ctcaggccat  12180
cacgcccagc taattgttgt atttttagta gagacagggt ttcactatgt tggccaggat  12240
ggtctcaaac tcctgacctc aggtgatccg cctgccttgg cctcccaaaa gtgctgggag  12300
ccatgagcca ctgctcccgg ccttatgtgg tgtctttaac cagtgtcttg taacatttta  12360
tggctatcta ttgaaagcag tggacatctc cccagaaaac actcgtgcat atgagtttac  12420
cccgttatgc attttgggaa gtgagaccct ggaaccacac agagcccctg ctggcttcct  12480
tgagtgttgt gggaaccctg gtgggggtgt cccctacaga gctatcatca gggctggggg  12540
ggtcccttgt gttagatgac tttggtgcgg gggtgggggg tggggggtca agttagggga  12600
ggcaggaagt gaaggggccg ctcaagaaag gacagcagca gtgtcctgat gcaaaggccg  12660
ggggcttaac cccggaagcc agtttgggtg gtgacgggga ggcacaggga tggtgagatc  12720
accccgggag ggtagacaga gataccagag tagggggcag ggttagggtg ccgctacctg  12780
aggcgggccg tagagcacat aggttgggag gtgtcctggg gccattcaaa tgcccgctgg  12840
actctgcgcc tcgcccgtgt gtaatgagcg gcagaggaag gactgagacg gcagtcagca  12900
cagctgccag ggcaggaggg gtgtgggttc cacacgctgg tgctggtgag ggcgtctcat  12960
ctgccccact tggggggggcc gtcggtcagt gctgccgcat gggcacgcca gggtgctgct  13020
tgtctttgct ggagttgctt ggagggtggg ttgggaggtg aaaggaggac cacagacctg  13080
aaccactcca gctgcgaaat gctggaagtg taacccaaaa tgtgagaaaa aaaaacaccc  13140
ttttaagtaa gtgggtgtga aagtgggcca aggcctgatg ccacagtcag ggagcaggga  13200
aggctcagca ttgctcaccc tcacttaagg atggggctag catcacataa ggcatcacat  13260
aaggatgggg gctagcaggg aaagggagag aaaacacatg aggcacacac agaccctggg  13320
aagctggtgg agctgtgcta acgtcagcag accagtgatc aaagacccag gccttgggga  13380
gattccacag acctacagac ctacagtttc ttttttcttt ctttttcttt tttttttttt  13440
ttttgagaca gagtctctcg ctctgtcacc aggctgtgtg cagtggcaca atctcggctc  13500
actgcaacct cctcccaggt tcaagcgatt ctcctgcctc agcctcccga gtagctggga  13560
ctagaggcac acaccaccat gcctggctta tttttgtatt tttagtagag atggggtttc  13620
```

gccatgttgg tcaggctggt ctcaaactcc tgacctcaag tgatccacca gcctcggcct 13680
cccaaagtgc tagggttaca ggcgtgagcc accgtgcccc tcctaaagtt tcttaaatac 13740
acttttaaaa gtaaacttta aattttggag tagtttccaa tttctggaaa agttgcaaag 13800
atagccaaga gtgttccctg ggccctcac accatatccc cattgttgat gttttatgtt 13860
accaaggtac gtttgttgta gctaagaaac ccacggacaa tcctaagcat ttaggagctc 13920
catcacctgg ttttaggatg caaaatgctg accgaactag gaggtgcagc tcctcagagg 13980
gtgcacctat ggttcaactg tgcccctcag gagcacggtt gggaaatgcc cgcagatgca 14040
ctgacgtggt ggggaatagc catccaccag tgttcgtgct tgaaagggcc caaggtatgg 14100
atgctggcgg agggggcagg cttgagtctt ggggtctccc actgactcct gctgttgccc 14160
caggctgttt cctgactggg caccggcaca cccctccaca ctctggtgcc actgccggca 14220
ggtgtacctg cccatgagct actgctacgc cgttcggctg agtgccgcgg aagacccgct 14280
ggtccagagc ctccgccagg taggacctca tcagggaaca aagtgaaggc ctctggggct 14340
gggacccaca gggcctgggg cttctggaat ctaaccacac ctgtccactc acctggtggc 14400
cctgtggagc ggagagccct gtggagcaga gcctccacct tcctccatcc tataataaac 14460
agtgagcaag ctctgcccag aggggacttg tgctatggga cagtcagtag ctgtagccca 14520
gggttcctgg gggggacttc caggactcaa gggatgcagg aggcagatgt gcactgtgtc 14580
ctctggaagc aggcctgagg cgaggtttga ggtgcaggat gtttatcagg cctgccatgg 14640
ggaagaagga ggggcagagg gaggaaatga gcttctgggc agacctggga ctcatggagc 14700
tggggagctc ctcagagcgg tcctcccata gggggccttc atgtgccctc ggggtcagtt 14760
gctggaggga cccccaccca ggaagggact ggcccagggc cctgagggcg gatggtggga 14820
ggccacccct cctggtttga gccaggccta ccaggtgctc ccaggcccca aggctcagac 14880
actgccccta ccaggagctc tatgtggagg acttcgccag cattgactgg ctggcgcaga 14940
ggaacaacgt ggcccccgac gagctgtaca cgccgcacag ctggctgctc cgcgtggtat 15000
atggtgagcg cctcctgagg ggccggcagg gcagcccagg gtcagggtca gggtgtcgcc 15060
cactcattca cgcactcatc ccctgccagc ggcactgggc cacctcctct gtgccaggcc 15120
ccagggggcg ggatctcatc gccctgcccc tccaccctga gaaccagctg gtcttctact 15180
ctcaggagtc caccctgtgc aagggtgtgt ggtaggaggt gtggggcagc ccctcctggg 15240
cagggaagga ggagctcaga gaccaggcct gggggtgggt gggaggggga aaccctgggg 15300
aagggcaagt ccaggcgttg cagtgcatgg agctccaggc tgaggccagt gtcatggtgt 15360
ctggcatcca ctgaccoctg tcccctgtag cgctcctcaa cctgtatgag caccaccaca 15420
gtgcccacct gcggcagcgg gccgtgcaga agctgtatga acacattgtg gccgacgacc 15480
gattcaccaa gagcatcagc atcggcccgg tcagtgcccc tgcccggcct ctgactgcag 15540
cccctggggg ttgaggtccg aaagtgaagt cctagaggcc gggctgtgag ctgggagtgg 15600
ggtttcctgg agcctggtgt acctccattt gggaggtggc cctctgatcg cacaagtgtc 15660
tgagggcttc tgtcctggac ccctgcacgc ccagctcagt gaagttgccc caccacactc 15720
gaccccccgc ttccgtcccc caccggctct tgtcctcagt gtgcctggac actctcctag 15780
aggcccctcc ctgagatctt gctggctagc tggctagctg ggaggggtgc tttttcctca 15840
cttggttccc tctccccaaa cagttcatca ttcgccattc tcccgtgggg tttagacatg 15900
cccagggtgg gtgggagtag caggtgccac tcctgattcc tcctgcctag ctaggactt 15960

-continued

```
ggagctctca cctctgtggg gcctgcaggg gtccaggtgt ggccagttca gtgaccttag  16020
agggtgcaat ccccgggctg tgctggtgcg tggccgcctc ctgacagagt cagcaggccc  16080
tgggctgtgc tgcagctgct gccgtagctg tgcgcgtagc tgctgcggtg tagtgggttg  16140
gcttaggcat tctctggaca tacccaggtg gcactgggcc actgagtccc accctgacac  16200
tgcatctcgg attttctggg cctcatgcca cctcagtgga tcacaaatcc tgactgaccc  16260
tgcagcgggt cccttgtttt ttgctcagca gtgatgtggt tctttgtggg ttttggttta  16320
atcccatata gagcacatct gtactaaacg cattagaaac atgcttgcaa ttggatcttg  16380
acttgtgaga tgcataagta aaaagttggg ggcctctgga acattctgtt ctgaggaaga  16440
aggggggcaa gtggtcccta ctgctacagt cctgtcttcg catctcttcc tgggcccctc  16500
aggccctgtc ctctgtcccc tgtgttgtct ctaaggcacc tggtagccca tgcccctctg  16560
gtttctcctg gaacccctcg cttctccctg gtggagtgct gctccttctc acagcctaag  16620
gcaggctgtg gccttggccg acactgcctc tgtctgagtt gggtcctggg gacacagttg  16680
ttgcccatcc tcgctcagga aatgcctgtt agagcagaag gcccctgtcc tggccctgag  16740
tgatctgcac ggcactttat gcctggggc  tgctgtggat ctggacgaga ccttgtccct  16800
ggaggctgct gtgggtctgg agcggagcct tgacagggct gtctctcctg cagatctcga  16860
aaaccatcaa catgcttgtg cgctggtatg tggacgggcc cgcctccact gccttccagg  16920
agcatgtctc cagaatcccg gactatctct ggtgagtgtg gctgggatat gctggcgggg  16980
cctctcacga agactggatc tgagccccag ctgcatccca gtgagggggc ccccacggtg  17040
ccatctggga atactgccag ggaatacctc caggaaccag cagtgtcagg gcttgtggaa  17100
gccactgagg gttgtctttg aattggaaga tttgccaccc agtggaagtg tggggtgttc  17160
ccagaaggta gagtgaggaa gggggtggta ggtagcaggg caggttcagg ttggcatcag  17220
gaggcctgtg gacaagggga gcttgtcagc catggactgt gccctggagg tggggcccct  17280
gtcatggagg gcagagagcc gtcccatggt gggaagcttc cgctgtacag gcctcttcct  17340
ctggtgcctc agcactgcac gagggcggca gggctggcac agcctggggt cggggagcct  17400
cccgctgccc cttgccttgg gtgtggccct tctgggtgag tgtgtcctgt tttccataga  17460
gtgtggccct cacccccagg agcccagcag cccagctggg gtggcatcca ggccagtgcc  17520
aggcctcggg aggggacaga cggcctctct gggaccctcc tgagtgcagg gtctgggtag  17580
cagctgggct tccagctttc tccttgcacc tgacttgggc ttttttctcc tcacaggatg  17640
ggccttgacg gcatgaaaat gcaggtaagg gctgcgggac tgcggctgca tgcttccttt  17700
gcaatcatgt ctcccctttta ttatttttcc tttggggttc agaaataact cctcctggac  17760
caggtcccgg cagcgtgcga ctagaggctg agtcagttga ggcctctggc cgtgtccctg  17820
tgggtgctgt tggtctctgt gtgggtgccc accgttctcg atgtctgtct gcagctgtcc  17880
tgtttgcttt ttgccctgat gatctgagtg ggctcagctg tgtaacgaca gacccagagc  17940
tgcagaagct ctcatcttgt tactgtggca ggaggtggct ctggttagtg ggggcttctc  18000
ctccatgcac tcttaattta aggggcttct tcttaaaggt cctgggtgga caggacagga  18060
gcctggagga ccgtggtggc gtgtggccgg gcctgggagc tccccgtgga cttggcctga  18120
gtgggctgga acccagtcat gaggggcacc aagcacaagg agaggggagg ccgggtggat  18180
cctggctgac cctggtcctg tcctggctct gggggccctg tagaccgcag tcctgtccga  18240
ctgggctgag cctgcgcccc tctgtgcgtg tcagaagccc agacagtgtt gccctgtgtc  18300
ttgtggtcta aggagggtta cgccctgcgg tgcctgtctt ctgtcccccca cctgattcag  18360
```

-continued

```
tgtggaaatg tggagtctcc agaggtgtcc tgggtgtcac atttgggatg gatacacgtg  18420
ggcccagcac tgcccgcccc agggctaccc ttggtgccag gtgcccccag ccacgagctt  18480
ttacccagct ggccttgagc tccccagagg ctccccggac actgtccgtg ttttgtgaaa  18540
aggttttcaa aacacatgta aagtggaggt gagtagcaag ccctagagca ggccctggcc  18600
tccctgcccc tccctgtccc ctccctgccc ctccctgccc agcgctccct cagcaccgac  18660
tcatcagtgc acctcaagct gatgagggcg tctgtgtttt gacaaaattg ctctgaggtt  18720
gtcacaccca acaaacttat gacggttcct gagtgtagtc ctcacgttgt ggctggtgtt  18780
tgtgaatcag gattcaggcc aggcctgcac aggccttcag ttgttggtct ttgagctcct  18840
gttagtccag ccgtctctcg tggtctcttt tctcctcctg gaaggtttgt tcctgaaggg  18900
cttcacattg cagatctgac tggttgcttc ttatgttccc tgagtttttg taaactggcc  18960
aggccctgag gctcgatccc attgtgtttc tttggcgaga atgcttttct ggtggtccct  19020
gccttgtccc tccagtgcac gatgtctgga tgcctctgcc acacaccacc ccctgcccag  19080
tccccatgtc tgtctggtca gtgcccagct ctgtctcact agggtttggt caccggccct  19140
ttgaactgag accaggctgt gtacctgtga gcccagctcg gggtgagatt tgaggtggag  19200
ccttcccagc cctgtgcaga attcccatca cctccaggtg tactcagaaa tggggatcat  19260
tggccaggtg cggtggctca cgcctgtaat ccctacactt tgggaggcca aggtgggcgg  19320
atcacaaggt caggagatag agaccatcct ggctaacacg gtgaaacccc gatgctacta  19380
aaaaatacaa aaaaaattag ctggatgtgc tggcaggagc ctgtaatccc agctactccg  19440
gaggctgagg caggagaatg gcgtgaaccc aggaggcgga gcttgcagcg agctgagatc  19500
acgccactgc actccagcct gggcaacaga gcgagacttc atctcaaaaa aaaaagaaat  19560
ggggtcattt ccaggcatca ccatgactga ggtgcgccac tgtcattggg tgagagcagc  19620
tggatgctct atgtgtaggt gctggagcct ctgagggatc gtccagtcct agaagtgtcc  19680
tcagagggac actgtcctgc ctggtggccc atgaagaaag ggagggctcc ctgagtctcc  19740
ctgacgtgtg tctgcctgca gggctcagcc ttctctgagg cccttgtcag ccatgagggg  19800
tgcccagggc tcagagcctg aggctgagcg ttggctgggt gggagccccc acacctggcc  19860
ctcaggcgcc cattggatcc tggaggcagt ggctgggagt gggaggggct gcatctgctg  19920
ctgtaacacc atcctttgtg tgtagggcac caacggctca cagatctggg acaccgcatt  19980
cgccatccag gctctgcttg aggttcgtgg ctccttctct tttctcagcc tcagctgacc  20040
ttcctgtgca cgtaagccca cgcatccacc tgagggcagc actgctggcc acacacttgc  20100
cactcctcga tacttccagt gacctgggct ctggcctctg gcttcagagg gtcgtgctgt  20160
ggagggggcg gccttggcca gcagccttgg gtgttgggct gggtcggggg ccttgggagg  20220
gcaggggctg gaggctgtgt gagaagggga gtctggtgaa ggctgtttct gagagtgcag  20280
gcaggagtgg gactccaggc tcttcttaga actggaactg cttgggccag gcacggtggc  20340
tcacacctgt aatcccagca ctttgggagg ccgaggaggg tggatcacga ggtcaggagt  20400
tcaagaccag cctggccaag atggtgaaac cccgtctcta ctaaaagtac acaaaaatta  20460
gccaagcgtg gtggcgggca cctgtaatcc cagctacttg ggaggctgag gcagagaatt  20520
gcttgaaccc gggaagtgga gggtgcagcg agccgagatt gtgccactgc actccagcct  20580
gggtgacaga gagaggctcc gtctcaaaaa aaaaaaaaaa aaaaaagaac tggaactgtt  20640
tgttatgggc attctcgagc cagtactgga gaaaaacgag agtggatttt tatgccggtg  20700
```

-continued

```
ggaatgaggt aggtgggatt ctgaaggtgt ttctggagag ccctgagggc tgggccacgc  20760
aaagggcctg cctacacagg gtgctggaga ccctctgggc atggatgctg gccaggcagg  20820
ggggtgctgg catccataaa tggtctcctg cgcccttcca tcttcagtca tatctcatgg  20880
acttttgctg ttttgtcttt aaaggtaagt gcagcaggag accctggcac tctctggaga  20940
tgtctgctgg tttgattctg gtccccggtt ggggcaggat gtggccagga ccatcgggaa  21000
accagcgcag ccatgctggc cgtgcaaggg cagctgagcc tctctgtcct gctgtctctt  21060
ccaggcgggc gggcaccaca ggcccgagtt ttcgtcctgc ctgcagaagg ctcatgagtt  21120
cctgaggctc tcacaggtga ggccggtgcc tggggctctg agggggctga agagggggat  21180
cagggctggg agctcctgca ggcagaagtg cccacctcac ctccaccctg ccctatttcc  21240
tgcactggtg tttcagggtc acccccaccc tcccatcccc tccctagccc ctgctccatc  21300
caccggtcct cctcgggctg gcctcacctg gggcagttct ctgaggcctg cagggtgctg  21360
ggggtgctgg cagtttctgc gtcctgctca tgttggagcc actgtgtgca agggccaggc  21420
acgggcaggg gctgtgtacc ctgagctgca cagcctacac ggcacctcca tgtctctgaa  21480
gcaccttctg cccatggagg tgacgccagc ctgtggactt gccctcctga gactgtttgc  21540
agcaaaagcc ccggtccctc ctgccagatc agctgcccac agaccctgcc cgagcccata  21600
gtttgacctc agtgtctctc acacgtgcct gcaccccagt ctgcagccac agtcatccca  21660
tacatgcgcc ccaacctccc gtgtctccca caccctgtcc cggccacggc ctcagccagt  21720
gtccctctgc ctggaaccgc tgccccccag ccccgtctcc ctcccttcag ctctcactag  21780
gacattgttc tgcagggctt ctgggtcttc ctggcctctg tgtggccaag gctggcaccc  21840
atcttgggct caagcagagg aggggcattg tcctgctgtg cctggcccaa tggcggcctg  21900
ctcctgctcc tgcctcctgc ccaggacttg ctctgggtga tggggacttg gggaggctga  21960
ctgaacccta cggcactcca ggcctcttcc cttctcactg aggtgagaga ggcagccaga  22020
agctgaggtt gttcaggagg cattgggggc gcctggcaca gagcacaccc gcagagacct  22080
gggcccccctc cctgccttct ggccggtggg gagatcacag gggagtcagg tgctgactcc  22140
cagtcccgtc tgggctggtt tgagccctcg ctggccagtc acgtttccca gcagctgtgg  22200
gtggtgagct aaacaggtgc aggccctcgc gcgcctcgca gcaccagtgg tggctgtggc  22260
cggcagagta agctcccagg cacgttctgc ctctccagtc ctgcccagtc tgtctcagcg  22320
atgtcccaga tggggacgtc ccgtggtgac gtgttctctg cttccacatt tgccctcgat  22380
gctgcccagg tcccagataa ccctcccgac taccagaagt actaccgcca gatgcgcaag  22440
gtatgcggga gccagcccca tccctgtccc gtcccccagg ggaggccgcc ctcagcaggg  22500
tgggtccttc cctctgaagg gggggctcct ccctgggggga ctcctccctt ggcgtttttg  22560
ggtgtcctgc tgtggtggat gcctggccta ggggctcatg cttcatgttg ctgagctgcc  22620
tggcacatgg aggcacagtt ggcttgcaca cacagccgtg cctcagagca gttccagtgg  22680
tcacggcaca cacaggcttc agaaggacag ccgaagtgta gccagtgtgt ccggggaagg  22740
cagaggaaag aagtagacct cagagccggt gtgggctgtg accacaggtg cagactgtga  22800
aattaggcat ggacccagct gctgctgcct gtttacaatg ggggtggggg gcacctgggc  22860
cccatcctgt ccgtcgtgag atctgcaggt gttgagggtg tgagctgcac ccctgagggt  22920
ccctgtgctg gaagctggag gtctgtctgg atgtacccag cttggggccc tggctgcacc  22980
cacacctttg gtggctgggc ccctgccctg accgggtgct ctgtggtggg gagggatgcg  23040
tgcggctgtg gggaggttct gagaactggg gtgtggacac ccccagcctg gagtcatggc  23100
```

-continued

```
ttgtgctctg cagggtggct tctccttcag tacgctggac tgcggctgga tcgtttctga  23160
ctgcacggct gaggccttga aggctgtgct gctcctgcag gagaagtgtc cccatgtcac  23220
cgagcacatc cccagagaac ggctctgcga tgctgtggct gtggtaaggc tgtggtccca  23280
gcagccccgt ccatacctcg tgtcctgcag atgagctgcg tgctcacttc cactcctgtg  23340
ggctccagcc cagcacacag tccggccagg ccgtaggagc ttgtccttgg atggtgtcta  23400
tatgtggaga actgtgagct ctggctggac ccctaggggc cttgctgggc tgtgtgcaca  23460
gggccctgca ctgcggagct ggtgtccagc ccagccaccg atacttgggg gagccggcgt  23520
ggcccccaag gtttctctct ggtggtttcc actgggtgtc tgaagaggga atttgttggt  23580
gttggttttg gtgccacatc ctttcagcac atctggcttt tgtgtgtgtt tcccagtgga  23640
gaccctgccc ttttctggca gcacagactt ggtttctaag tcatgggcac gtgtgggggc  23700
atgttccctg gtggctgtgc atggaggccc tgacagatga ggttgcagct gctgcttggg  23760
gcacccgagg gcttggttaa cgtggaaatc agctctccgc cccctgttcc tgccccatcg  23820
gttgtcagcc ctagtgttgc ctctagagag ttccgctgtg ccctgggcgc ctgtgtgtgc  23880
tcagcacatg ggcgagttct agggtgctct ctgtgatttc agctgctgaa catgagaaat  23940
ccagatggag ggttcgccac ctatgagacc aagcgtgggg ggcacttgct ggagctgctg  24000
aacccctcgg aggtcttcgg tgagtggtcg gccagcactg cggcgcgcaa acccggggct  24060
ggctagcact gtggtacaca aacctggggg ccagcttttc cccttgccc gaggctgcaa  24120
gggcccaggt tcaccggcag atctgtctgg agccctccct cagcccaggc tgttctgcgc  24180
tcctccatcc cccggggtgg caggatcctt gtgttgtgga taggagggca tcaggtcaga  24240
cctaggggac agtggagggt tccagtgaga tccacagcct gggctggttc ctgctcagtc  24300
cacagggctt gtgttctgtg gaggctgctg tgtatccaga gcgcctgcag ggaggtgtct  24360
ttggggactg tggggactgt ggggacccat gccatgggca gtaggctgct gtgtgtgcat  24420
ggttgccacc gtactggtct tgggggagga tctcagccct ggtccacctc tgggcacctc  24480
acatacccgc cttcctggtc ccctccacat cacacatggc tttttggggt ggggtcgcag  24540
ctttctgctg tgttcccctc atcttcgctc tcaggtagca caggtgtgtg tcctggacca  24600
gccggcgttt gctctggagg ttggtcaggg aggcagcgtc cgggcccggg ctcactgcaa  24660
cactcttgct tgttgtggct ttgcctgagc tgcagagcct gggcagccag ggtgaaaccc  24720
aacacttggt tcttccctcc ctttcccagg ggacatcatg attgactaca cctatgtgga  24780
gtgcacctca gccgtgatgc aggcgcttaa gtatttccac aagcgtttcc cggagcacag  24840
ggcagcggag atccggtaag gagggtctca gccattcagt gtgggcgctg ccaagtcggg  24900
ggccaagacc cagacgcatc attctgtgac acggccctgg tggcccatct cagaagcgaa  24960
actcatggaa acatgcaaga ggcttcggat gttgtggaat ccagtcatat gccctaaagc  25020
atacaaaata tctgttaggg gctcagaata gcacagttat gatacaaaaa tggattttct  25080
ctctctttta ataatgttaa gaagacatca catacctgac tccaccggtg tcccagaaac  25140
ggtttttaag taacctttcc tgttgaaggg tagcaagtat tcagaaaagt gtacaggttg  25200
gtcttcttga agcaaacagg aagcgaacag tgccagcatt agacatggtg acaccaccag  25260
agccctcggc ccgccccatg acggggccgc ccacatgcct gccaggtcgt gggtgtctgt  25320
tgctcgcttt ggatcttgtc taggtggact cctgaggtgt ggaattcgtg ttgccttctc  25380
ctgctctcct gctctcctgc tcgcggttag tcaggtggct cgggtaacag cagcgttctc  25440
```

-continued

```
tccctcgggc cttcggttga acacagaatg ccgcgctatc cagctgcctg ttctcagcac  25500
ctgggaggat ttcagtctgg gttattatga agcatctact gtgaacactc ttgtacttat  25560
cttttggggg cacctgggta cccatttctc atggtcacgt acctaggagt ggcattgctg  25620
tgttagaggg tacgttatag ggtatgtgat ttttgtaggt tcttctttat cctatcacga  25680
ttacattttt ttacttttgt tcaacctggt gtagactcac cttggtcaca atgcactgtc  25740
ctttttatat attgctagat tcaatttgaa gaatattttg ttaggatttt agcaactctg  25800
gttacaagag acgctggtct ataatttttt tttctttata atgtttttgt caggttttcc  25860
tgttaagatg atgctggact tagaaaagca gttggaaaat gcttttaaaa tactctttgg  25920
aagaatttat gtaatattca taatatttct gccttaaatg tttgggaaaa attaccggaa  25980
atgccagttg ggcctggaga tttctttgag gaaagttttt aaattagaag ttcaatttct  26040
ttctttcttt ctttctttct tttttttttg agatgggttc tagctctctc actcaggctg  26100
gagtgcggtg taatttcttt aatagtttat aggactgagc agattttcca tttttgtatc  26160
agtctgggga gtcttcccat ttccactcag ctttacactg attcatgcaa agttgttcag  26220
tgtcctctta gatggctctg agcccaacgc tgacatcctc ctcttccttc tgagaatctt  26280
atactgatct tttgaaaaaa aaaaaatctt agtctttgat tctgttttta aagagacttt  26340
atttttggtt tcatcaattt ctattgtttg ttattttctt tctttcttaa ttttttttgag  26400
atggagtctt gctctgttgc tgaggttggg gagcagtggc gtgatctcag ttcactgcaa  26460
cctccgtttc cggggttcaa gcgattctcc tgcctcagcc tcccgagtag ctgggactac  26520
aggtgctgac caccatgact ggccaatttt ttggtatttt tattagagac agggttttac  26580
catgttgtcc aagctggtct tgaactcctg acctcaggtg atccaccttc cttggcctcc  26640
cagagtgctg ggattacagg tgtgagccac cacactggcc tttgctattt tctttctcct  26700
ttatttttct aacttgaata cttagatatt tgattttcag gcttttattg aaatatgaat  26760
ttgaggctat aaatgagttt tgagatatca ttcagttaaa tgtgtgttct ggtgcttgct  26820
gtggtagcac agatactaaa agtgttttct gtttctactg ttcttctctg gcccatgagt  26880
tatgtgggag tatgctgctt catttacaat ctgagaatgt tctggtgtgg ttttttttgga  26940
agccgtggat ggagcagggg ttttcttgtg cttcacaggt gcagctagga gggcactgtg  27000
tccagggtct tctgtcggcc tggcgtggcc cttggccatg tgctgctctg cggcatgagg  27060
tgggcgtgag ttgtcctcag ccacatttag agaattggcc ttttaaaaaa tagatcatct  27120
tttaaaaatc actgtaataa aagtaaagca ggttctttgc aaacaagact tgcaaaatac  27180
agagaagcgc aaagaagaag ctaagtcgcc cctcctcgcc cctgaaggag aatctgctgt  27240
tgctgtttgg tctccacatt tccatggcgg cttgctgccc ctttcacgcc tggcccactt  27300
tgtgcctggt gaggtttcta aaagccccac ccttgagcgc gctcctccag cacgagcagt  27360
aatggcacag gtgttgtgtc attttactca gtagcctctg ggttattttt cagttttcct  27420
tgttgttttt tagcttttcc ccattttaac cttaactggt attttcttgt taaatattta  27480
ttcatgacca ttattattcc ctagagccac atggcttggg gtccacctgc ctgggtccgc  27540
ccccatccct gccccttctg gctgtctgac ctggcctggt gacttctctt ctctgctcat  27600
ctctctccct gcctgagtgg gcaagagtac agcctcacag agtggtggga ttgtgtgaga  27660
tgccacaggg aagcacatgt cagttgttgt cactgtgtag aacaatgagt cccggatgtg  27720
gcccgcaggg gagcaatggt gacttaatcg cgggcttcct ctgcatttct ttggtgactt  27780
ccaagctaga acattctttt tttgtttatt tgtttgaagc agggtctcac tctgttacct  27840
```

-continued

```
aggctggagt gcagtagcaa aatcatggct caccacagtc tcaaacttcc gggctcaagc  27900
aatcctccca cctcagcctc ctgagtagct gggactacag gtgcatacca tcacctgtgg  27960
ctaatttttt aaatgttttg tatttttttaa atgttgctca ggctggtctt gaactgctgg  28020
gctcaagcaa tcctcccacc tcggcctccc caaatgctgg gattacagag tgagccacca  28080
cacccagcca tttttaaaat tttcaccagg aagtttttttc tttcattttt aagcacagta  28140
agtatttgtg tattatgtta cagatatttt cccctcaatt tctttgttct ttttatctct  28200
ttagggagta tgaacataag tttttaactt ttaaatggtt aaatatatta gtgtgatttt  28260
tatattaaga ttttatttta tttatttttt tttttttttga gacggagtct cgctctgtcg  28320
cccaggctgg agtgcagtgg cgggatctcg gctcactgca agctccgcct cccgggttca  28380
cgccattctc ctgcctcagc ctcccaagta gctgggacta caggcgcccg ccactacgcc  28440
cggctaattt tttgtatttt tagtagagac ggggtttcac cgttttagcc aggatggtct  28500
cgatctcctg acctcgtgat ccgcccgcct cggcctccca aagtgctggg attacaggcg  28560
tgagccaccg cgcccggcct atattaagat tttaaacttg ccgggcgcag tggctgacgc  28620
ctgtaatccc agcactttgg gaggccgagg cgggtggatc acaaggtcag gagatcgaga  28680
ccatcctggc taacacggtg aaaccttgtc tactaaaaat acaaaaatta gccgggcgtg  28740
gtggcgggcg cttgtagtcc cagctactcg ggaggctgag gcaggagaat ggcgtgaacc  28800
cgggaggtgg agcttgcagt gagccgagat ggtgccactg cactccagcc taggcgagag  28860
tgcaagacac cgtctcaaaa aaaaaaaaaa gattttaaac ttacctggag agtttttgag  28920
atacagtttg gagttgcaag ttactttaac actatttata tggaatattc tattttacta  28980
gacagactta aattctccct taaattcaca aatttataga aaagttacaa aaatactgaa  29040
aagtgctcct gtttactctg actagaattc tttagtgggt ggcaccctac cctgagggct  29100
tcatgacctg tcctcccaca tgatccaggc tctaccctca gggcttcatg acctgtcctc  29160
ccacatgatc caggctctac cctcagggct tcatgacctg tcctcccacg tgatccaggc  29220
tctaccctca gggcttcatg acctgtcctc ccacatgatc caggctctac cctcagggct  29280
tcatgacctg tcctcccacg tgatccaggc tctaccctca gggcttcatg acctgtcctc  29340
ccacgtgatc caggctctac cctcagggct tcatgacctg tcctcccacg tgatccaggc  29400
tctaccctca gggcttcatg acccttcctc ccacatgatc caggctctac cctgaggact  29460
tcatgacctg tcctcccacg tgatccaggc tctaccctca gggcttcatg acctgtcctc  29520
ccacatgatc caggctctac cctcagggct tcattacctg tcttcccaca tgatccaggc  29580
ccattctttc ttgaaccatt ggaaaggaat ttgcagatag gatgtgtacc cctaactgcc  29640
tgagtatttc ttagcaggtg tattcttttg tgcaagtgta agtcagaatg ttaatgttga  29700
tgaaatacta atctgcaggc ctaattgttc caataatgtc ctttatggca aaatcttccc  29760
ctcaagcttt aatccaatat catgggttgc atttgtttat ttttaattat ttttcttttc  29820
tttttctgtt ttccttaccc ttctcactgt gcacatgggt tgcatttagt tatcacattg  29880
acacccttttt aacctggaat aattccttaa tctttccttg tgtttgatga ctttgtcatt  29940
tttgaattgt tccacaagtt attttgtaga atatcctcag tgtttttttt tttctggtgt  30000
ctcgtgatta gattcaggtt atgaaactac atttttgtca ggaagattgc agaagaaatg  30060
gggccttctc ctgcacctta ccaggaagca cacaccaact ttgatccctt gattaaggtg  30120
atgaccgctg tacttagttt ctccgctatg aagttgcttt ttttttcttt gtggggagac  30180
```

-continued

```
agttttagac tatgtaaacg tcctatttct catcatactt atacctgtta gtgttagcat  30240
ttgatgatga ttcttgcctg aatcaattat ttgcataatg cttacaaaat tatcattcct  30300
tccatatgta ttagttggtg ttcttccaaa agcttttcct ttgcctctgt ttatttactt  30360
atttatcact gtggacgcat agattcttac gcaattgatt ttgatactga tctcatagct  30420
agacaatttt gctaaacttt taaaaaaatt tatgtacttt atcttttata gcagctttaa  30480
atttacagaa aatttgagtg gaagatgcag tgttcccata aagccgctaa ctcctcgcac  30540
cttccctcaa gtttccccag tactaacatc ttgcattcaa gtggtgcgtt tgcaacattc  30600
ataaattatt atcgtccaga gtccattgtt tacattcagc ttcctcttca tgttgttcat  30660
tctgtggttt cacagatgtg tgatgcatgt gcccaccact gcagtgtcac acaggatctc  30720
actgccccgg agtcctctgc gctgtccccg cctccagaac cccttagtag caaacactga  30780
tatttttact gtctccatag ttttgccttt tcagactgac ctatttcact tagtaagaag  30840
catttaagat tcctgagtct ctttctatgg ctcaatagca catttctttt tagtgctgaa  30900
taatattcca ttgtctggat gtaccacagt ttattcattc acctactaag gtgaatgtct  30960
tgcttgcttc caagttttgg caactatgaa taaagttgct atcaatgtta gcgtgcacat  31020
aagttttcag ctcatttggg taaatgccaa gaagcatgat tgcgggatcc tatggtaaga  31080
gtgtgtttag ttctgtaaga agctgccaaa ctgtatctta agtggctgca ccatttgcgt  31140
ttccaccagc aatgatgagc gttttgttgc tccacatcct caccagcatt tgctgttgtg  31200
ttttgggttt tagcctttct aagaggtgtg tagtggtatc tccttgtttc aatttgcaat  31260
tccctaatga cattatgtta aaatcttgtc atatagttat ttgccatctg tgtatctttt  31320
tcagtgatgt gtcctttaaa gtctttggct catttttaaa ttaaattttc ttattgttga  31380
gttttagttc ttcatatatt ttggctgcca gtcctttatc agatatgtct ttcgcaaata  31440
ttttctgcct gtgtcttgtc ttttcattct attaacagta tcttttgcag agccagtttt  31500
catttcaagg aagtccagct tatcaatgtt ctctttcatg tatcatgttt ttggtgttgt  31560
atctaaaaag ttactgccaa gcccaagggt acctagattt tttcctgtgt tatattctag  31620
gatttttaaa gttttgcatt ttacatctag gtccatgatt cattttgagt taacttttgt  31680
gaagggttta tggtttgtgt ctagattttt tttttttttt ttttttttgca tgtggatgtc  31740
cagttgtttt ggtaccatct gtcaagaaga ctctttttgg gtcattttgt tgcctttgtt  31800
tctttgtaaa aaatcagttg actgcatttg catgggtcta tttctgagct ctctgttcca  31860
ttgcattgat ctgtttgttc ttctcagcaa tcccacactg tcttggttcc tgtagctctg  31920
tagtaggcct tgcagtcagt taccgcccct gttctcactt cagtgttctc ttcaatagtg  31980
ttttgactat tctaggtttt ttccctctcc atatacattt tagagtcagt ttgtcaatag  32040
tttacaaaat aacttgctga gactttgatt gggattacat tgaatctgta gctcaagttg  32100
gaaagatctt ttatttcttt catcagaatt ttgtagtttt catcatatat agatcttgta  32160
catattttgt tgtttatacc taaggatttc atttttttgg tgctaatgta aatggcgttg  32220
tgttttaaat gtcaaaatct aattgttcat tgctggtagg aaaacaactg accctttttt  32280
ttttttttaa gggacgcagt cttactctgt tgcccaggca gagtgcagtg gtgccatcat  32340
agctcactgc agcctcaaac tcctgggctt aaggaatcct cctgtctcag cctcctgagc  32400
agctaggacc acaggcatgt gccactacgt tcagctaatt tttcaatttt tttgtagaga  32460
tgggatcttg ctctgttgcc caggctggtc tcaaactccc gtctgctttg agatgattat  32520
atatttgtgt cctttgttaa tttagaggat tattatggat ttttctaatg ttaagacacc  32580
```

-continued

```
tttgtatttc tgagatcgac cttagtattg gtctatattt aagacagtat tcagtttctc  32640
agttgttttt tgtttttttgg ttttttttttt tgagacagag tctctgtctc ccaggctgga  32700
gtccagtggc acaatctcag ctcaccgcaa gctctgcctc ccggattcac gccattctcc  32760
tgcctcagcc tcccgagtag ctgggactac aggcgcctgt catcatgccc agctaatttt  32820
ttgtattttt agtagagacg gggtttcacc atgttagcca gggtggtctc aatctcctga  32880
cctcgtgatc tgcccacctc gatctcccaa agtgctggga ttacaaggcg tgagccactg  32940
cgcccggcag cagtttctca gttttaattt ggagttttgc atctgtgttc atgagtgagc  33000
ctgaaatttt cacttttcca tatcttattt ctctgggttc ctagaatgag ctagagagtg  33060
ttcctccttt ctgttctctg gaagagtttg tgtgagatta gaatgagtgt gtctgataat  33120
ttagttgcat tcatttataa aattcctagg cctagagttt tttttctgggg aaaagtttac  33180
attttgactc attttttttag tagttttagg actgtttagg ttctctattt cttgattgag  33240
ccagttttga taagttaatc tttctaattt gtagatattt tctctaagtt tgcaaatgta  33300
atacataaaa ctttcttgtc atttctcacc atatctgtag ttctatcttt ttattgctaa  33360
tattactaat ttgtactttg actatttgta tttgttacct gttgccgagt aacaatatta  33420
gtacaaacct agtggcttag aacaacacac attgattact tcaccgtttc tgtgtgtcag  33480
aagtccaggc gcggcctcgc aggtcgtcct ctgcctcagg gtctctccgg gcttcagtca  33540
gggtgttagc caggaccggg gtctcgcctg agcttccagt gaggaaggat ctgcctctga  33600
gcacacaggg tcctcggcac gatcccattc ctcagctgga agctgccgac tgccgtctgc  33660
tgcggggcct ctctagatgg catcttcaca aaagcgagaa gggagagttg gtagagggag  33720
tctgctagca ccatgggagt cgcggtcaca cagacctcgg tcccaggacc cgcacccatc  33780
aaccctgccg tgatctgctg gttaaagaca agtcccacgt cccacagggt gacactggag  33840
tagacacttc gctctggcct tttcagagaa ctggttattt tttggaaata tcagttagat  33900
gtaggatggg tcttgtcttc taaatctatt gttttctctc taattgattt tttcctgttt  33960
ttatttagtt cactttgttg ggtttgctca agcctgggtc actggatctc agggatgctg  34020
ctcctgtttg cagctgtgtc tgcaggggct tcccaaggcc ttgctttccc ctcacgtccc  34080
tttctcagac tctgccaatc cgcttcccgc tctggtgtcc tgtggttgct tctttttaaa  34140
accctcatcg gtctgtgtaa actgtttatt tttatgtggt ttttaaggga gaccattctc  34200
attcttttga gaccctggaa aggatggaat tgggataggt aaactgctgt tttaccagaa  34260
tgttcactgg accaatctcg tgttccaggg agaccctcac gcagggctta gagttctgtc  34320
ggcggcagca gagggccgat ggctcctggg aagggtgagt gagcctccac tcgtgagtgc  34380
agagatgcat gggatccaga ggtttctgct ctcacacact gcgttcataa atgttggctt  34440
gtatgttgtt gctacaccag aagtttctgg aagtgagctg ccagcccgtg acttctgggg  34500
gacctcgttc ctttgtggca tgcgtggcct ttgccccggt ggaaattgct cagtacgttg  34560
ctgggcgcag ccgggctgct gggagcgcgc tgtagcctga gcgtggctat tccctccacc  34620
ctttctgctt gctcttaggg tccagcagac agagctgctg tcttccacgg ccttaatgcc  34680
tgaggcactg gagttggtgg gctggctggg gcacgtgtga ttgttgcaga atgcgtgttg  34740
tttcacacac cggctgtgaa cagggtggaa gggctgaggc tctccctgtt tccctccagc  34800
tcctggggag tttgcttcac ctacggcacc tggtttggcc tggaggcctt cgcctgtatg  34860
gggcagacct accgagatgg gtgagtgagt gcctgtcctc tggtgggtgg gggttctcaa  34920
```

-continued

```
cccaatgctc tgtcatgagt gttttttgct ttgacatttg gttttagggt ttgtttgttt  34980
gtttgtttgt ttttgagacg gagtctcgct ctgtcaaccg ggctgacatg cagtggcatg  35040
atcctagctc actgcagtct caaactcgtg ggctcaagcg atcctcccga gtagctggga  35100
tcacaggtgc acgccaccac cccgggctaa tcttttaaaa cttttatgta gagatggagt  35160
cttgctgtgt tgctcacact ggtttgggct caagcagtct tcctacctcg gccttccaaa  35220
gtgctggggt tacaggcatg agccaatgtg cctggcctgt ttttaatatt tttaaacagt  35280
gagataagat ccccggttga aatgaagatg tttccctggt cccacagctc tctggagctt  35340
cctgacatgt atgctggagg gacgcttctg gtctccggcc cctccaggca tacagatgcc  35400
tcccaaccct gagtaggaag attagggtcc acggcctcgc tggagcgggt tagaaggcag  35460
gagatctccg gtcccagccg tgtctccagc cgccggactc tctcccagcc ctgtctccag  35520
ctgccccact gtctcccaga gtctgccgtg tggatgttta gaggtgggga gcaccgtgct  35580
tggctgagtg cagcttgtga gacgctgctc ccaagcactg cagacctcac tcagcctgac  35640
gcgtccgtga ggccatcctc ggtactcgca tgtccctttg tcttcccagc gactctggga  35700
ggcaggagta tctgttccca gttcacatct gcaaaagtca agctcgggtt tcagtagtgg  35760
cccatggccc ttaggtaggg tggccccatc gtgcaggctc ctccccgtac cccaaggcag  35820
cctgctgggg tgagaagcca ggggtctggg accttccttg gtgtgatggt gtctcctgtc  35880
tctggtcttt gcaggactgc ctgtgcagag gtctcccggg cctgtgactt cctgctgtcc  35940
cggcagatgg cagacggagg ctggggggag gactttgagt cctgcgagga gcggcgttat  36000
ttgcagagtg cccagtccca gatccataac acatgctggg ccatgatggg gctgatggcc  36060
gttcggtggg gacgacggga ccgtccctga gccttgggtt tgggtagagg agggacactc  36120
agctgtgagc cggtggcctg ggctgagtga atgtagagag gaggggaggc ctgtgggcca  36180
ggtcagctgc cactctggga acagacacct acaagagcca catgcctggt tcctggggca  36240
agaacgtggg ctgctctgac caagtggggc cctgcagaga ggctcgcctc ttagaagtga  36300
accacccacc attagccatg tcagtggaag agcaagcaca tcagggaccc atggaaacag  36360
cgaggtgggc tgcgatgagg atgctgcttc ctggtgtggt agtgatgacg gtcacagcag  36420
ctgctctctg tggccctact gtgttcacag ctggtgctga gccacatatg tgccaggtgc  36480
acacacacgc agacgcatgc aggcaggcat cagtgtacac actgatgtgc acacacagat  36540
gtacatggag acagatgcac acacaggcct atgcacacac gtacgcatgc ccacacaggc  36600
acctgtgtcc acacacatac agatgcaccc acagcatccc atctgtgcca cacactgaca  36660
taggtacatg gagacagatg cacacacagg tctgtgcaca cacgtatgca tgcacaggca  36720
cctgtgtaca cacacgtaca gatgcaccca caggatccca tctgtgccac acacagacgt  36780
aggtacatgg agacagatgc acacacaggt ctgtgcacac acatacatac gcatgcacag  36840
gcacctgtgt acacacatgc agatacaccc acagcatccc atctgtgcca cacacagaca  36900
taggtacatg gagacagatg cacacacagg tctatgcaca cacatacgca tgcacaggca  36960
cctgtgtaca cacacgtaca gatgcaccca caggatccca tctgtgccac acacagacgt  37020
aggtacatgg agacagatgc acacacaggt ctgtgcacac acatacatac gcatgcacag  37080
gcacctgtgt acacacacgc agatacaccc acagcatacc atctgtgaca cacacagacg  37140
taggtacatg gagacagatg cacacacatg tctgtgcaca cacatacata cgcatgcaca  37200
ggcacgtgtg tacacacatg cagatacacc cacagcatgc catctgtgac acacacagac  37260
gtaggtacat ggagacacat gcacacacag gtctgtgcac acacatacgc atgcacaggc  37320
```

-continued

```
acctatgtac acacatgcag atacacccac agcatcccat ctgtgccaca cacagacata  37380
ggtacatgaa gacagatgca cacacaggtc tatgcacaca cgtatgcatg cacaggcacc  37440
tgtgtacaca catgcagatg cacccacagt atcccatctg tgccacacac agacatacgt  37500
acatggagac agatgcacat acaggtctat gcacacatgt acacatgcac aggcacctgt  37560
gtacacacat gcagatgcac ccgcagtatc ccatctgtgc catacacaga catacgtaca  37620
tggagacaga tgcacataca ggtctatgca cacatgtaca catgcacagg cacctgtgca  37680
cacatatgca gatgcacccg cagtatccca tctgtgccac acacagacat acgtacatgg  37740
agacagatgt acacacaggt ctatgcacac atgtacacat gcacaggcac ctgtgtacac  37800
acatgcagat gcacccgcag tatcccatct gtgccacaca cagacatacg tacatggaga  37860
cagatgcaca cacaggtcta tgcacacatg tacacatgca caggcacctg tgcacacata  37920
tgcagatgca cccgcagtat cgcatctgtg ccacacagac atacgtacat ggagacagat  37980
gtacatacag gtctatgcac acatgtacac atgcacaggc acctgtgcac acatacatac  38040
agatgcaccc gcaacatccc gtctgtgctg ccctattagg tttgtggcca tttggggaat  38100
cttcctaaaa ccctaaaagc tagggcaggt ctgcttgagc aggagcagca gggtctgggg  38160
gacccctgag ggcaggacag tcagggaccc acagttgagc tgggcccgct gagccctgga  38220
tccttcttgg tgtcttatcc tggccagcaa gcaagtgtga gctcctgtgg gtctccagag  38280
gcccatgagg accagtgggc cagttgggaa caaggcttgg cgtcctcttc aggggggaac  38340
accagggcag gcctgaggag gcctgtgtcc ccagcctgtc attgctgtgg ctccgcttct  38400
cagggagcct aggaagaagg tgtggcaaga gcccgaggcg ctggctgcac ctggcggggc  38460
ctgtgggcgt cagtttagac ccatccattc tcactgcagc attccagggt ttgcccttat  38520
gctcggctgt gtgagggtga ggatgatgct gtgggggcat gcatgctggg tgtgtttcag  38580
ccttctcttc caccaggcat cctgacatcg aggcccagga gagaggagtc cggtgtctac  38640
ttgagaaaca gctccccaat ggcgactggc cgcaggtatg ccgccaggga cctgagcgca  38700
caaggcccag cactgacctc cagcgtgcat ggctgtttcc acgtccccct gctctgtgtc  38760
ctttttgggg tactttggac acttgggagg cgtcacctct gccagtgaat gccacagttg  38820
gtggcaggtc tgtggcaggt ggtcgggtcc taaagtccag atcttgctgt tgtttcaagt  38880
gatgctctgg gtgggggagg agctggatgg gagaagccag tgggcgggaa gcctttttgc  38940
tgcaggacag accctcccac tccagatgac ctagtggccc ctcactgagc cagaagtccc  39000
tgtggtgtgg gtgtcatgag gtcatgtgag gccaaccgcc ctcccctggg atgaggctga  39060
gttggtggaa gctgatgtgg ttgtgagggg ctggtgaccc tggcttaggg tttgctgcag  39120
ggcggggagt ctgagctggg ctgatggtgc catgactgat gcgggatgga ctacttgctt  39180
tcctatgctc ttgcttaatt agccctttcc aggctgactc acccacaagc cagccaagcc  39240
aacagccagg gctccagttc agggactagc cctcagctga ctggtgaagc ctttgtgttt  39300
atttctctgt gttcttttag gaaaacattg ctggggtctt caacaagtcc tgtgccatct  39360
cctacacgag ctacaggaac atcttcccca tctgggccct cggccgcttc tcccagctgt  39420
accctgagag agcccttgct ggccacccct gagaacatgc ctacctgctg ggtgccgtct  39480
gtgcgttcca gtgaggccaa ggggtcctgg ccgggttggg gagccctccc ataaccctgt  39540
cttgggctcc aacccctcaa cctctatctc atagatgtga atctgggggc caggctggag  39600
gcagggatgg ggacagggtg ggtggcttag actcttgatt tttactgtag gttcatttct  39660
```

-continued

```
gaaagtagct tgtcgggctt gggtgaggaa gggggcacag gagccgtgac ccctgaggag  39720
gcacagcgcc ttctgccacc tctgggcacg gcctcaaggt agtgaggcta ggaggttttt  39780
tctgaccaat agctgagttc ttgggagagg agcagctgtg cctgtgtgat tccttagtgt  39840
cgagtgggct ctgggctggg gtcggccctg ggcaggcttc tcctgcacct tttgtctgct  39900
gggctgaggg acacgagggc aaccctgtga caatggcagg tagtgtgcat ccgtgaatag  39960
cccagtgcgg gggttgctca tggagcatcc tgaggccgtg cagcagggag ccccatgccc  40020
ctgggtcgtg agcttgcctg cgtatggggt ggtgtcatgg agcctcatgc ccctgggtcg  40080
tgagctcgcc tgagtatggg gtggtgtcat ggagccgcat acccctgggt tgtgagctcg  40140
cctgcatatg cagggtctgt catggaacat cccaagtctg tgcagcaggg gagccccatg  40200
cccctgggac atgaacccac ctgcgtggaa tgctgtttgt gaggtgtcta cagggtttat  40260
agtagtcttg tggacacaga aatgcacagg ggacacttac ggacacagaa atgcacaggg  40320
gaggccgagc ataaccaggg gtgaggggca ggcagcagtt gtagttactg ccgcggggca  40380
ctgctatgtg cagggacagc cagcgcccag cccatcacca ctccctgggc tggctggcag  40440
gtatggcacc ctgggagccc ggcatatacc cagggcaccc ctacggctgc cgccagtctc  40500
atgcccaggt gggtgctctg ggctggagcg agggccaggt tttgggccga ggcttcccca  40560
ggcaatcctg tgagctccct tctagcctct gacccagtct ggtctggctt gcatggatgt  40620
agggcttggg gtgggaagtt caggtcctgg ctttgccttt gcctgatgtg gatgagcagc  40680
tcacatgctc agggccacct gagactgtca ctgctctccc ctggctactg ggaggagtca  40740
ctgagagctt cgttacccct gctgccttgc ccagggcaca ccctatacct cctcatctgc  40800
tcttcccctc cctgccgcct tctgggcagg tagcagtccc tggcctctcc ccctggctga  40860
tcactctccc tcaggcagtg gagatctgcg tctggacacc ctcagatcct gtcattgcct  40920
gcccagagtc cttcaggggc acccctctgc cttggtgtgc ggtccagggc tctcacccag  40980
gtgccgcacc ctctggggtc ttctgtccag ctcccttgcc ccatgtgctg tcactgactc  41040
tccttgggac tcgcctgcct gctcagagcc ctgcagggct tggtcagctg cctgttcagt  41100
gtcaacactt ccctgcacat cttaaaactg ggctttattt tcgctgaagg aactgtgttg  41160
ggacccttga catctgtcag gtttgcacat gctgtttttt tttctcagcc cacgtgttct  41220
cccccacgtg gggtagcagc aggacagaca gtgaatcaca gagtctgccc tgagcagagg  41280
ctgctgtccc tgggactcct agccatggtc agactgtaca aaacggtttt ccagaaatga  41340
aatgtaaatc catttttata ctgaaaatgt tactgaaagt cacttttatg agcatctgcc  41400
ttaataaaca gacattgatt cccttatcag aagcctgtca cactgtgttt cgtttcatcc  41460
tggggagaac tgcagatttg gggtttctgg ctgtcatacg tcacctgcct gtggggcgag  41520
tgggaggccc agcctggttt agggaacaag agtgacgtga ggagtagcag ggtgcgtctc  41580
cagttacctg agggaaaaca gatattttaa gagataatag catagcctat tttaatatgt  41640
tttaaaggcc ataagcatat ccaggaagat aaataaacgt gatacaatgt ccacatagga  41700
ggaactttct ttcactgcat tgttttcctt cacagtggcc ttcaagtcac aggacgcagc  41760
gattccctgc cctcttcggt gttattacac aggcaggact tcagtgtcag tatccctgcc  41820
ttcagtcttc tttagaaatc acatctgtgt tcaatccatt gtttagaggg agtgtatttt  41880
tcctgttcca cgaagaggac tttttgttca caattggatc acaatgcaga ggagtctgtt  41940
cctcccccgt cggcttctcg gtgctgggag ggtgacctgt cccagatgac tcatcaccct  42000
gacatgctct tgacaaagga caccaccaag aggagatggc agctgtaccg gtgcagcctc  42060
```

```
tgtctgaggg ggatatttgc ctcagtgtga ttaaaaatca gtcatgaaag atttttgaat  42120

tcagattatt tttatcagga acagattttg aacatcctga aatcttttcc ctggcatcat  42180

attaggtttt ctttgttcac tatgatgtaa agtttcagac tcttgatatt tttaatatca  42240

acatagacgg taggacaagg aacggtacca gaaatgagta aagagacaat aatgataaga  42300

tcgatttatc aagacataac aaccccaaat gtatatgcac taaataacag cttcaaaata  42360

catgaagcaa aatggcagaa ttgaagagaa tgagataaaa acagaatttt aacgggtgct  42420

ttccgtactt tgtaactgac agacatgaga                                    42450
```

```
<210> SEQ ID NO 4
<211> LENGTH: 732
<212> TYPE: PRT
<213> ORGANISM: Human

<400> SEQUENCE: 4

Met Thr Glu Gly Thr Cys Leu Arg Arg Arg Gly Gly Pro Tyr Lys Thr
 1               5                  10                  15

Glu Pro Ala Thr Asp Leu Gly Arg Trp Arg Leu Asn Cys Glu Arg Gly
            20                  25                  30

Arg Gln Thr Trp Thr Tyr Leu Gln Asp Glu Arg Ala Gly Arg Glu Gln
        35                  40                  45

Thr Gly Leu Glu Ala Tyr Ala Leu Gly Leu Asp Thr Lys Asn Tyr Phe
    50                  55                  60

Lys Asp Leu Pro Lys Ala His Thr Ala Phe Glu Gly Ala Leu Asn Gly
65                  70                  75                  80

Met Thr Phe Tyr Val Gly Leu Gln Ala Glu Asp Gly His Trp Thr Gly
                85                  90                  95

Asp Tyr Gly Gly Pro Leu Phe Leu Leu Pro Gly Leu Leu Ile Thr Cys
            100                 105                 110

His Val Ala Arg Ile Pro Leu Pro Ala Gly Tyr Arg Glu Glu Ile Val
        115                 120                 125

Arg Tyr Leu Arg Ser Val Gln Leu Pro Asp Gly Gly Trp Gly Leu His
    130                 135                 140

Ile Glu Asp Lys Ser Thr Val Phe Gly Thr Ala Leu Asn Tyr Val Ser
145                 150                 155                 160

Leu Arg Ile Leu Gly Val Gly Pro Asp Asp Pro Asp Leu Val Arg Ala
                165                 170                 175

Arg Asn Ile Leu His Lys Lys Gly Gly Ala Val Ala Ile Pro Ser Trp
            180                 185                 190

Gly Lys Phe Trp Leu Ala Val Leu Asn Val Tyr Ser Trp Glu Gly Leu
        195                 200                 205

Asn Thr Leu Phe Pro Glu Met Trp Leu Phe Pro Asp Trp Ala Pro Ala
    210                 215                 220

His Pro Ser Thr Leu Trp Cys His Cys Arg Gln Val Tyr Leu Pro Met
225                 230                 235                 240

Ser Tyr Cys Tyr Ala Val Arg Leu Ser Ala Ala Glu Asp Pro Leu Val
                245                 250                 255

Gln Ser Leu Arg Gln Glu Leu Tyr Val Glu Asp Phe Ala Ser Ile Asp
            260                 265                 270

Trp Leu Ala Gln Arg Asn Asn Val Ala Pro Asp Glu Leu Tyr Thr Pro
        275                 280                 285

His Ser Trp Leu Leu Arg Val Val Tyr Ala Leu Leu Asn Leu Tyr Glu
    290                 295                 300
```

-continued

```
His His His Ser Ala His Leu Arg Gln Arg Ala Val Gln Lys Leu Tyr
305                 310                 315                 320

Glu His Ile Val Ala Asp Asp Arg Phe Thr Lys Ser Ile Ser Ile Gly
                325                 330                 335

Pro Ile Ser Lys Thr Ile Asn Met Leu Val Arg Trp Tyr Val Asp Gly
            340                 345                 350

Pro Ala Ser Thr Ala Phe Gln Glu His Val Ser Arg Ile Pro Asp Tyr
        355                 360                 365

Leu Trp Met Gly Leu Asp Gly Met Lys Met Gln Gly Thr Asn Gly Ser
    370                 375                 380

Gln Ile Trp Asp Thr Ala Phe Ala Ile Gln Ala Leu Leu Glu Ala Gly
385                 390                 395                 400

Gly His His Arg Pro Glu Phe Ser Ser Cys Leu Gln Lys Ala His Glu
                405                 410                 415

Phe Leu Arg Leu Ser Gln Val Pro Asp Asn Pro Pro Asp Tyr Gln Lys
            420                 425                 430

Tyr Tyr Arg Gln Met Arg Lys Gly Gly Phe Ser Phe Ser Thr Leu Asp
        435                 440                 445

Cys Gly Trp Ile Val Ser Asp Cys Thr Ala Glu Ala Leu Lys Ala Val
    450                 455                 460

Leu Leu Leu Gln Glu Lys Cys Pro His Val Thr Glu His Ile Pro Arg
465                 470                 475                 480

Glu Arg Leu Cys Asp Ala Val Ala Val Leu Leu Asn Met Arg Asn Pro
                485                 490                 495

Asp Gly Gly Phe Ala Thr Tyr Glu Thr Lys Arg Gly Gly His Leu Leu
            500                 505                 510

Glu Leu Leu Asn Pro Ser Glu Val Phe Gly Asp Ile Met Ile Asp Tyr
        515                 520                 525

Thr Tyr Val Glu Cys Thr Ser Ala Val Met Gln Ala Leu Lys Tyr Phe
    530                 535                 540

His Lys Arg Phe Pro Glu His Arg Ala Ala Glu Ile Arg Glu Thr Leu
545                 550                 555                 560

Thr Gln Gly Leu Glu Phe Cys Arg Arg Gln Gln Arg Ala Asp Gly Ser
                565                 570                 575

Trp Glu Gly Ser Trp Gly Val Cys Phe Thr Tyr Gly Thr Trp Phe Gly
            580                 585                 590

Leu Glu Ala Phe Ala Cys Met Gly Gln Thr Tyr Arg Asp Gly Thr Ala
        595                 600                 605

Cys Ala Glu Val Ser Arg Ala Cys Asp Phe Leu Leu Ser Arg Gln Met
    610                 615                 620

Ala Asp Gly Gly Trp Gly Glu Asp Phe Glu Ser Cys Glu Glu Arg Arg
625                 630                 635                 640

Tyr Leu Gln Ser Ala Gln Ser Gln Ile His Asn Thr Cys Trp Ala Met
                645                 650                 655

Met Gly Leu Met Ala Val Arg His Pro Asp Ile Glu Ala Gln Glu Arg
            660                 665                 670

Gly Val Arg Cys Leu Leu Glu Lys Gln Leu Pro Asn Gly Asp Trp Pro
        675                 680                 685

Gln Glu Asn Ile Ala Gly Val Phe Asn Lys Ser Cys Ala Ile Ser Tyr
    690                 695                 700

Thr Ser Tyr Arg Asn Ile Phe Pro Ile Trp Ala Leu Gly Arg Phe Ser
705                 710                 715                 720
```

-continued

```
Gln Leu Tyr Pro Glu Arg Ala Leu Ala Gly His Pro
                725                 730
```